(12) United States Patent
Kim et al.

(10) Patent No.: US 11,667,608 B2
(45) Date of Patent: Jun. 6, 2023

(54) COMPOUND AND ORGANIC LIGHT-EMITTING DEVICE INCLUDING THE SAME

(71) Applicant: Samsung Display Co., Ltd., Yongin-si (KR)

(72) Inventors: Dongjun Kim, Yongin-si (KR); Minji Kim, Yongin-si (KR); Eunjae Jeong, Yongin-si (KR); Sohee Jo, Yongin-si (KR); Sanghyun Han, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 497 days.

(21) Appl. No.: 16/817,333

(22) Filed: Mar. 12, 2020

(65) Prior Publication Data

US 2021/0053920 A1 Feb. 25, 2021

(30) Foreign Application Priority Data

Aug. 23, 2019 (KR) .................. 10-2019-0103982

(51) Int. Cl.
*C07D 209/82* (2006.01)
*C07D 407/12* (2006.01)
(Continued)

(52) U.S. Cl.
CPC ......... *C07D 209/82* (2013.01); *C07D 407/12* (2013.01); *C07D 409/12* (2013.01);
(Continued)

(58) Field of Classification Search
None
See application file for complete search history.

(56) References Cited

U.S. PATENT DOCUMENTS 8,911,885 B2 * 12/2014 Kim .................. C07D 209/86
585/27
9,455,409 B2 9/2016 Lee et al.
(Continued)

FOREIGN PATENT DOCUMENTS

KR 10-2012-0088752 A 8/2012
KR 10-1462070 B1 11/2014
(Continued)

OTHER PUBLICATIONS

Machine translation of KR-20190035567, translation generated May 2022, 25 pages. (Year: 2022).*

*Primary Examiner* — Robert S Loewe
(74) *Attorney, Agent, or Firm* — Lewis Roca Rothgerber Christie LLP

(57) ABSTRACT

An organic light-emitting device includes: a first electrode; a second electrode facing the first electrode; and an organic layer between the first electrode and the second electrode and including an emission layer, wherein the organic layer includes the compound of Formula 1:

Formula 1

(Continued)

When the compound of Formula 1 is used in an organic light-emitting device, the organic light-emitting device may have high-efficiency characteristics as compared to a case where a compound of the related art is used, resulting particularly in excellent lifespan improvement effects, and accordingly, significantly improved lifespan.

19 Claims, 4 Drawing Sheets

(51) Int. Cl.
    *C07D 409/12*     (2006.01)
    *H01L 51/00*     (2006.01)
    *H01L 51/50*     (2006.01)
    *H01L 51/42*     (2006.01)

(52) U.S. Cl.
    CPC ...... *H01L 51/0061* (2013.01); *H01L 51/0072* (2013.01); *H01L 51/0073* (2013.01); *H01L 51/0074* (2013.01); *H01L 51/4273* (2013.01); *H01L 51/5024* (2013.01); *H01L 51/5056* (2013.01); *H01L 51/5072* (2013.01); *H01L 51/5092* (2013.01)

(56) References Cited

U.S. PATENT DOCUMENTS

| | | | |
|---|---|---|---|
| 9,484,545 B2 * | 11/2016 | Morimoto | ........... H01L 51/5072 |
| 9,650,565 B2 | 5/2017 | Matsumoto et al. | |
| 10,249,825 B2 * | 4/2019 | Lee | ........................ C09K 11/06 |
| 2019/0185460 A1 * | 6/2019 | Kim | ................... H01L 51/5016 |

FOREIGN PATENT DOCUMENTS

| | | | | |
|---|---|---|---|---|
| KR | 10-2016-0019745 A | | 2/2016 | |
| KR | 10-1848885 B1 | | 4/2018 | |
| KR | 10-1926340 B1 | | 12/2018 | |
| KR | 20190035567 A | * | 4/2019 | ........... C07C 211/61 |

* cited by examiner

| 20 |
|---|
| 190 |
| 150 |
| 110 |
| 210 |

FIG. 3

| 30 |
|---|
| 220 |
| 190 |
| 150 |
| 110 |

FIG. 4

| 40 |
|---|
| 220 |
| 190 |
| 150 |
| 110 |
| 210 |

COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2019-0103982, filed on Aug. 23, 2019, in the Korean Intellectual Property Office, the entire content of which is incorporated herein by reference.

BACKGROUND

1. Field

One or more aspects of embodiments of the present disclosure are directed toward a compound and an organic light-emitting device including the same.

2. Description of Related Art

Organic light-emitting devices are self-emission devices that have wide viewing angles, high contrast ratios, short response times, and excellent characteristics in terms of brightness, driving voltage, and/or response speed, compared to devices in the related art.

An example of the organic light-emitting device may include a first electrode disposed (positioned) on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, such as holes and electrons, may then recombine in the emission layer to produce excitons. These excitons transition from an excited state to a ground state, thereby generating light.

SUMMARY

One or more aspects of embodiments of the present disclosure provide a hole transport compound and a device including the same, wherein, when the compound is used in an organic light-emitting device, the device including the compound exhibits high-efficiency characteristics as compared to a device in which a compound of the related art is used, and accordingly, has improved lifespan.

Additional aspects will be set forth in part in the description which follows and, in part, will be apparent from the description, or may be learned by practice of the presented embodiments of the disclosure.

An embodiment of the present disclosure provides: a compound represented by Formula 1:

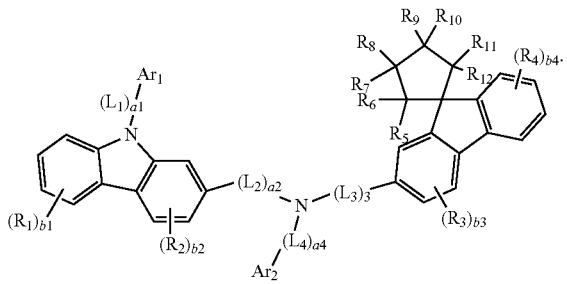

Formula 1

In Formula 1, $L_1$, $L_2$, $L_3$, and $L_4$ may each independently be selected from a substituted or unsubstituted $C_6$-$C_{60}$ arylene group and a substituted or unsubstituted $C_1$-$C_{60}$ heteroarylene group, a1, a2, a3, and a4 may each independently be an integer from 0 to 3, $Ar_1$, $Ar_2$, and $R_1$ to $R_{12}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —B($Q_1$)($Q_2$), —C(=O)($Q_1$), —S(=O)$_2$($Q_1$), and —P(=O)($Q_1$)($Q_2$), wherein two neighboring substituents among $R_5$ to $R_{12}$ are not linked to each other to form a ring, b1 and b3 may each independently be an integer from 1 to 4, b2 and b3 may each independently be an integer from 1 to 3, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted, a $C_6$-$C_{60}$ arylene group, the substituted $C_6$-$C_{60}$ aryloxy group, the substituted $C_6$-$C_{60}$ arylthio group, the substituted $C_1$-$C_{60}$ heteroaryl group, the substituted $C_1$-$C_{60}$ heteroarylene group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($C_{211}$)($C_{212}$)($Q_{13}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —B($Q_{31}$)($Q_{32}$), —C(=O)($Q_{31}$), —S(=O)$_2$($Q_{31}$), and —P(=O)($Q_{31}$)($Q_{32}$), and $Q_1$, $Q_2$, $Q_3$, $Q_{11}$, $Q_{12}$, $Q_{13}$, $Q_{21}$, $Q_{22}$, $Q_{23}$, $Q_{31}$, $Q_{32}$, and $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

Another embodiment of the present disclosure provides an organic light-emitting device including:

a first electrode;

a second electrode facing the first electrode; and an organic layer between the first electrode and the second electrode and including an emission layer, wherein the organic layer includes the compound represented by Formula 1.

Another embodiment of the present disclosure provides an electronic apparatus including:

a thin-film transistor; and the organic light-emitting device, wherein the thin-film transistor includes a source electrode, a drain electrode, an activation layer, and a gate electrode, and the first electrode of the organic light-emitting device is in electrical connection with at least one of the source electrode and the drain electrode of the thin-film transistor.

BRIEF DESCRIPTION OF THE DRAWINGS

The above and other aspects, features, and advantages of certain embodiments of the disclosure will be more apparent from the following description taken in conjunction with the accompanying drawings, in which:

FIGS. 1-4 are each a schematic view of an organic light-emitting device according to an embodiment.

DETAILED DESCRIPTION

Reference will now be made in more detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Throughout the disclosure, the expression "at least one of a, b or c" indicates only a, only b, only c, both a and b, both a and c, both b and c, all of a, b, and c, or variations thereof.

Expressions such as "at least one of," "one of," and "selected from," when preceding a list of elements, modify the entire list of elements and do not modify the individual elements of the list. Further, the use of "may" when describing embodiments of the present invention refers to "one or more embodiments of the present invention."

An embodiment of the present disclosure provides a compound represented by Formula 1.

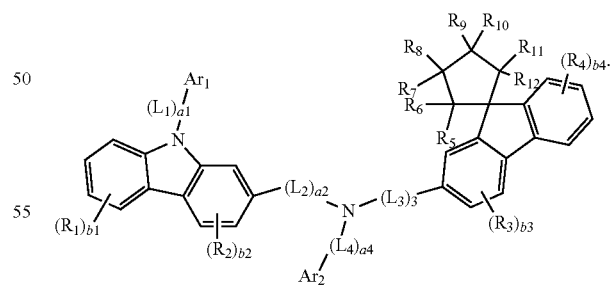

Formula 1

In Formula 1, $L_1$, $L_2$, $L_3$, and $L_4$ may each independently be selected from a substituted or unsubstituted $C_6$-$C_{60}$ arylene group and a substituted or unsubstituted $C_1$-$C_{60}$ heteroarylene group, a1, a2, a3, and a4 may each independently be an integer from 0 to 3, $Ar_1$, $Ar_2$, and $R_1$ to $R_{12}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$B(Q_1)(Q_2)$, —$C(=O)(Q_1)$, —$S(=O)_2(Q_1)$, and —$P(=O)(Q_1)(Q_2)$, wherein two adjacent substituents among $R_5$ to $R_{12}$ are not linked to each other to form a ring, b1 and b4 may each independently be an integer from 1 to 4, b2 and b3 may each independently be an integer from 1 to 3, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted, a $C_6$-$C_{60}$ arylene group, the substituted $C_6$-$C_{60}$ aryloxy group, the substituted $C_6$-$C_{60}$ arylthio group, the substituted $C_1$-$C_{60}$ heteroaryl group, the substituted $C_1$-$C_{60}$ heteroarylene group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(C_{211})(C_{212})(Q_{13})$, —$B(Q_{11})(Q_{12})$, —$C(=O)(Q_{11})$, —$S(=O)_2(Q_{11})$, and —$P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$B(Q_{21})(Q_{22})$, —$C(=O)(Q_{21})$, —$S(=O)_2(Q_{21})$, and —$P(=O)(Q_{21})(Q_{22})$; and —$Si(Q_{31})(Q_{32})(Q_{33})$, —$B(Q_{31})(Q_{32})$, —$C(=O)(Q_{31})$, —$S(=O)_2(Q_{31})$, and —$P(=O)(Q_{31})(Q_{32})$, and $Q_1$, $Q_2$, $Q_3$, $Q_{11}$, $Q_{12}$, $Q_{13}$, $Q_{21}$, $Q_{22}$, $Q_{23}$, $Q_{31}$, $Q_{32}$, and $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

Here, in the heteroaryl group and the heteroarylene group, a carbazole group and a carbazolene group are respectively excluded. For example, Formula 1 may have only one carbazole moiety.

In one embodiment, Formula 1 may have only one fluorene moiety in a spiro form.

In one embodiment, $Ar_1$ and $Ar_2$ in Formula 1 may each independently be selected from a substituted or unsubstituted $C_6$-$C_{60}$ aryl group and a substituted or unsubstituted $C_1$-$C_{60}$ heteroaryl group.

In one embodiment, $Ar_1$ may be selected from Formula 2a:

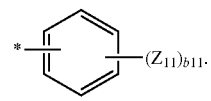

2a

In Formula 2a, $Z_{11}$ may be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a dibenzofuranyl group, a dibenzothiophenyl group, a triazinyl group, a benzimidazolyl group, and a phenanthrolinyl group; b11 may be an integer from 1 to 5; and * indicates a binding site to a neighboring atom.

In one embodiment, a1 in Formula 1 may be 0 or 1. For example, a1 in Formula 1 may be 0.

In one embodiment, a2 in Formula 1 may be 0 or 1. For example, a2 in Formula 1 may be 0.

In one embodiment, a3 in Formula 1 may be 0 or 1. For example, a3 in Formula 1 may be 0.

In one embodiment, a4 in Formula 1 may be 0 or 1. For example, a4 in Formula 1 may be 0.

In one embodiment, $L_1$, $L_2$, $L_3$, and $L_4$ in Formula 1 may each independently be a substituted or unsubstituted $C_6$-$C_{60}$ arylene group.

In one embodiment, $L_1$, $L_2$, $L_3$, and $L_4$ in Formula 1 may each independently be selected from:

a phenylene group, a pentalenylene group, an indenylene group, a naphthylene group, an azulenylene group, a heptalenylene group, an indacenylene group, an acenaphthylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, and an ovalenylene group; and a phenylene group, a pentalenylene group, an indenylene group, a naphthylene group, an azulenylene group, a heptalenylene group, an indacenylene group, an acenaphthylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, and an ovalenylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolylene group, a thiadiazolyl group, an imidazopyridinyl group, an imidazopyrimidinyl group, —Si($Q_{31}$)($Q_{32}$)($Q_{33}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

In one embodiment, $L_2$, $L_3$, and $L_4$ in Formula 1 may each independently be selected from groups represented by Formula 3a:

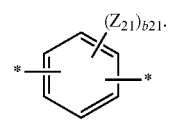

3a

In Formula 3a, $Z_{21}$ may be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a dibenzofuranyl group, a dibenzothiophenyl group, a triazinyl group, a benzimidazolyl group, and a phenanthrolinyl group; b21 may be an integer from 1 to 4; and * indicates a binding site to a neighboring atom.

In one embodiment, $Ar_2$ may be represented by one selected from Formulae 4a to 4d:

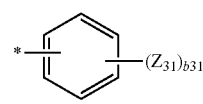

4a

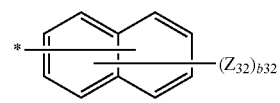

4b

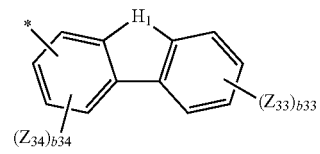

4c

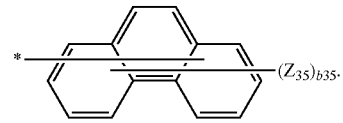

4d

In Formulae 4a to 4d, $H_1$ may be O or S; $Z_{31}$ to $Z_{35}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a dibenzofuranyl group, a dibenzothiophenyl group, a triazinyl group, a benzimidazolyl group, and a phenanthrolinyl group, b31 may be an integer from 1 to 5, b32 may be an integer from 1 to 7, b33 may be an integer from 1 to 4, b34 may be an integer from 1 to 3, b35 may be an integer from 1 to 9, and * indicates a binding site to a neighboring atom.

In one embodiment, $R_1$ to $R_{12}$ in Formula 1 may each independently be hydrogen or deuterium.

In one embodiment, Formula 1 may be represented by Formula 2 below:

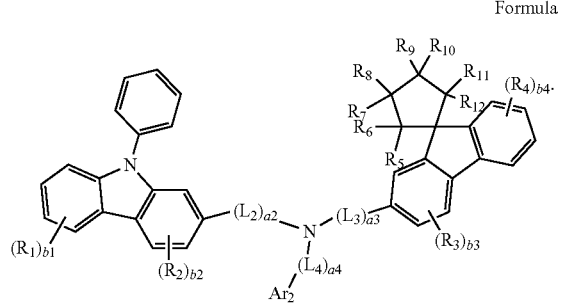

Formula 2

In Formula 2, $L_2$ to $L_4$, $Ar_2$, $R_1$ to $R_{12}$, a2 to a4, and b1 to b4 may each be understood by referring to the corresponding descriptions presented in connection with Formula 1.

In one embodiment, Formula 1 may be represented by Formula 3 below:

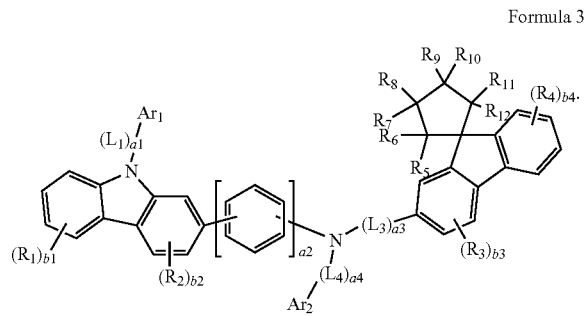

Formula 3

In Formula 3, $L_1$, $L_3$, $L_4$, $Ar_1$, $Ar_2$, $R_1$ to $R_{12}$, a1 to a4, and b1 to b4 may each be understood by referring to the corresponding descriptions presented in connection with Formula 1.

In one embodiment, Formula 1 may be represented by Formula 4 below:

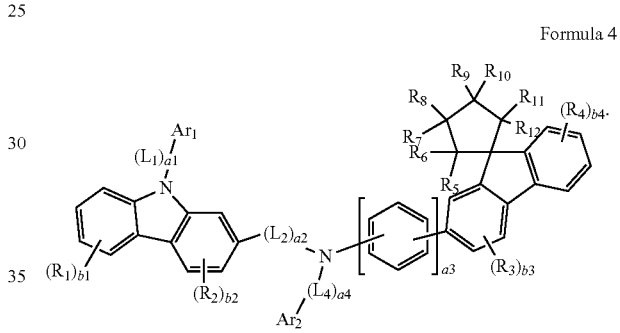

Formula 4

In Formula 4, $L_1$, $L_2$, $L_4$, $Ar_1$, $Ar_2$, $R_1$ to $R_{12}$, a1 to a4, and b1 to b4 may each be understood by referring to the corresponding descriptions presented in connection with Formula 1.

In one embodiment, Formula 1 may be represented by Formula 5 below:

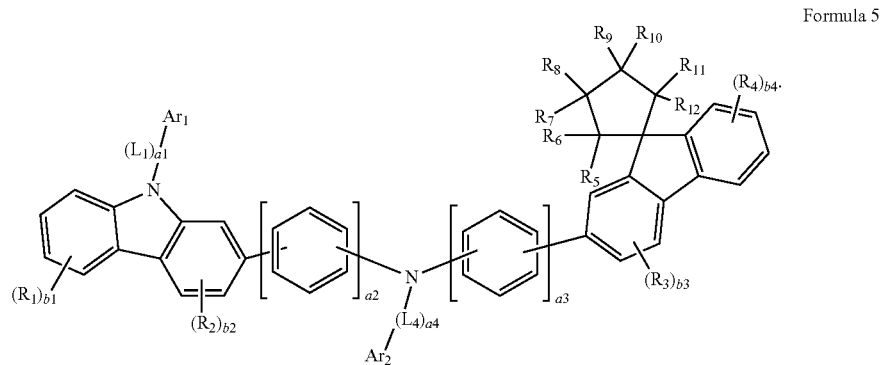

Formula 5

In Formula 5,
$L_1$, $L_4$, $Ar_1$, $Ar_2$, $R_1$ to $R_{12}$, a1 to a4, and b1 to b4 may each be understood by referring to the corresponding descriptions presented in connection with Formula 1.
In one embodiment, the compound represented by Formula 1 may be one of the following compounds:
1
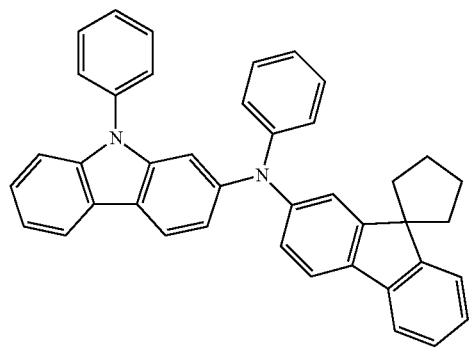
2
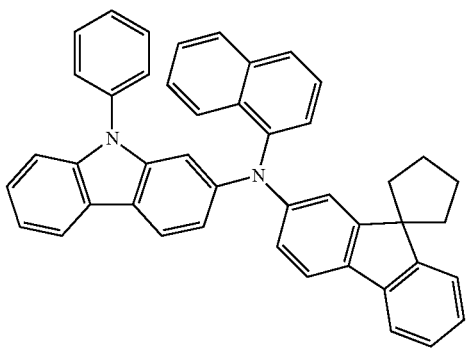
3
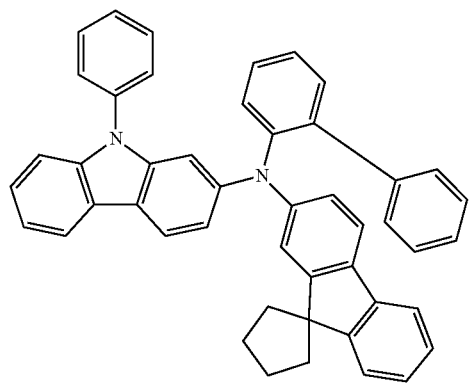
4
5
6
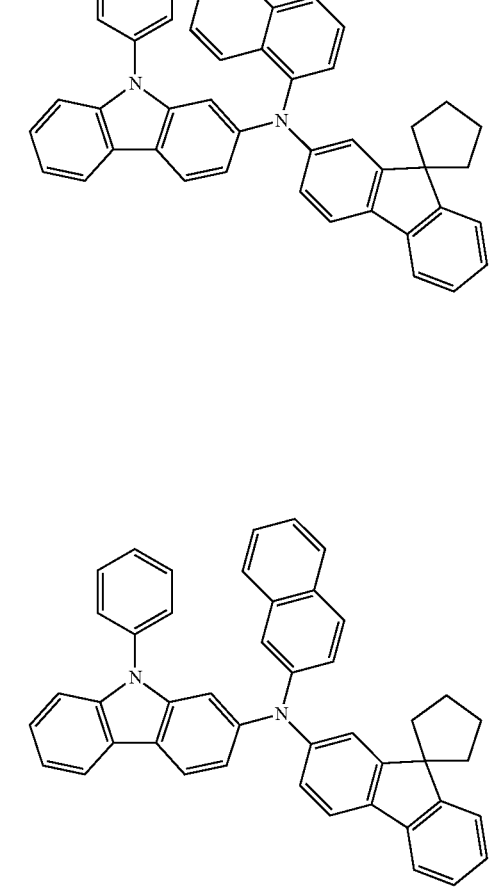
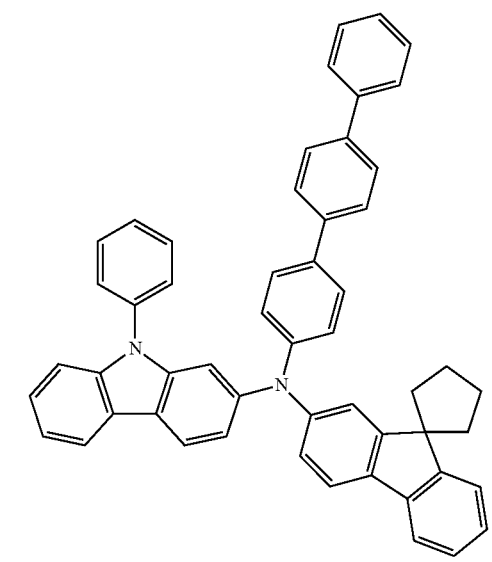

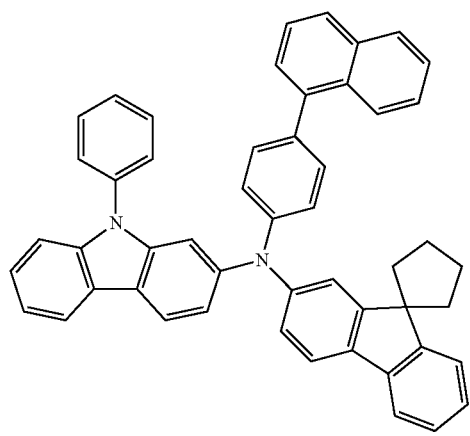
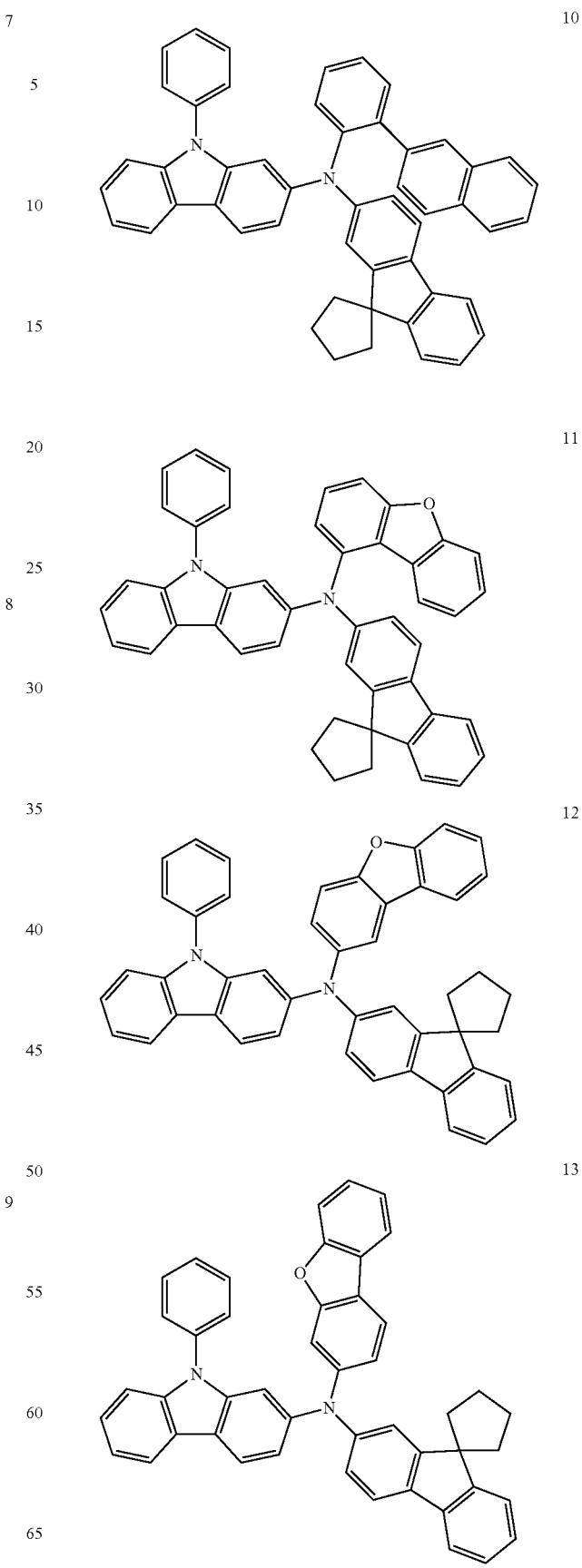

14
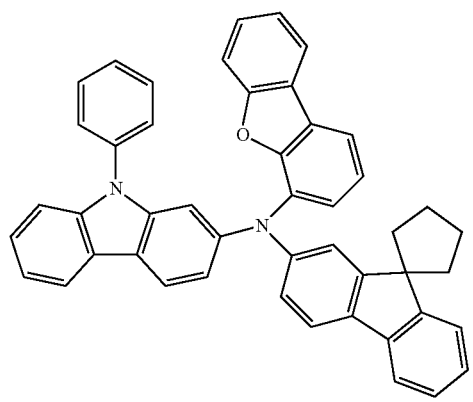
15
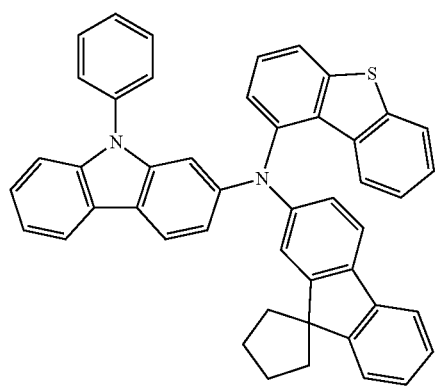
16
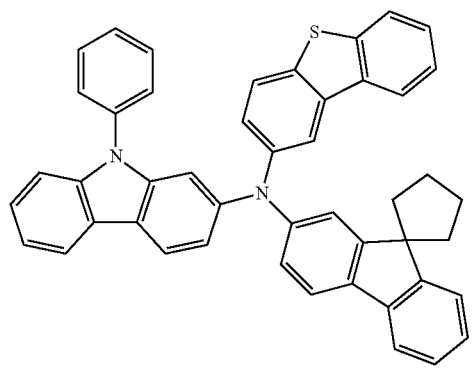
17
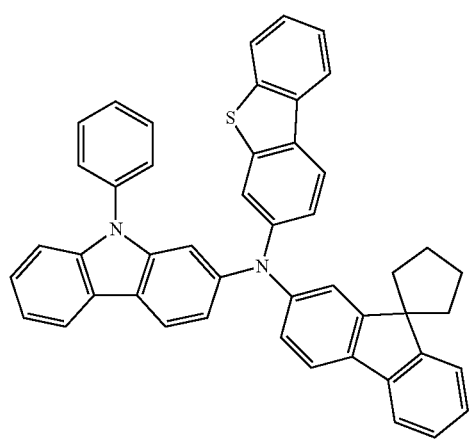
18
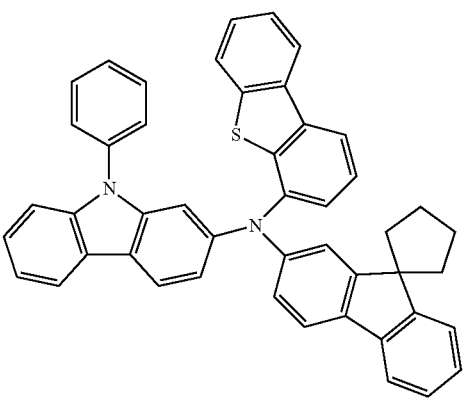
19
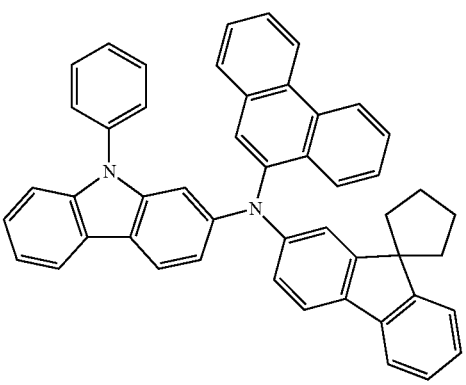
20
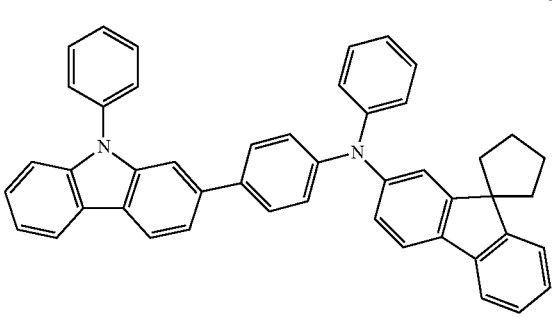
21
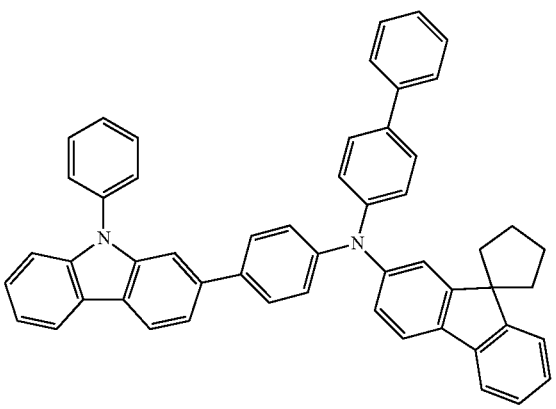

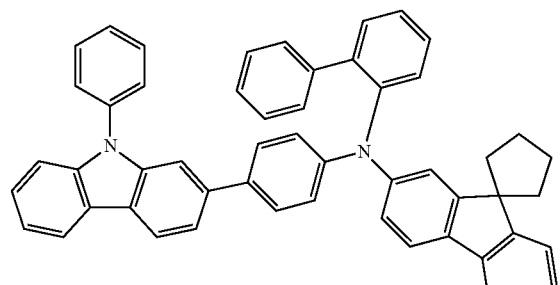
22
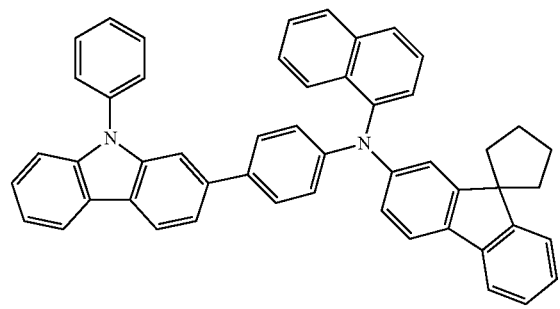
23
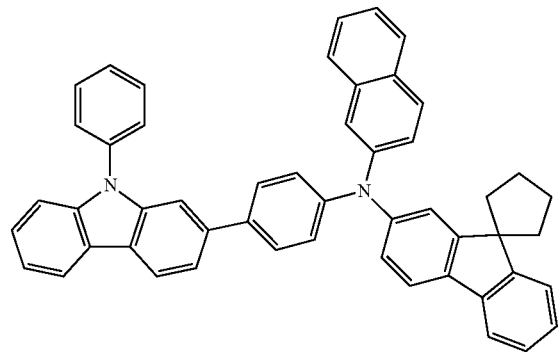
24
25
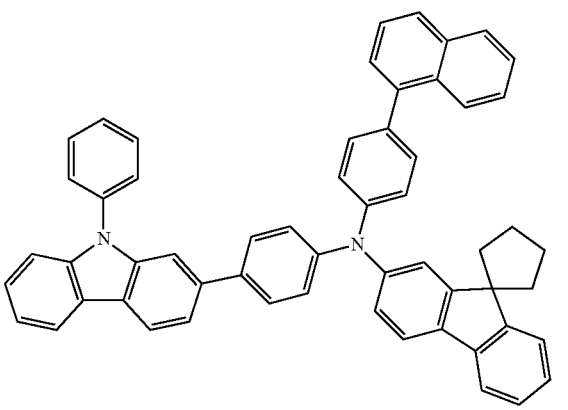
26
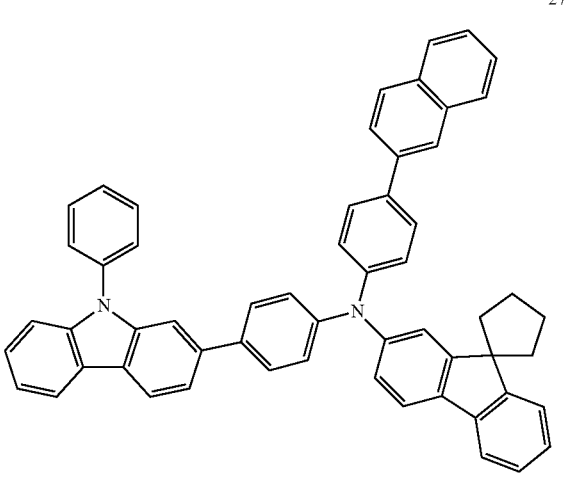
27
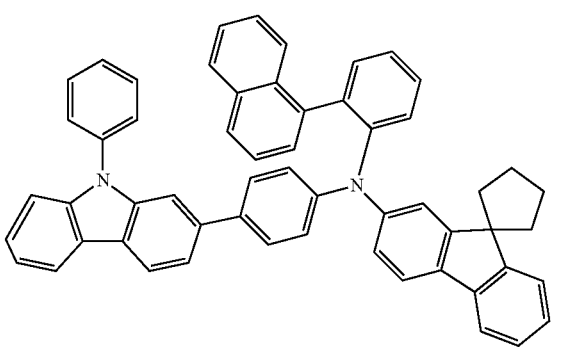
28
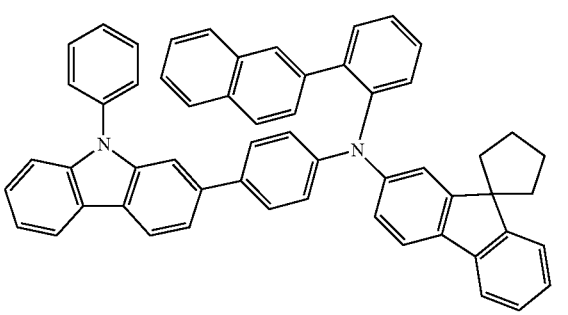
29

30
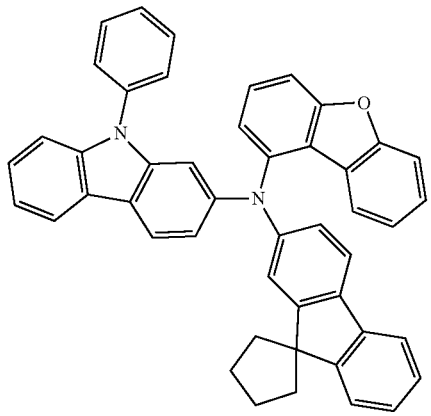
31
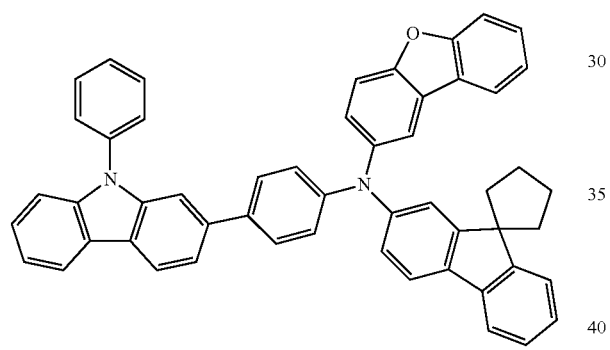
32
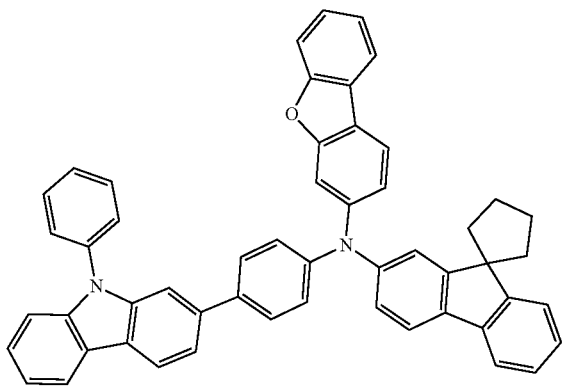
33
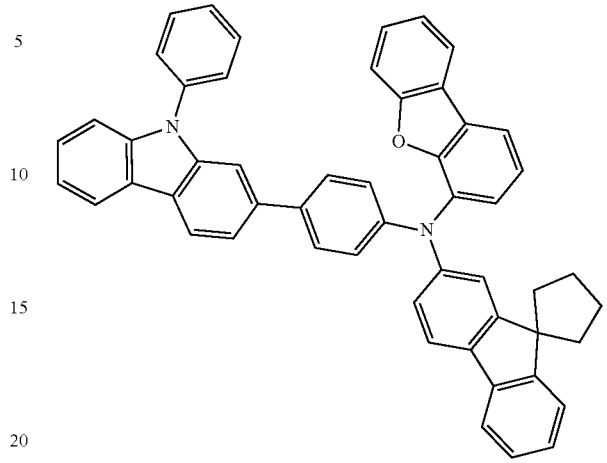
34
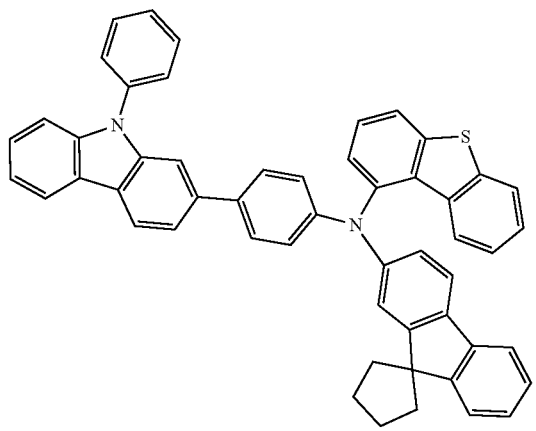
35
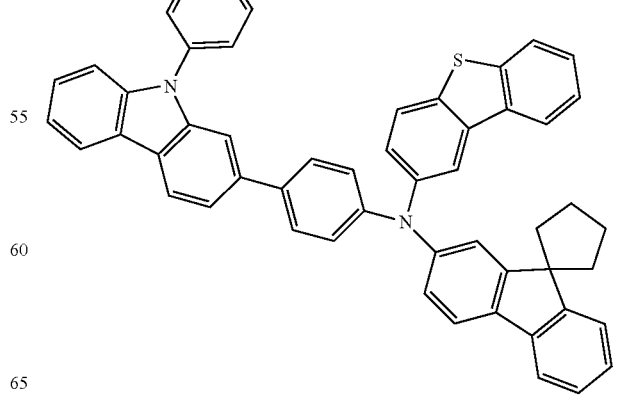

36
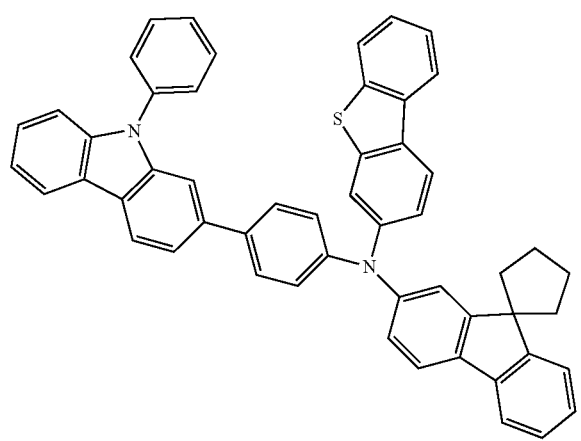
37
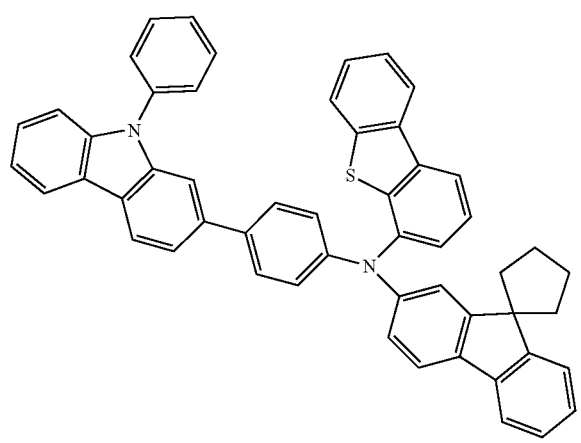
38
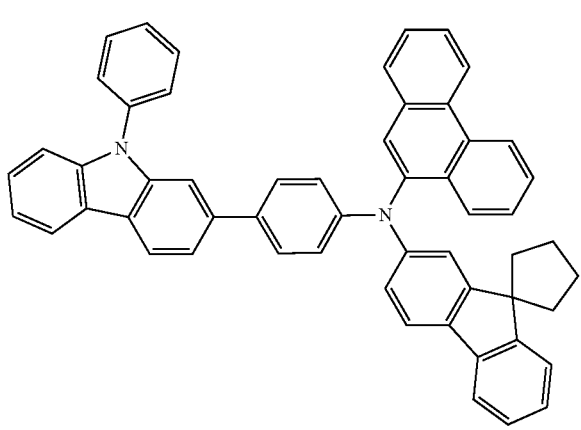
39
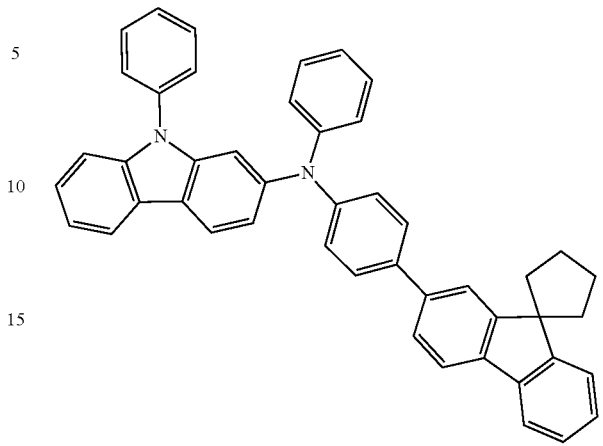
40
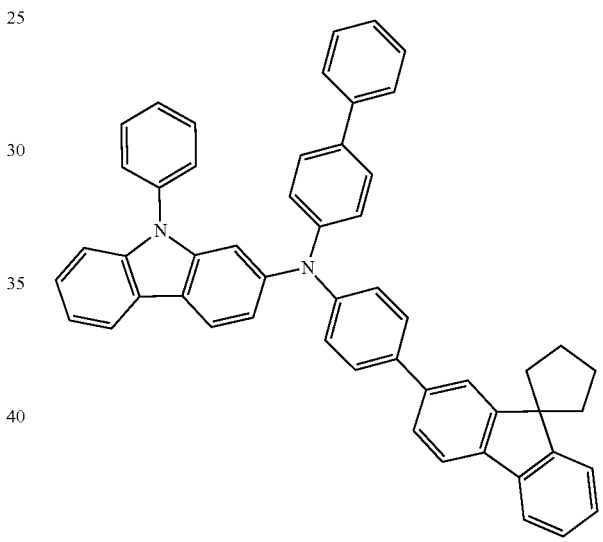
41
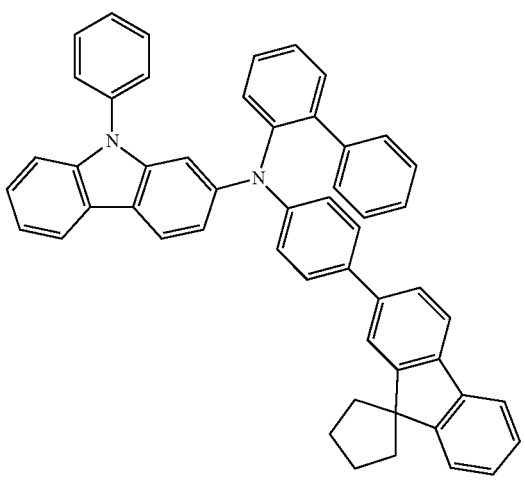

42
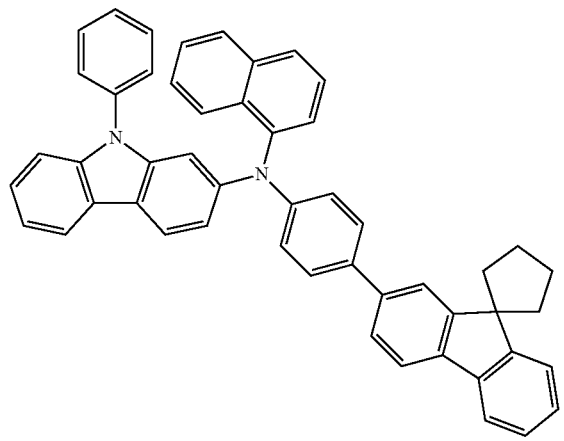
43
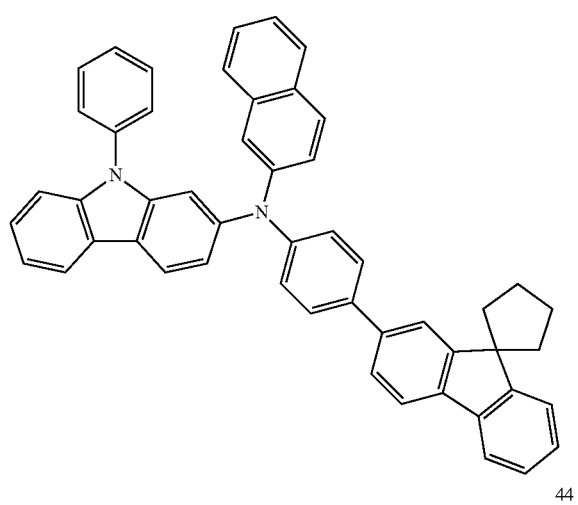
44
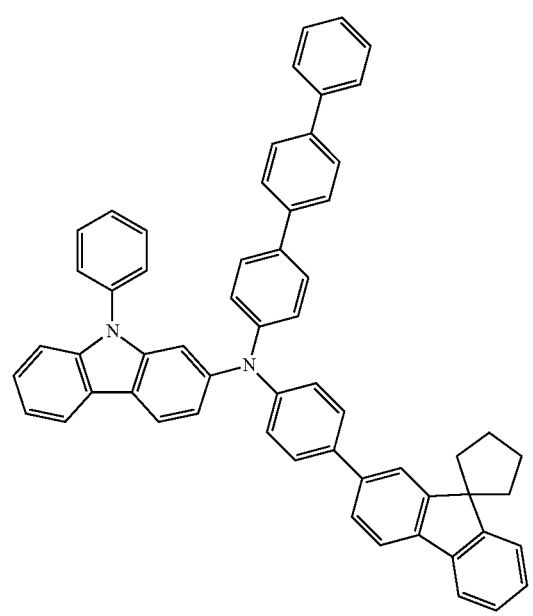
45
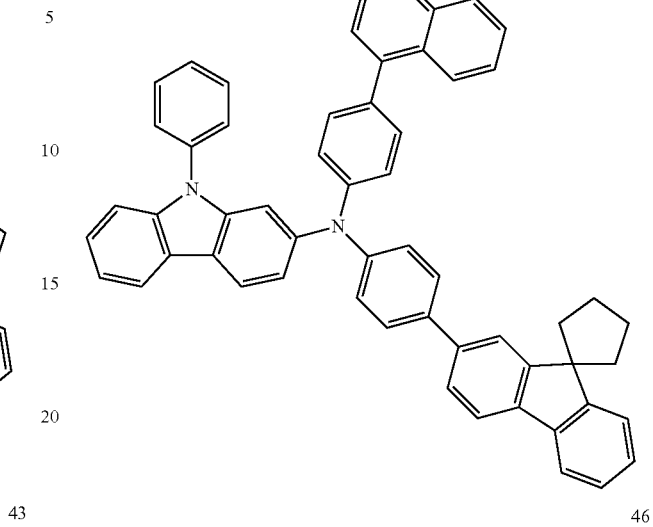
46
47
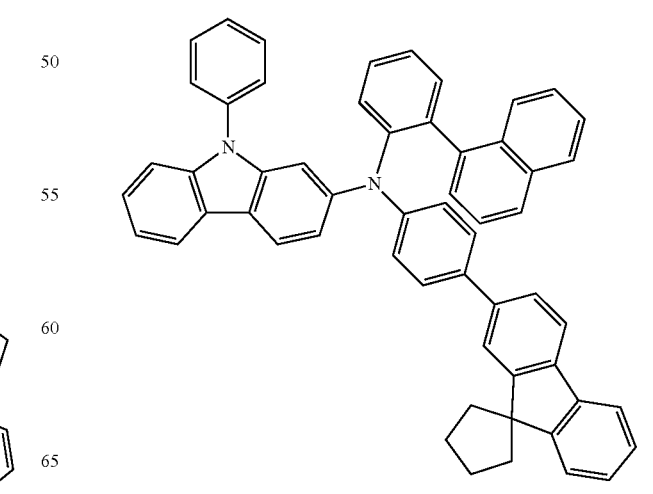

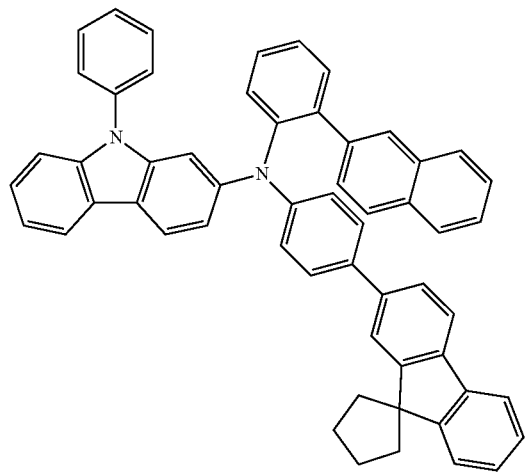
48
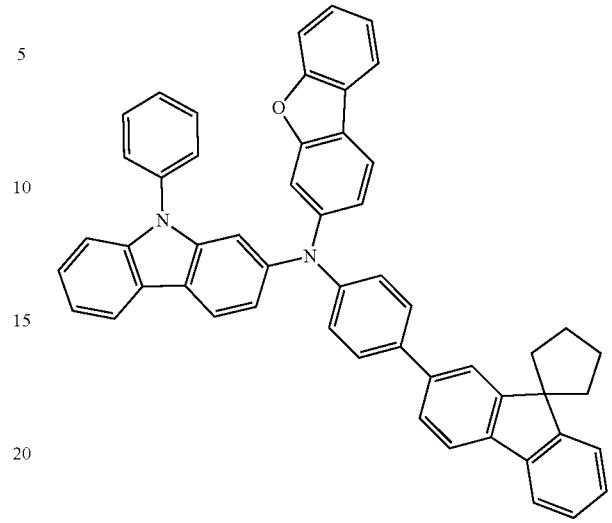
51
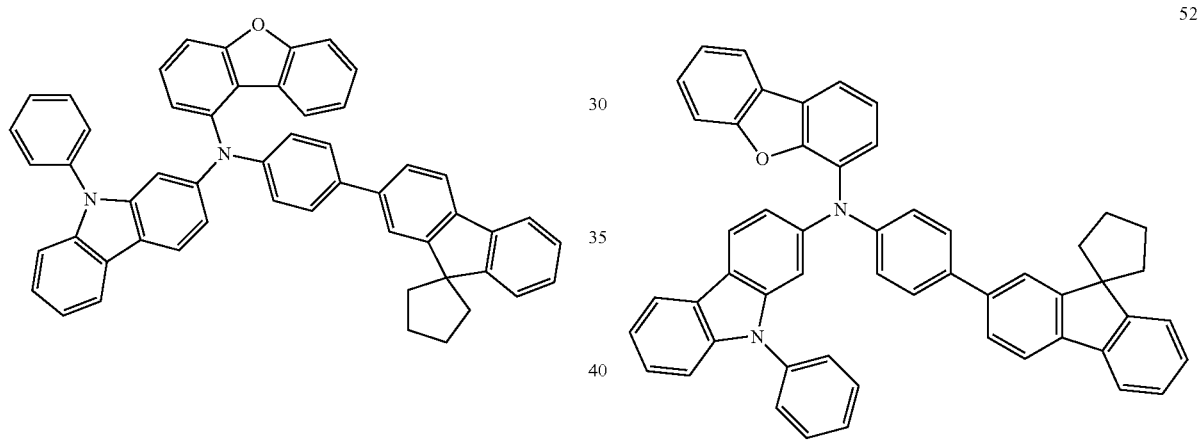
49
52
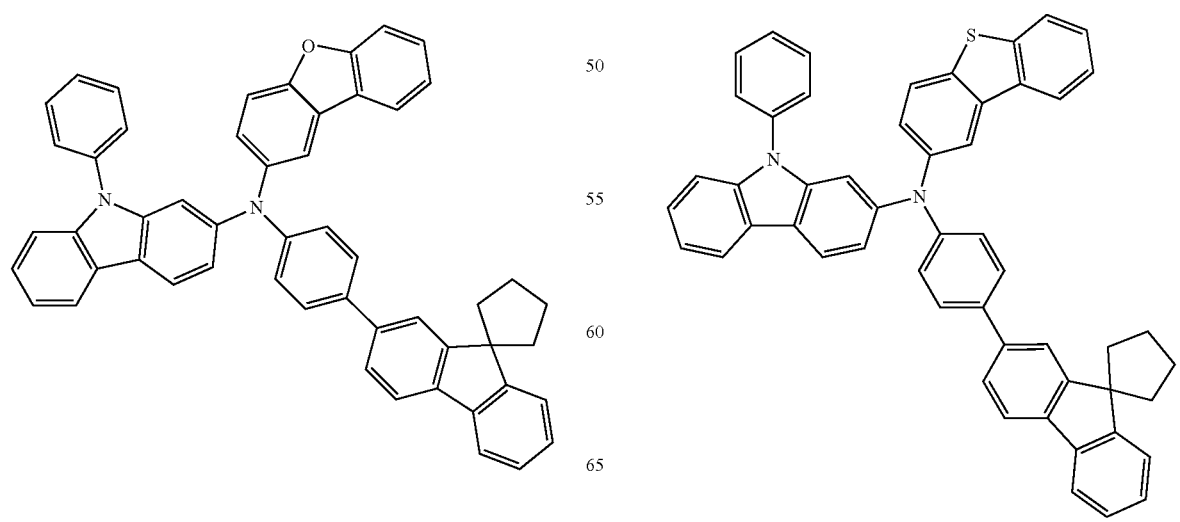
50
54

55
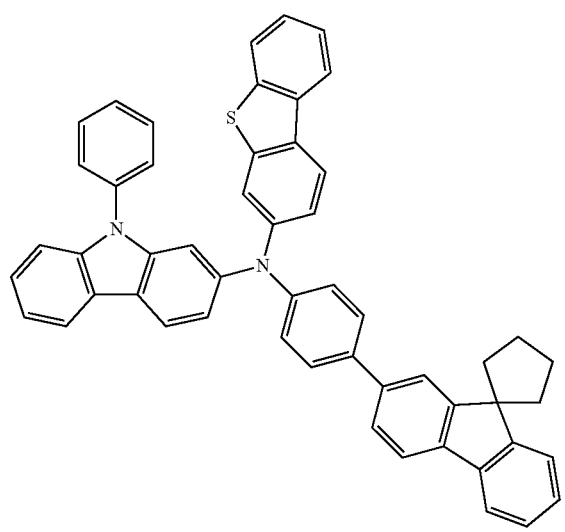
56
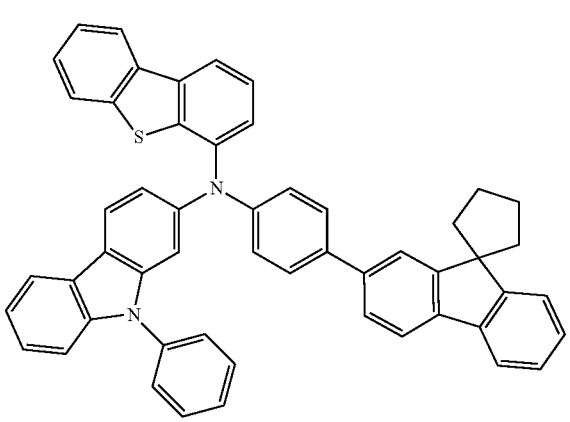
57
58
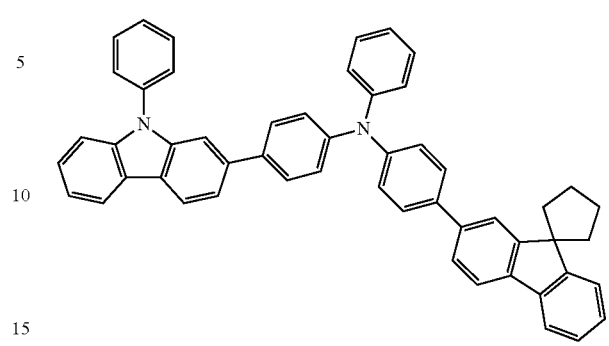
59
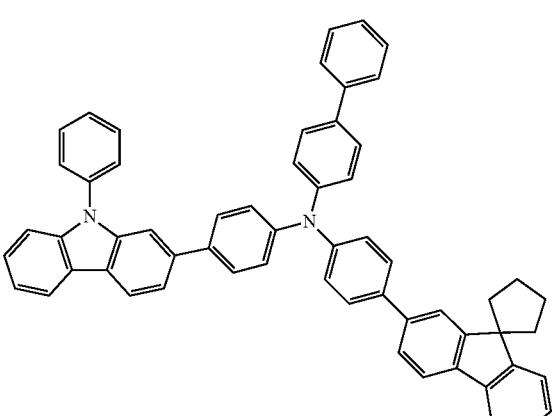
60
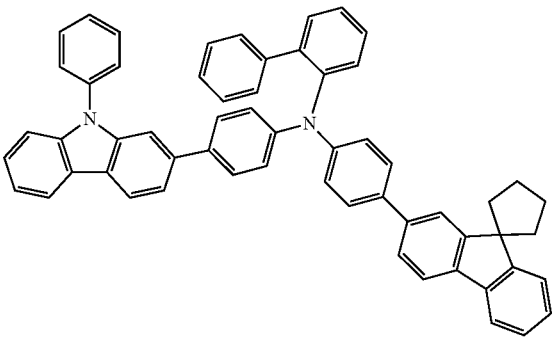
61
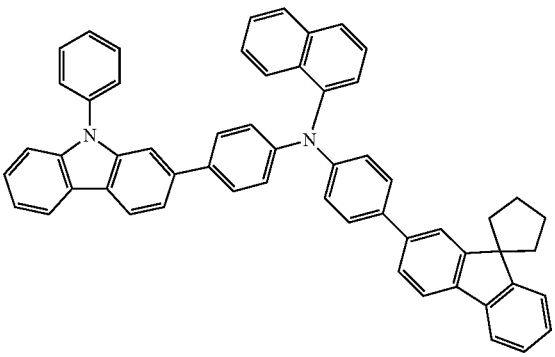

62
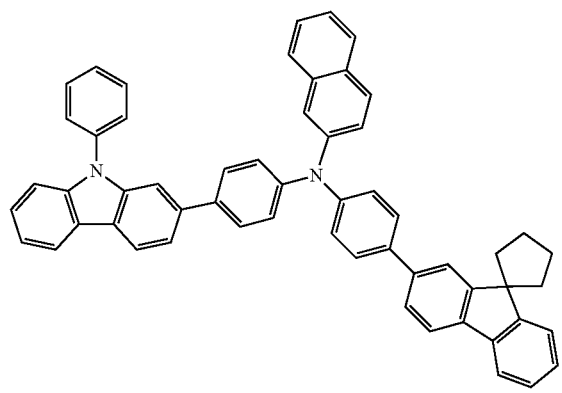
63
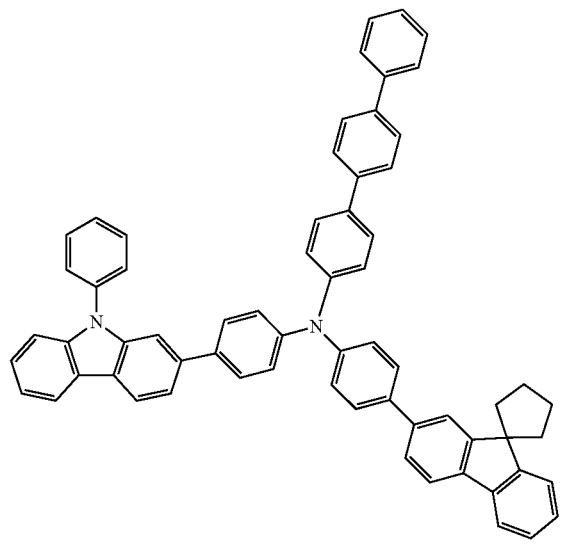
64
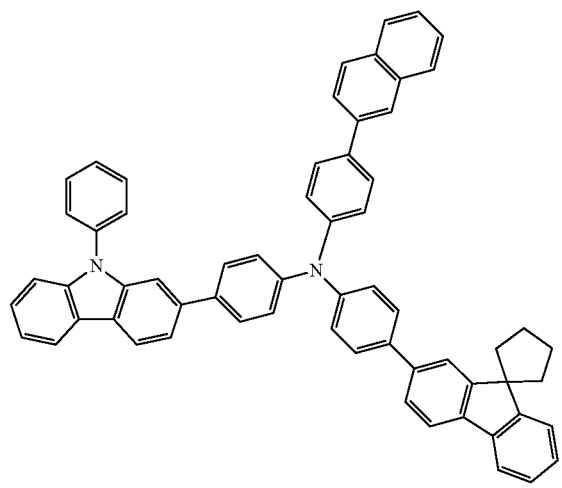
65
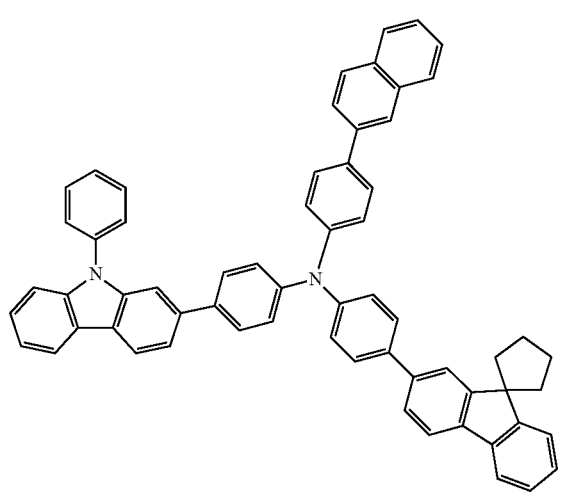
66
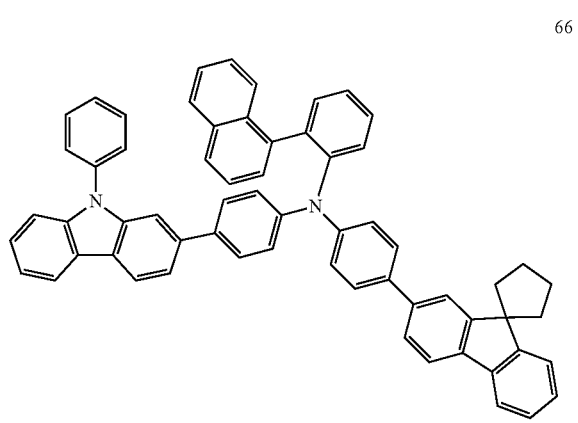
67
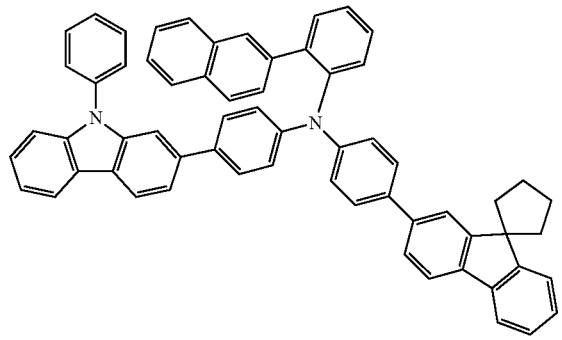

68
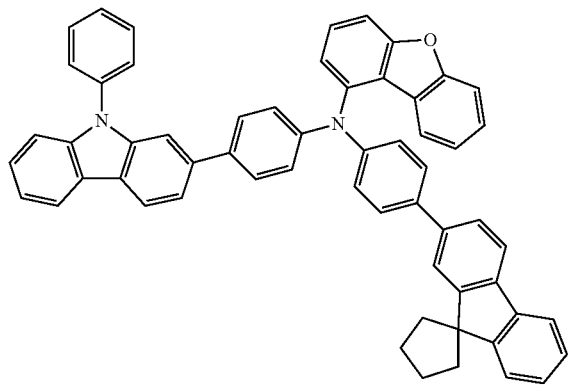
69
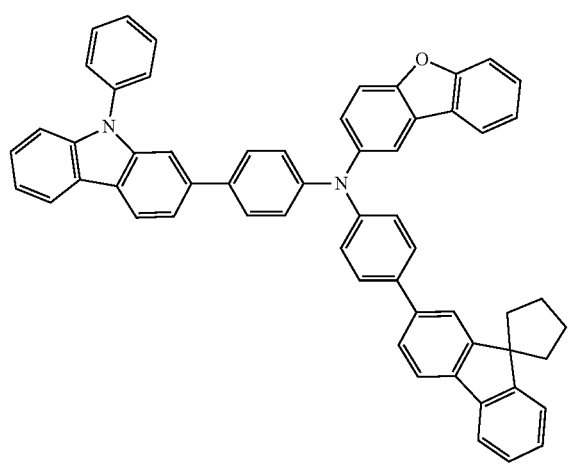
70
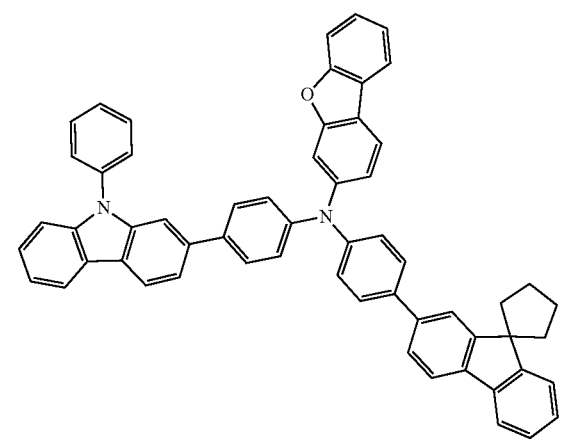
71
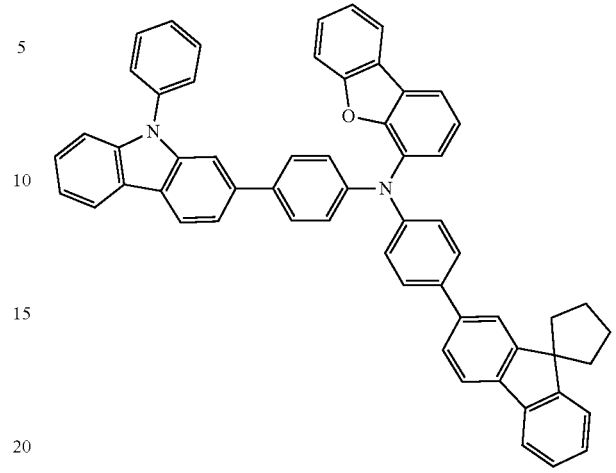
72
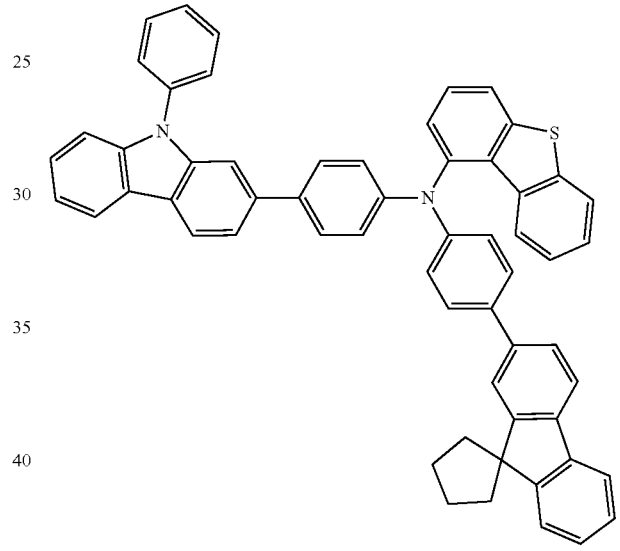
73
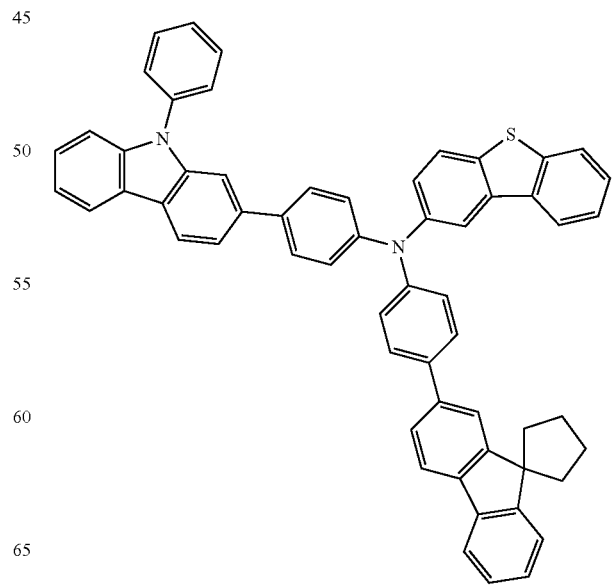

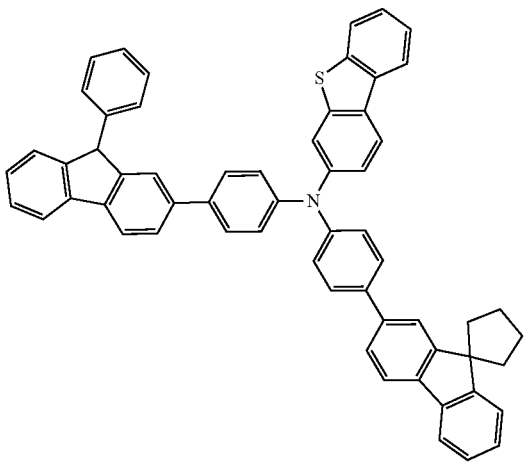

74

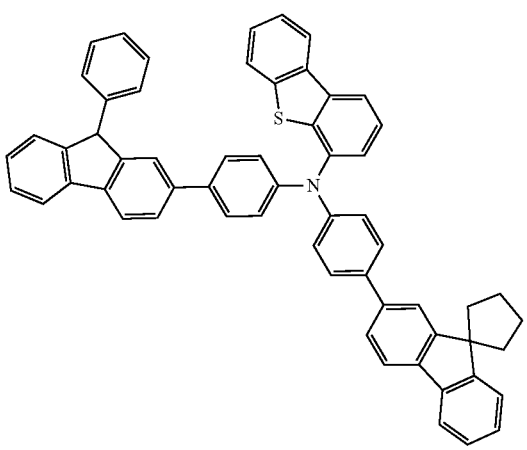

75

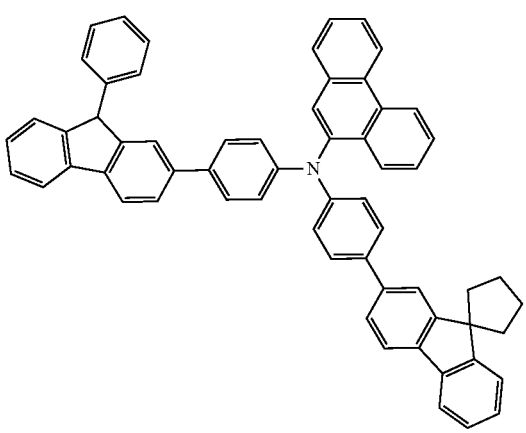

76

The expression "(an organic layer) includes at least one compound" as used herein may include a case in which "(an organic layer) includes one or more identical compounds represented by Formula 1" and a case in which "(an organic layer) includes two or more different compounds represented by Formula 1".

For example, the organic layer may include, as the amine compound (i.e. compound of Formula 1), only Compound 1. In this regard, Compound 1 may exist (e.g., may be included) only in the emission layer of the organic light-emitting device. In one or more embodiments, the organic layer may include, as the amine compound, Compound 1 and Compound 2. In this regard, Compound 1 and Compound 2 may exist in the same layer (for example, Compound 1 and Compound 2 may both exist in an emission layer), or in different layers (for example, Compound 1 may exist in an emission layer and Compound 2 may exist in an electron transport region).

Another embodiment of the present disclosure provides an organic light-emitting device including:
a first electrode;
a second electrode facing the first electrode; and
an organic layer disposed (positioned) between the first electrode and the second electrode and including an emission layer,
wherein the organic layer includes the compound of Formula 1.

In one embodiment,
the first electrode of the organic light-emitting device may be an anode,
the second electrode of the organic light-emitting device may be a cathode, and
the organic layer may further include a hole transport region disposed between the first electrode and the emission layer, and an electron transport region disposed between the emission layer and the second electrode,
the hole transport region may include a hole injection layer, a hole transport layer, a buffer layer, an electron blocking layer, or any combination thereof, and
the electron transport region may include a hole blocking layer, an electron transport layer, an electron injection layer, or any combination thereof.

In one embodiment, the emission layer may be a fluorescent emission layer. For example, the emission layer may be a blue fluorescent emission layer.

In one embodiment, the compound of Formula 1 may be used in a hole transport region, for example, in a hole transport layer.

Another embodiment of the present disclosure provides an electronic apparatus including: a thin-film transistor; and the organic light-emitting device, wherein the thin-film transistor includes a source electrode, a drain electrode, an activation layer, and a gate electrode, and the first electrode of the organic light-emitting device may be in electrical connection with one of the source electrode or the drain electrode of the thin-film transistor.

The term "an organic layer" as used herein refers to a single layer and/or a plurality of layers disposed between the first electrode and the second electrode of an organic light-emitting device. A material included in the "organic layer" is not limited to an organic material.

Description of FIG. 1

Figure 1:
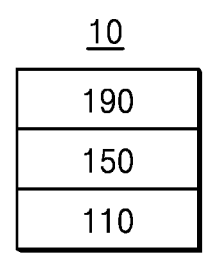

FIG. 1 is a schematic cross-sectional view of an organic light-emitting device 10 according to an embodiment. The organic light-emitting device 10 includes a first electrode 110, an organic layer 150, and a second electrode 190.

Hereinafter, the structure of the organic light-emitting device 10 according to an embodiment and a method of manufacturing the organic light-emitting device 10 will be described in connection with FIG. 1.

First Electrode 110

In FIG. 1, a substrate may be additionally disposed under the first electrode 110 or above the second electrode 190. The substrate may be a glass substrate and/or a plastic substrate, each having excellent mechanical strength, thermal stability, transparency, surface smoothness, ease of handling, and/or water resistance.

The first electrode 110 may be formed by depositing or sputtering a material to form the first electrode 110 on the substrate. When the first electrode 110 is an anode, the material to form the first electrode 110 may be selected from materials with a high work function to facilitate hole injection.

The first electrode 110 may be a reflective electrode, a semi-reflective electrode, or a transmissive electrode. When the first electrode 110 is a transmissive electrode, a material to form the first electrode may be selected from indium tin oxide (ITO), indium zinc oxide (IZO), tin oxide ($SnO_2$), zinc oxide (ZnO), and any combinations thereof, but embodiments of the present disclosure are not limited thereto. In one or more embodiments, when the first electrode 110 is a semi-transmissive electrode or a reflective electrode, a material to form the first electrode 110 may be selected from magnesium (Mg), silver (Ag), aluminum (Al), aluminum-lithium (Al—Li), calcium (Ca), magnesium-indium (Mg—In), magnesium-silver (Mg—Ag), and any combinations thereof, but embodiments of the present disclosure are not limited thereto.

The first electrode 110 may have a single-layered structure, or a multi-layered structure including two or more layers. For example, the first electrode 110 may have a three-layered structure of ITO/Ag/ITO, but the structure of the first electrode 110 is not limited thereto.

Organic Layer 150

The organic layer 150 may be disposed on the first electrode 110. The organic layer 150 may include an emission layer.

The organic layer 150 may further include a hole transport region between the first electrode 110 and the emission layer, and an electron transport region between the emission layer and the second electrode 190.

Hole Transport Region in Organic Layer 150

The hole transport region may have i) a single-layered structure including a single layer including a single material, ii) a single-layered structure including a single layer including a plurality of different materials, or iii) a multi-layered structure having a plurality of layers including a plurality of different materials.

The hole transport region may include at least one layer selected from a hole injection layer, a hole transport layer, an emission auxiliary layer, and an electron blocking layer.

For example, the hole transport region may have a single-layered structure including a single layer including a plurality of different materials, or a multi-layered structure having a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein for each structure, constituting layers are sequentially stacked from the first electrode 110 in this stated order, but the structure of the hole transport region is not limited thereto.

The hole transport region may include the organic layer including the compound represented by Formula 1.

The hole transport region may further include, in addition to the compound represented by Formula 1, for example, any of the following compounds described below.

In one embodiment, the hole transport region may include at least one selected from m-MTDATA, TDATA, 2-TNATA, NPB(NPD), β-NPB, TPD, spiro-TPD, spiro-NPB, methylated NPB, TAPC, HMTPD, 4,4',4"-tris(N-carbazolyl)triphenylamine (TCTA), polyaniline/dodecylbenzenesulfonic acid (PAN I/DBSA), poly(3,4-ethylenedioxythiophene)/poly(4-styrenesulfonate) (PEDOT/PSS), polyaniline/camphor sulfonic acid (PANI/CSA), and polyaniline/poly(4-styrenesulfonate) (PAN I/PSS):

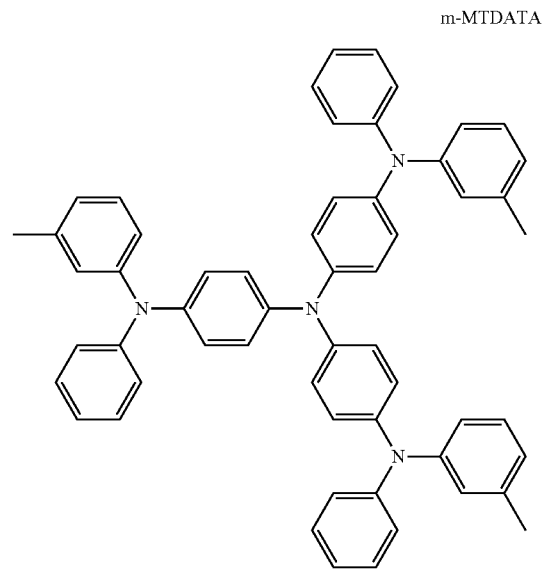

m-MTDATA

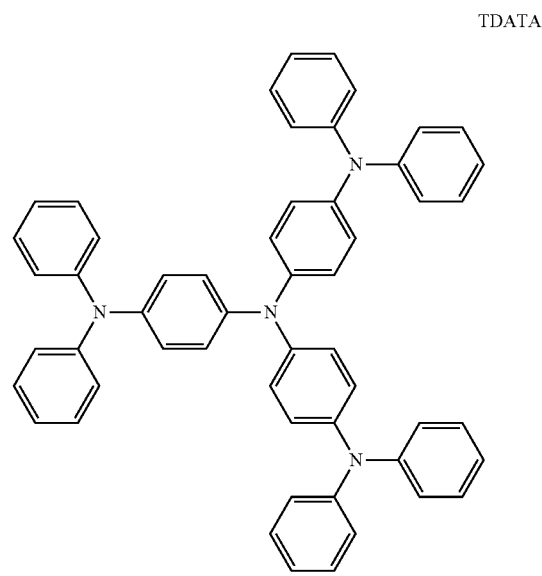

TDATA

2-TNATA
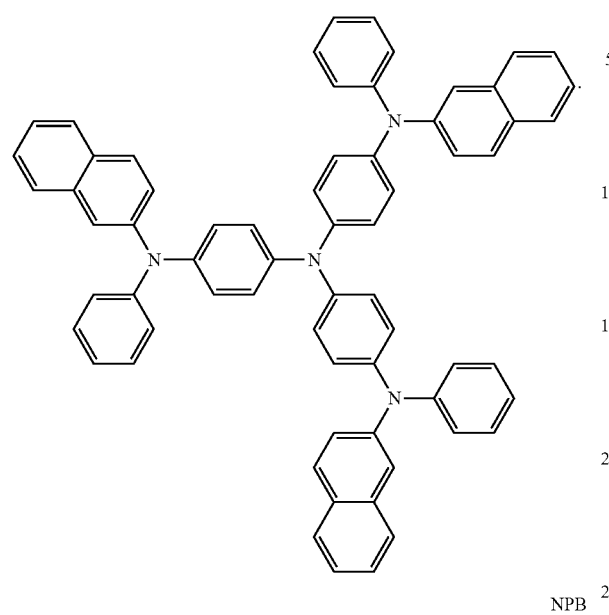
NPB
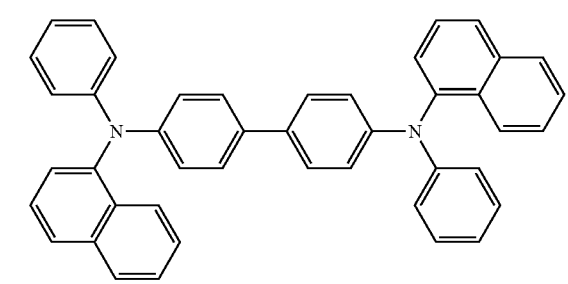
β-NPB
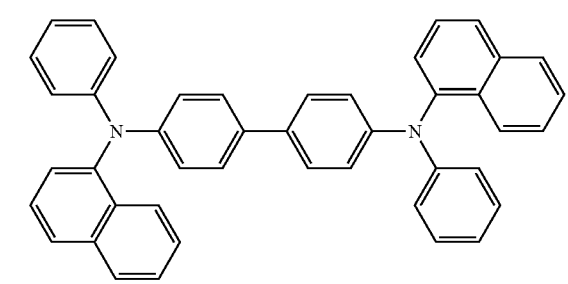
TPD
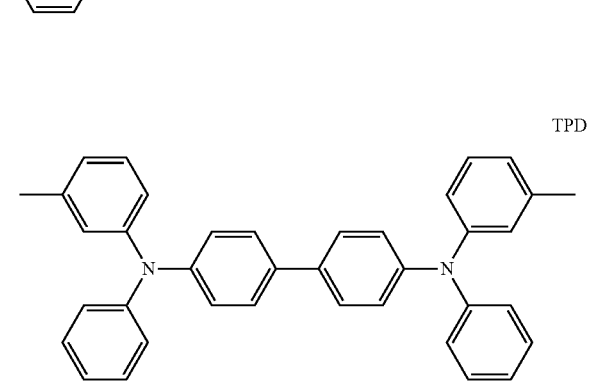
Spiro-TPD
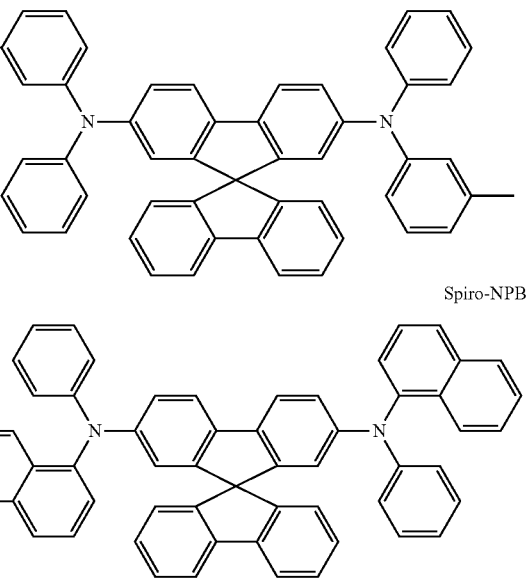
Spiro-NPB
methylated NPB
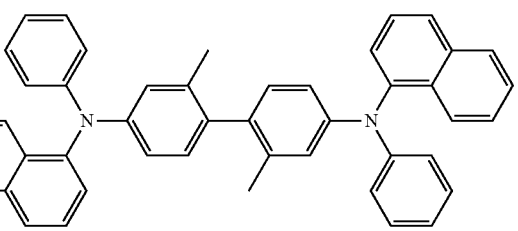
TAPC
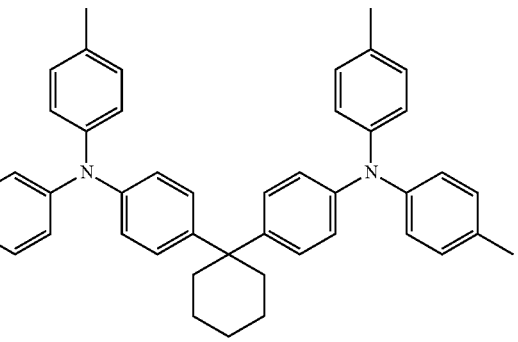
HMTPD
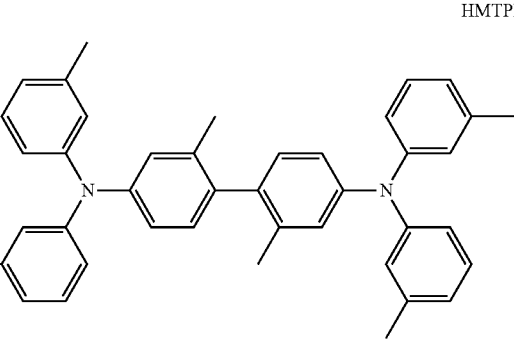
A thickness of the hole transport region may be in a range of about 100 Å to about 10,000 Å, for example, about 100 Å to about 1,000 Å. When the hole transport region includes at least one selected from a hole injection layer and a hole transport layer, the thickness of the hole injection layer may be in a range of about 100 Å to about 9,000 Å, and for example, about 100 Å to about 1,000 Å, and the thickness of the hole transport layer may be in a range of about 50 Å to about 2,000 Å, and for example, about 100 Å to about 1,500 Å. When the thicknesses of the hole transport region, the hole injection layer, and the hole transport layer are within any of these ranges, satisfactory (or suitable) hole transporting characteristics may be obtained without a substantial increase in driving voltage.

The emission auxiliary layer may increase a light-emission efficiency by compensating for an optical resonance distance according to the wavelength of light emitted by an emission layer, and the electron blocking layer may block or reduce the flow of electrons from an electron transport region. The emission auxiliary layer and the electron blocking layer may each independently include any of the materials as described above.

p-Dopant

The hole transport region may further include, in addition to the materials described above, a charge-generation material for the improvement of conductive properties. The charge-generation material may be homogeneously or non-homogeneously dispersed in the hole transport region.

The charge-generation material may be, for example, a p-dopant.

In one embodiment, the p-dopant may have a lowest unoccupied molecular orbital (LUMO) energy level of −3.5 eV or less.

The p-dopant may include at least one selected from a quinone derivative, a metal oxide, and a cyano group-containing compound, but embodiments of the present disclosure are not limited thereto.

In one embodiment, the p-dopant may include at least one selected from:

a quinone derivative, such as tetracyanoquinodimethane (TCNQ) and/or 2,3,5,6-tetrafluoro-7,7,8,8-tetracyanoquinodimethane (F4-TCNQ);

a metal oxide, such as tungsten oxide and/or molybdenum oxide;

1,4,5,8,9,12-hexaazatriphenylene-hexacarbonitrile (HAT-CN); and a compound represented by Formula 221 below, but embodiments of the present disclosure are not limited thereto:

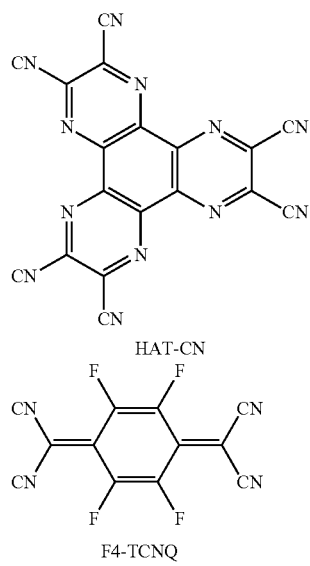

HAT-CN

F4-TCNQ

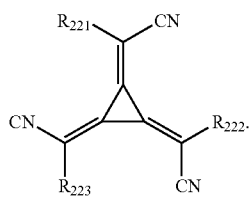

Formula 221

In Formula 221, $R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, wherein at least one selected from $R_{221}$ to $R_{223}$ may have at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I, Emission Layer in Organic Layer 150

When the organic light-emitting device 10 is a full-color organic light-emitting device, the emission layer may be patterned into a red emission layer, a green emission layer, or a blue emission layer, according to a sub-pixel. In one or more embodiments, the emission layer may have a stacked structure of two or more layers selected from a red emission layer, a green emission layer, and a blue emission layer, in which the two or more layers contact each other or are separated from each other. In one or more embodiments, the emission layer may include two or more materials selected from a red light-emitting material, a green light-emitting material, and a blue light-emitting material, in which the two or more materials are mixed with each other in a single layer to emit white light.

The emission layer may include a host and a dopant. The dopant may include at least one selected from a phosphorescence dopant and a fluorescence dopant.

In the emission layer, an amount of the dopant may be in a range of about 0.01 parts by weight to about 15 parts by weight, based on 100 parts by weight of the host, but embodiments of the present disclosure are not limited thereto.

A thickness of the emission layer may be in a range of about 100 Å to about 1,000 Å, for example, about 200 Å to about 600 Å. When the thickness of the emission layer is within this range, excellent (or suitable) light-emission characteristics may be obtained without a substantial increase in driving voltage.

The emission layer may include a host.

Host in Emission Layer

In one or more embodiments, the host may include a compound represented by Formula 301 below:

$[Ar_{301}]_{xb11}-[(L_{301})_{xb1}-R_{301}]_{xb21}$.  Formula 301

In Formula 301,

Ar$_{301}$ may be a substituted or unsubstituted C$_4$-C$_{60}$ carbocyclic group or a substituted or unsubstituted C$_1$-C$_{60}$ heterocyclic group, xb11 may be 1, 2, or 3, L$_{301}$ may be selected from a substituted or unsubstituted C$_3$-C$_{10}$ cycloalkylene group, a substituted or unsubstituted C$_1$-C$_{10}$ heterocycloalkylene group, a substituted or unsubstituted C$_3$-C$_{10}$ cycloalkenylene group, a substituted or unsubstituted C$_1$-C$_{10}$ heterocycloalkenylene group, a substituted or unsubstituted C$_6$-C$_{60}$ arylene group, a substituted or unsubstituted C$_1$-C$_{60}$ heteroarylene group, a substituted or unsubstituted divalent non-aromatic condensed polycyclic group, and a substituted or unsubstituted divalent non-aromatic condensed heteropolycyclic group, xb11 may be 1, 2, or 3, R$_{301}$ may be selected from deuterium, —F, —Cl, —Br, —I, a hydroxyl group, a cyano group, a nitro group, an amidino group, a hydrazino group, a hydrazono group, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, a substituted or unsubstituted monovalent non-aromatic condensed heteropolycyclic group, —Si(Q$_{301}$)(Q$_{302}$)(Q$_{303}$), —N(Q$_{301}$)(Q$_{302}$), —B(Q$_{301}$)(Q$_{302}$), —C(=O)(Q$_{301}$), —S(=O)$_2$(Q$_{301}$), and —P(=O)(Q$_{301}$)(Q$_{302}$), xb21 may be an integer from 1 to 5, and Q$_{301}$ to Q$_{303}$ may each independently be selected from a C$_1$-C$_{10}$ alkyl group, a C$_1$-C$_{10}$ alkoxy group, a phenyl group, a biphenyl group, a terphenyl group, and a naphthyl group, but embodiments of the present disclosure are not limited thereto.

In one embodiment, Ar$_{301}$ in Formula 301 may be selected from:

a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a C$_1$-C$_{20}$ alkyl group, a C$_1$-C$_{20}$ alkoxy group, a phenyl group, a biphenyl group, a terphenyl group, a naphthyl group, —Si(Q$_{31}$)(Q$_{32}$)(Q$_{33}$), —N(Q$_{31}$)(Q$_{32}$), —B(Q$_{31}$)(Q$_{32}$), —C(=O)(Q$_{31}$), —S(=O)$_2$(Q$_{31}$), and —P(=O)(Q$_{31}$)(Q$_{32}$), and Q$_{31}$ to Q$_{33}$ may each independently be selected from a C$_1$-C$_{10}$ alkyl group, a C$_1$-C$_{10}$ alkoxy group, a phenyl group, a biphenyl group, a terphenyl group, and a naphthyl group, but embodiments of the present disclosure are not limited thereto.

When xb11 in Formula 301 is 2 or more, two or more Ar$_{301}$(s) may be linked via a single bond.

In one or more embodiments, the compound represented by Formula 301 may be represented by Formula 301-1 or Formula 301-2 below:

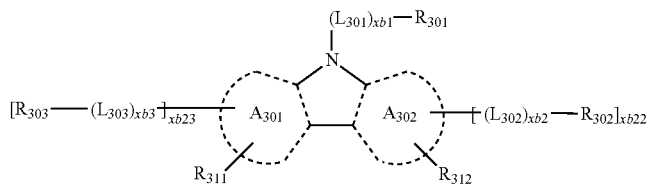

Formula 301-1

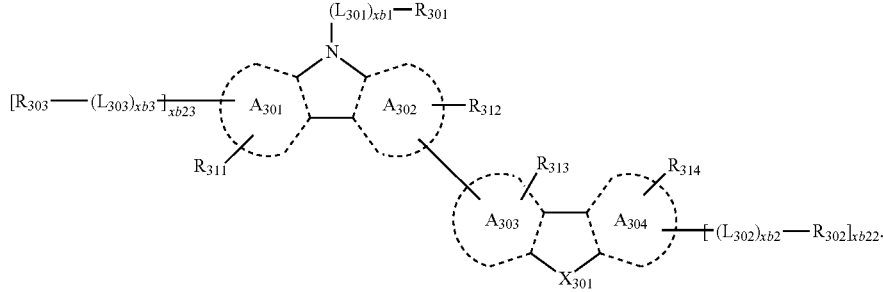

Formula 301-2

In Formulae 301-1 and 301-2, ring A$_{301}$ to ring A$_{304}$ may each independently be a benzene ring, a naphthalene ring, a phenanthrene ring, a fluoranthene ring, a triphenylene ring, a pyrene ring, a chrysene ring, a pyridine ring, a pyrimidine ring, an indene ring, a fluorene ring, a spiro-bifluorene ring, a benzofluorene ring, a dibenzofluorene ring, an indole ring, a carbazole ring, a benzocarbazole ring, a dibenzocarbazole ring, a furan ring, a benzofuran ring, a dibenzofuran ring, a naphthofuran ring, a benzonaphthofuran ring, a dinaphthofuran ring, a thiophene ring, a benzothiophene ring, a dibenzothiophene ring, a naphthothiophene ring, a benzonaphthothiophene ring, and/or a dinaphthothiophene ring, $X_{301}$ may be O, S, and/or N-$[(L_{304})_{xb4}$-$R_{304}]$, $R_{311}$ to $R_{314}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$, xb22 and xb23 may each independently be 0, 1, and/or 2, $L_{301}$, xb1, $R_{301}$, and $Q_{31}$ to $Q_{33}$ may each be understood by referring to the corresponding descriptions presented herein, $L_{302}$ to $L_{304}$ may each independently be the same as described in connection with $L_{301}$, xb2 to xb4 may each independently be the same as described in connection with xb1, and $R_{302}$ to $R_{304}$ may each independently be the same as described in connection with $R_{301}$.

For example, $L_{301}$ to $L_{304}$ in Formulae 301, 301-1, and 301-2 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$, and $Q_{31}$ to $Q_{33}$ are the same as described above.

In one embodiment, $R_{301}$ to $R_{304}$ in Formulae 301, 301-1, and 301-2 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ are the same as described above.

In one or more embodiments, the host may include an alkaline earth metal complex. For example, the host may be selected from a Be complex (for example, Compound H55), a Mg complex, and a Zn complex.

The host may include at least one selected from 9,10-di (2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazoyl)-1,1'-biphenyl (CBP), 1,3-di-9-carbazolylbenzene (mCP), 1,3,5-tri(carbazol-9-yl)benzene (TCP), and Compounds H1 to H55 below, but embodiments of the present disclosure are not limited thereto:

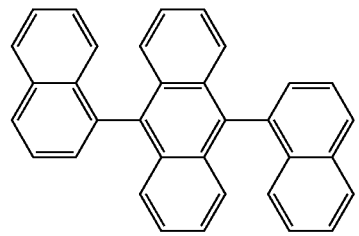

H1

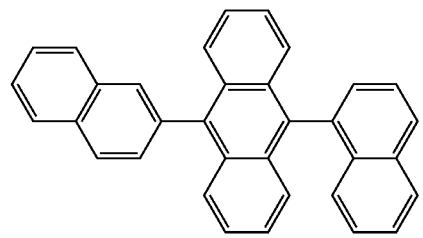

H2

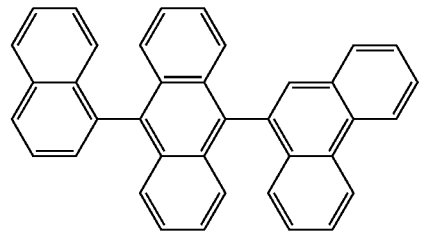

H3

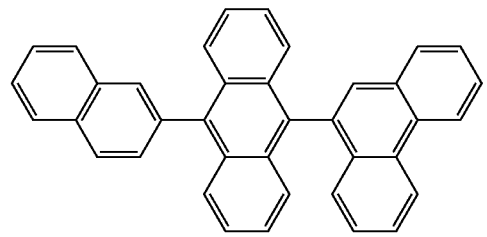

H4

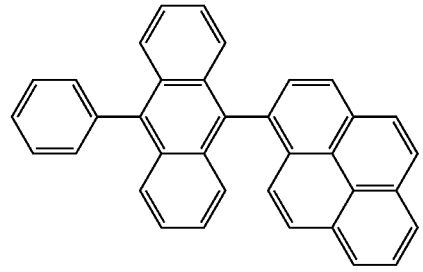

H5

H6
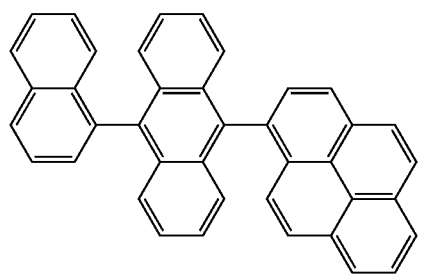
H7
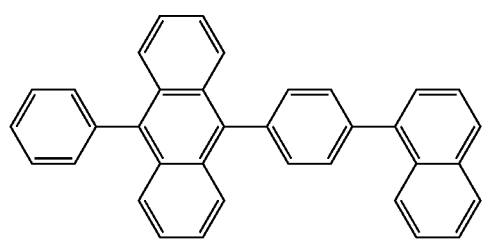
H8
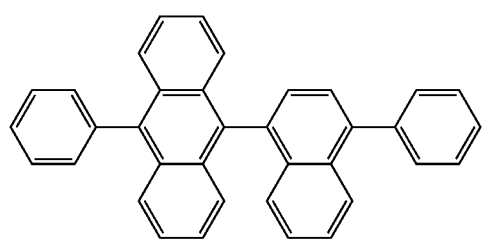
H9
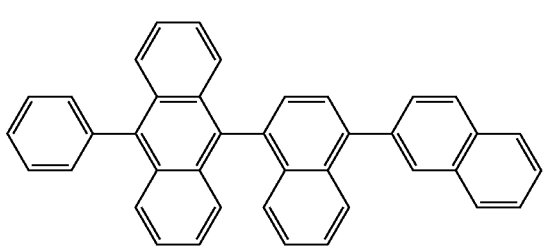
H10
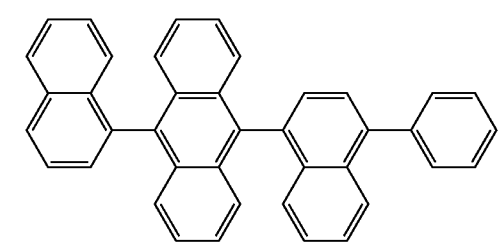
H11
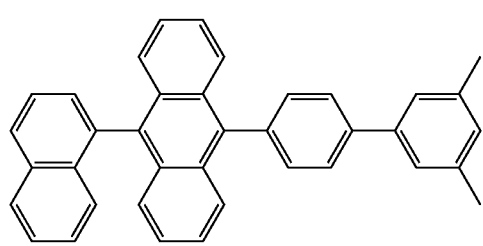
H12
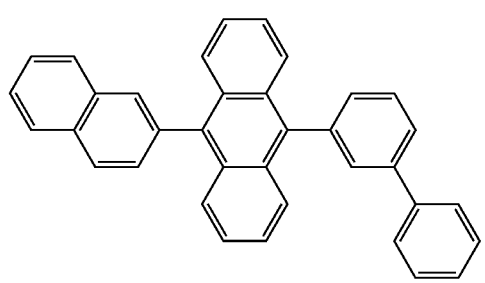
H13
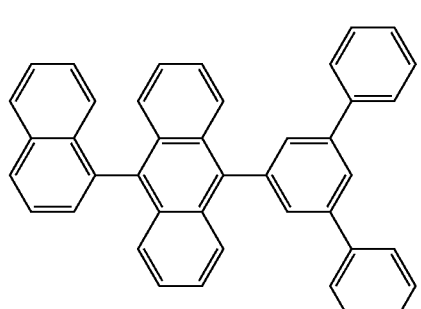
H14
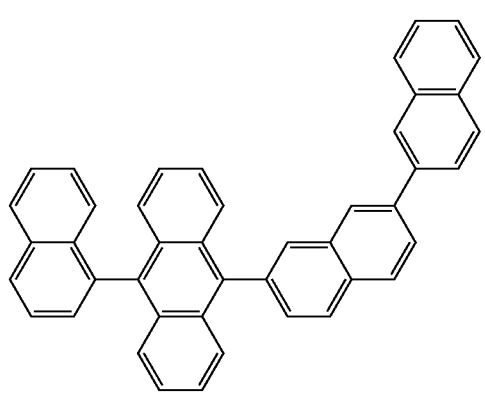
H15
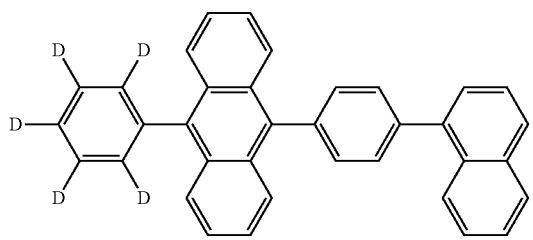
H16
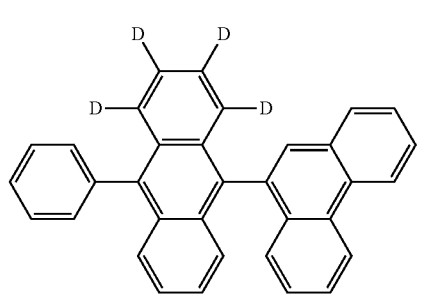

H17
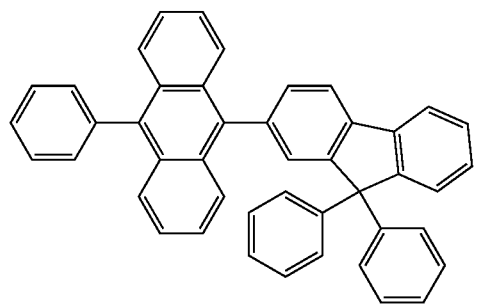
H18
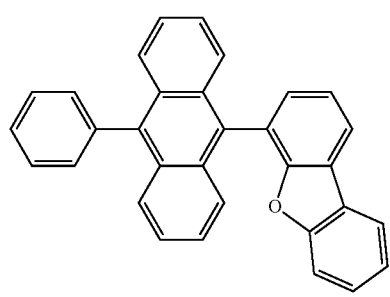
H19
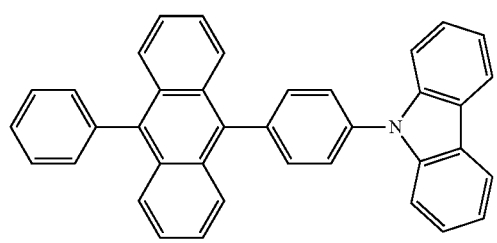
H20
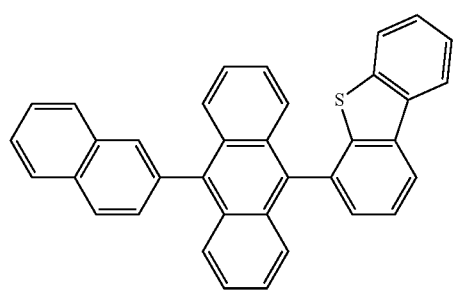
H21
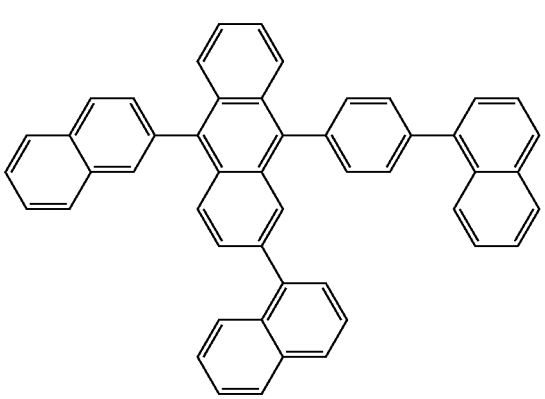
H22
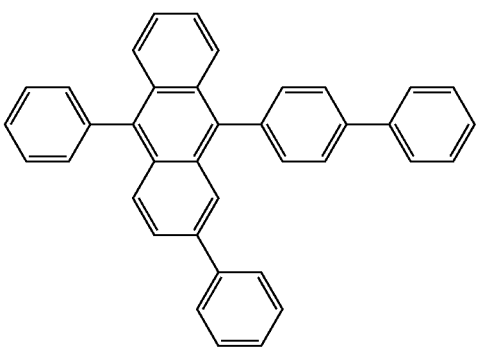
H23
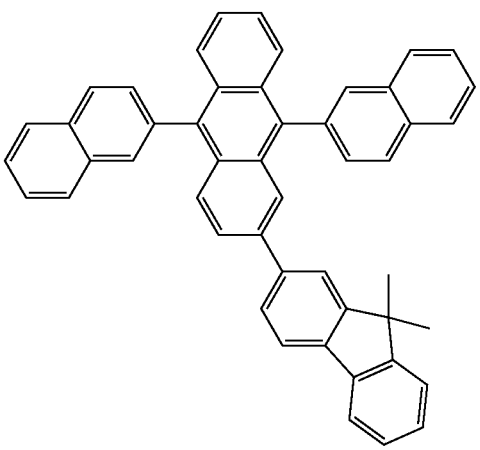
H24
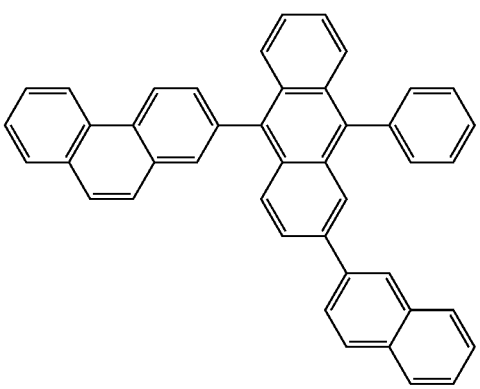

51
-continued
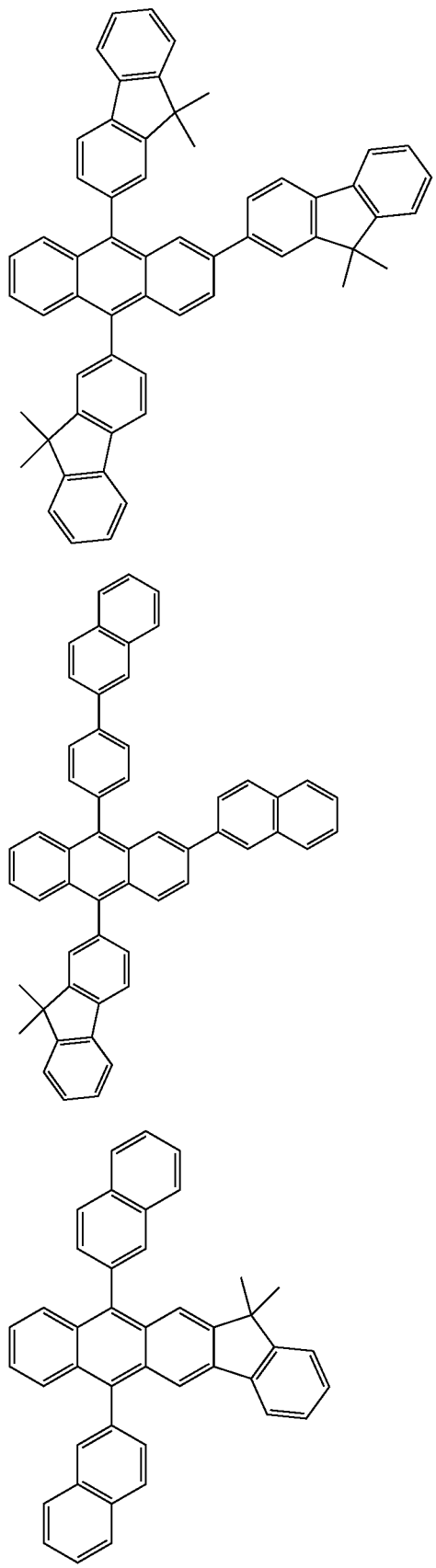
52
-continued
H25
H26
H27
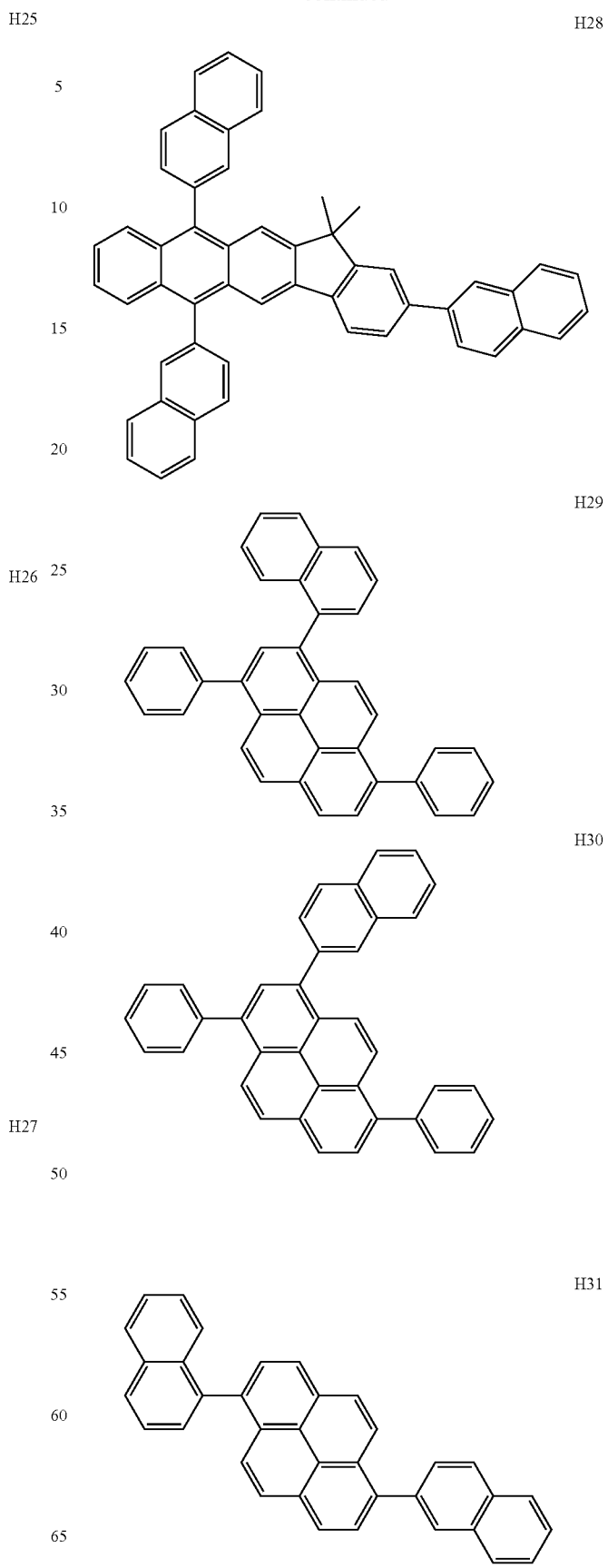
H28
H29
H30
H31

H32
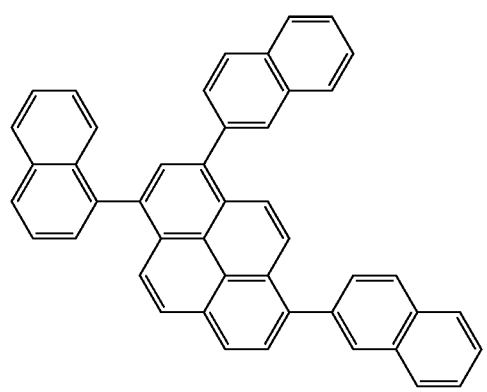
H33
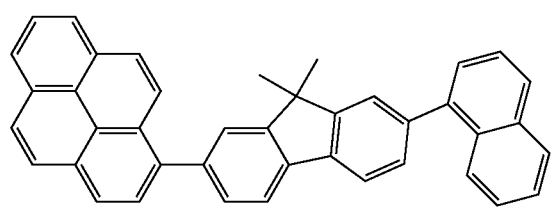
H34
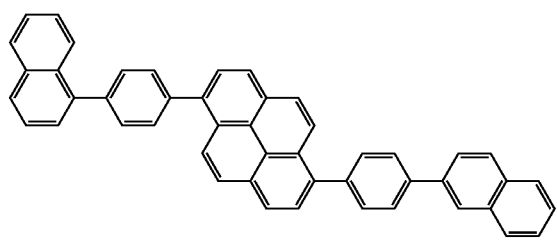
H35
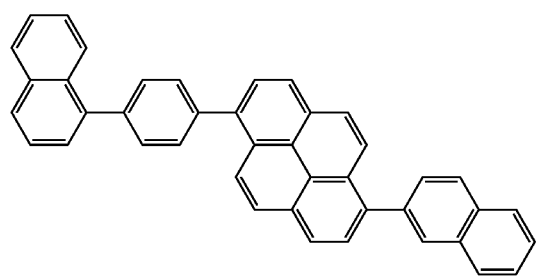
H36
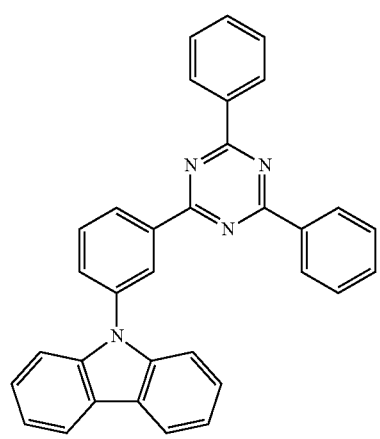
H37
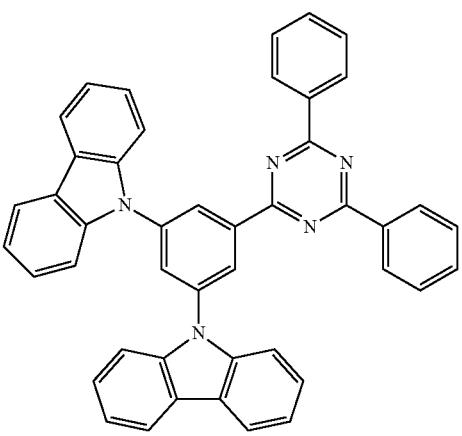
H38
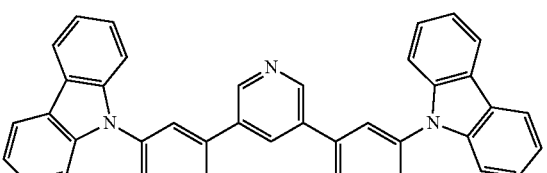
H39
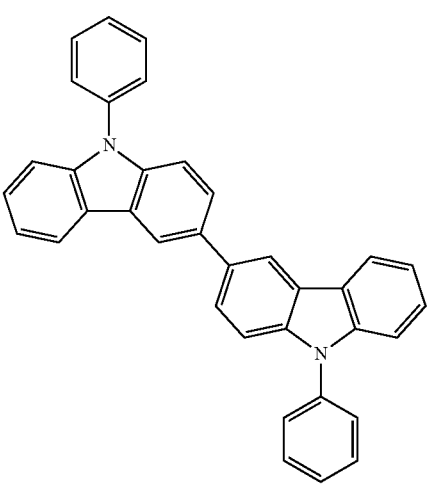

-continued
H40
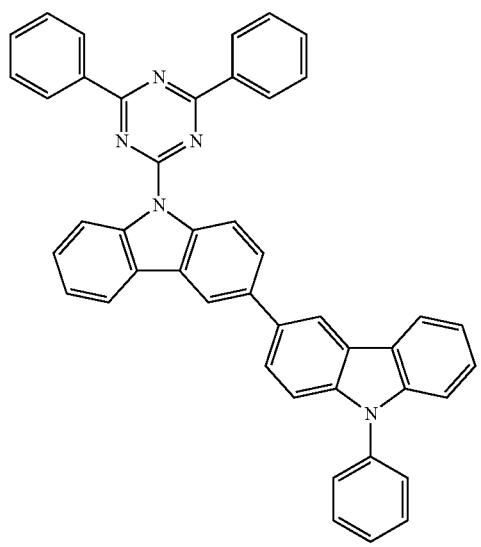
H41
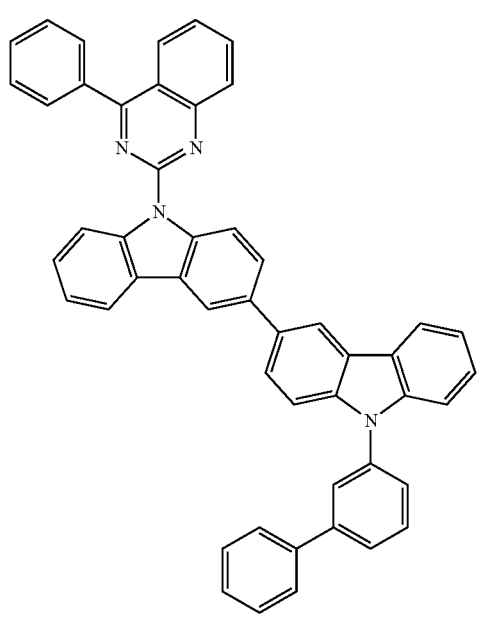
H42
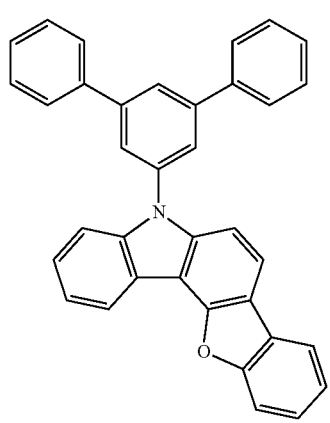
-continued
H43
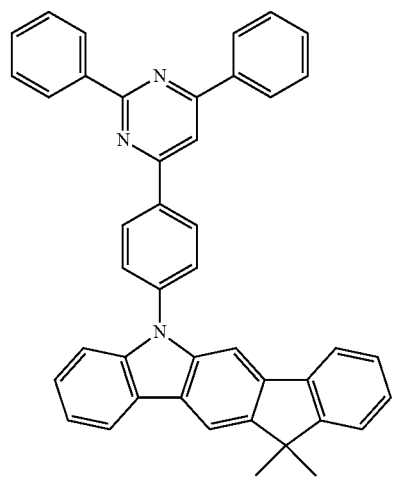
H44
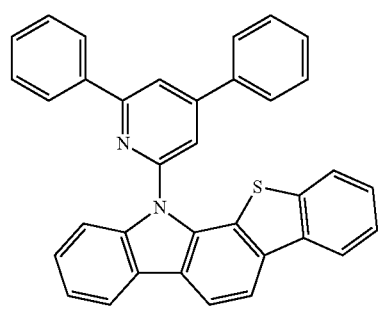
H45
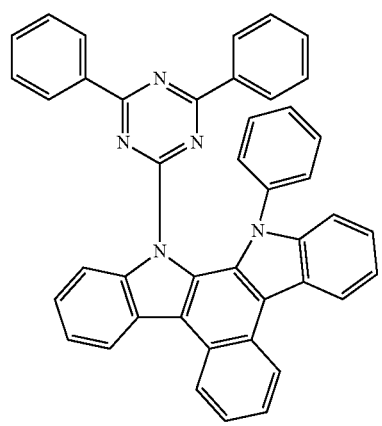
H46
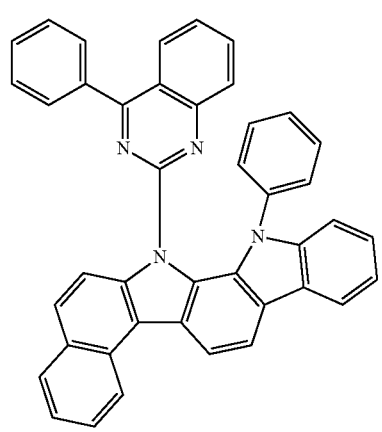

H47
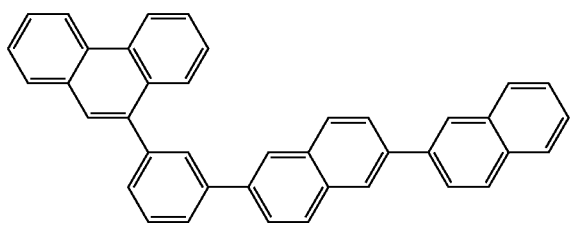
H48
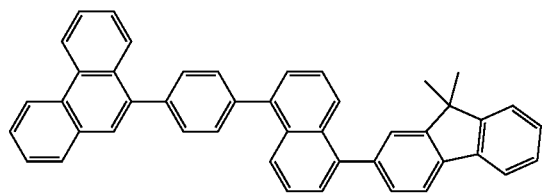
H49
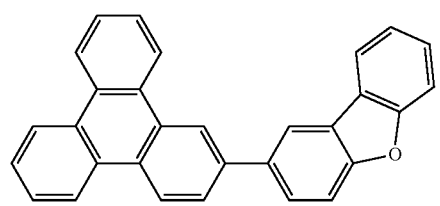
H50
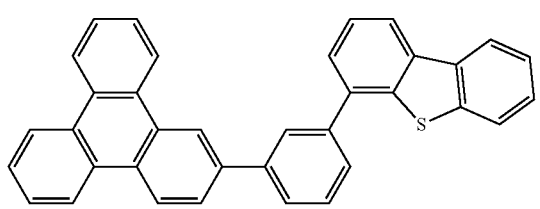
H51
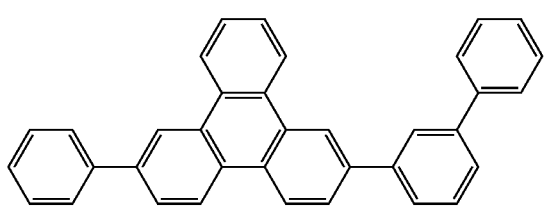
H52
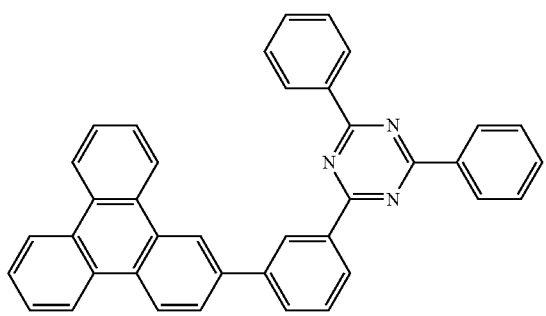
H53
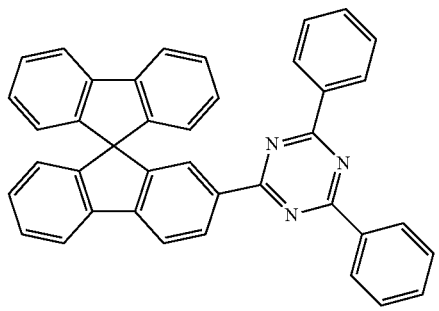
H54
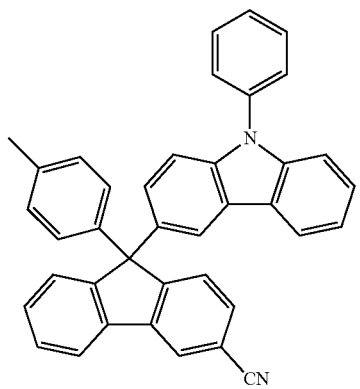
H55
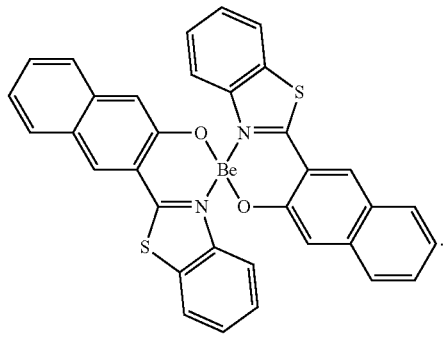
Phosphorescence Dopant Included in Emission Layer in Organic Layer 150
The phosphorescence dopant may include an organo metallic complex represented by Formula 401 below:
$$M(L_{401})_{xc1}(L_{402})_{xc2} \quad \text{Formula 401}$$
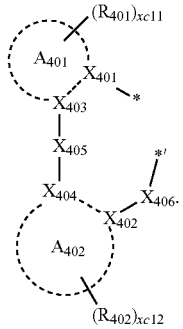
Formula 402

In Formulae 401 and 402, $L_{401}$ may be selected from ligands represented by Formula 402, and xc1 may be 1, 2, and/or 3, wherein, when xc1 is two or more, two or more $L_{401}$(s) may be identical to or different from each other, $L_{402}$ may be an organic ligand, and xc2 may be an integer from 0 to 4, wherein, when xc2 is two or more, two or more $L_{402}$(s) may be identical to or different from each other, $X_{401}$ to $X_{404}$ may each independently be nitrogen and/or carbon, $X_{401}$ and $X_{403}$ may be linked via a single bond and/or a double bond, and $X_{402}$ and $X_{404}$ may be linked via a single bond and/or a double bond, ring $A_{401}$ and ring $A_{402}$ may each independently be selected from a $C_4$-$C_{60}$ carbocyclic group and/or a $C_1$-$C_{60}$ heterocyclic group, $X_{405}$ may be a single bond, *—C(=O)—', *—N($Q_{411}$)-', *—C($Q_{411}$)($Q_{412}$)-*', *—C($Q_{411}$)=C($Q_{412}$)-*', *—C($Q_{411}$)=', and/or *=C($Q_{411}$)=', wherein $Q_{411}$ and $Q_{412}$ may be hydrogen, deuterium, a $C_1$-$C_{20}$ alkyl group, a $C_1$-$C_{20}$ alkoxy group, a phenyl group, a biphenyl group, a terphenyl group, and/or a naphthyl group, $X_{406}$ may be a single bond, O, and/or S, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, xc11 and xc12 may each independently be an integer from 0 to 10, and and *' in Formula 402 each indicate a binding site to M in Formula 401.

In one embodiment, ring $A_{401}$ and ring $A_{402}$ in Formula 402 may each independently be selected from a benzene group, a naphthalene group, a fluorene group, a spirobifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In one or more embodiments, in Formula 402, i) $X_{401}$ may be nitrogen, and $X_{402}$ may be carbon, or ii) $X_{401}$ and $X_{402}$ may each be nitrogen at the same time.

In one or more embodiments, $R_{401}$ and $R_{402}$ in Formula 402 may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantanyl group, a norbornanyl group, and a norbornenyl group;

a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantanyl group, a norbornanyl group, a norbornenyl group a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$); and $Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group, but embodiments of the present disclosure are not limited thereto.

In one or more embodiments, when xc1 in Formula 401 is 2 or more, two $A_{401}$(s) in two or more $L_{401}$(s) may optionally be linked via $X_{407}$, which is a linking group, and/or two $A_{402}$(s) in two or more $L_{401}$(s) may optionally be linked via $X_{408}$, which is a linking group (see e.g., Compounds PD1 to PD4 and PD7). $X_{407}$ and $X_{408}$ may each independently be a single bond, *—C(=O)—*', *—N($Q_{413}$)-*', *—C($Q_{413}$)($Q_{414}$)-*', and/or *—C($Q_{413}$)=C($Q_{414}$)-*' (wherein $Q_{413}$ and $Q_{414}$ may each independently be hydrogen, deuterium, a $C_1$-$C_{20}$ alkyl group, a $C_1$-$C_{20}$ alkoxy group, a phenyl group, a biphenyl group, a terphenyl group, and/or a naphthyl group), but are not limited thereto.

$L_{402}$ in Formula 401 may be a monovalent, divalent, or trivalent organic ligand. For example, $L_{402}$ may be selected from halogen, diketone (for example, acetylacetonate), carboxylic acid (for example, picolinate), —C(=O), isonitrile, —CN, and phosphorus (for example, phosphine and/or phosphite), but embodiments of the present disclosure are not limited thereto.

In one or more embodiments, the phosphorescence dopant may be selected from, for example, Compounds PD1 to PD25, but embodiments of the present disclosure are not limited thereto:
PD1
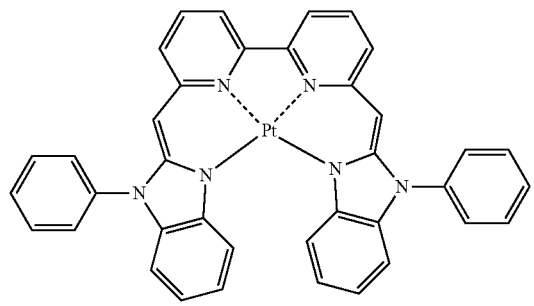
PD2
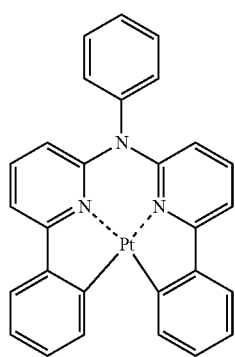
PD3
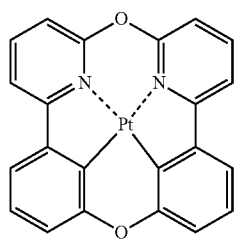
PD4
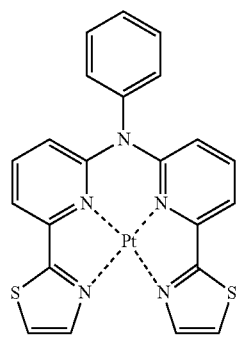
PD5
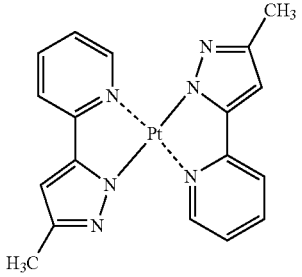
PD6
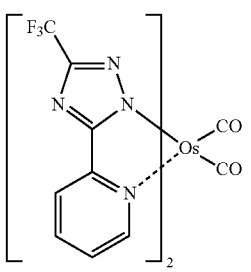
PD7
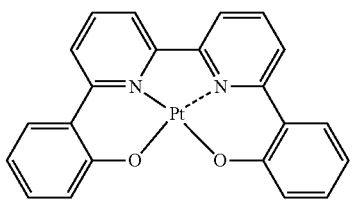
PD8
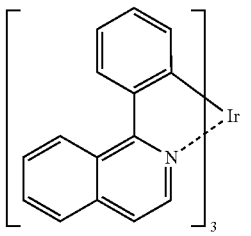
PD9
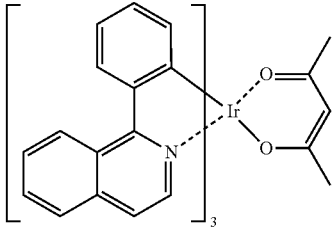
PD10
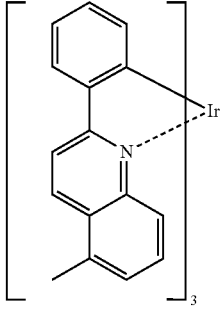

-continued
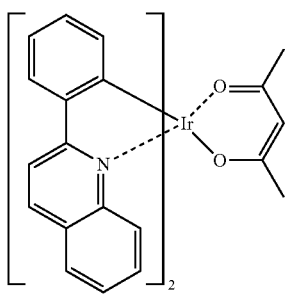
PD11
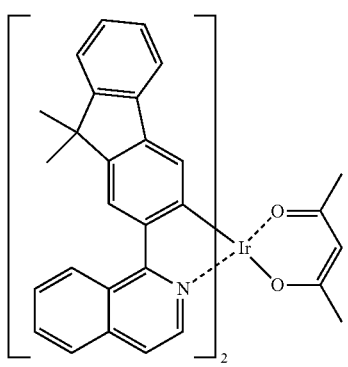
PD12
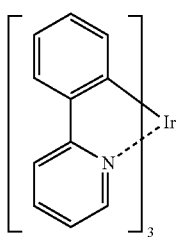
PD13
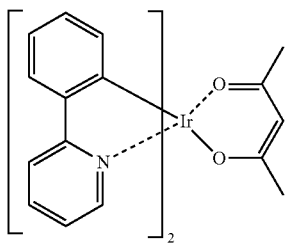
PD14
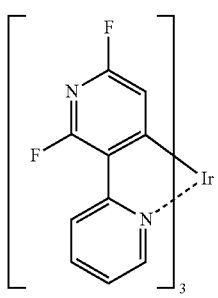
PD15
-continued
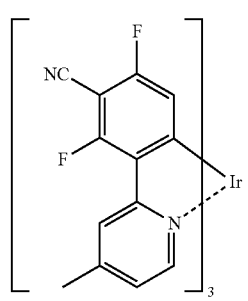
PD16
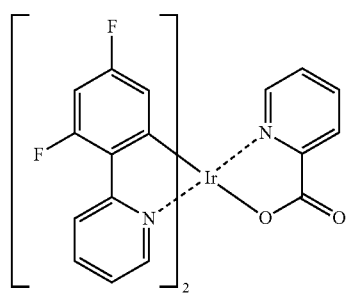
PD17
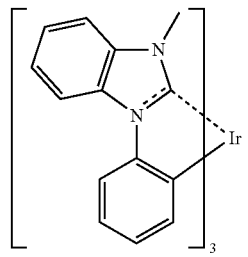
PD18
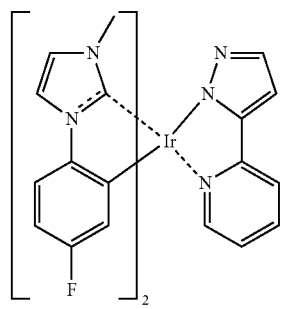
PD19
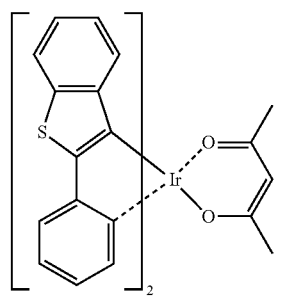
PD20

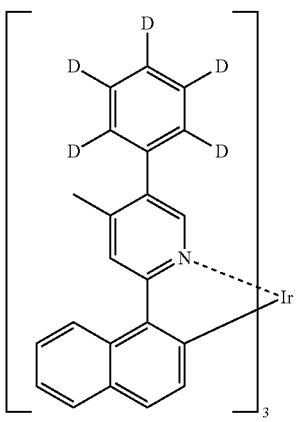

Fluorescence Dopant in Emission Layer

The fluorescence dopant may include an arylamine compound and/or a styrylamine compound.

The fluorescence dopant may include a compound represented by Formula 501 below:

$$Ar_{501}\!\!-\!\!\left[(L_{503})_{xd3}\!\!-\!\!N\!\!\begin{array}{c}(L_{501})_{xd1}\!\!-\!\!R_{501}\\ (L_{502})_{xd2}\!\!-\!\!R_{502}\end{array}\right]_{xd4}.$$ Formula 501

In Formula 501, $Ar_{501}$ may be a substituted or unsubstituted $C_4$-$C_{60}$ carbocyclic group and/or a substituted or unsubstituted $C_1$-$C_{60}$ heterocyclic group, $L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer from 0 to 3, $R_{501}$ and $R_{502}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and xd4 may be an integer from 1 to 6.

In one embodiment, $Ar_{501}$ in Formula 501 may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one or more embodiments, $L_{501}$ to $L_{503}$ in Formula 501 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In one or more embodiments, $R_{501}$ and $R_{502}$ in Formula 501 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group and —Si($Q_{31}$)($Q_{32}$)($Q_{33}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xd4 in Formula 501 may be 2, but embodiments of the present disclosure are not limited thereto.

For example, the fluorescence dopant may be selected from Compounds FD1 to FD22 below:

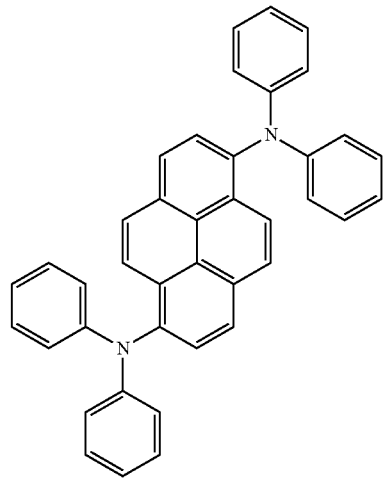

FD1

FD2 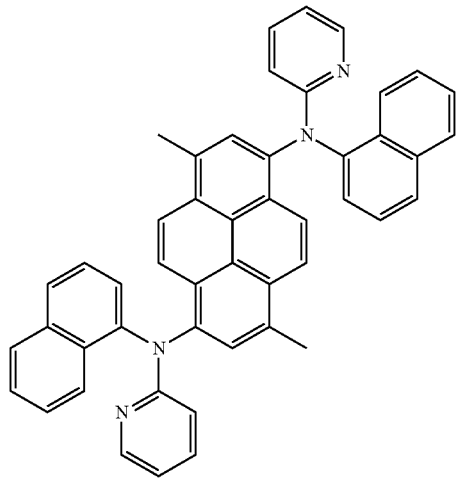
FD5 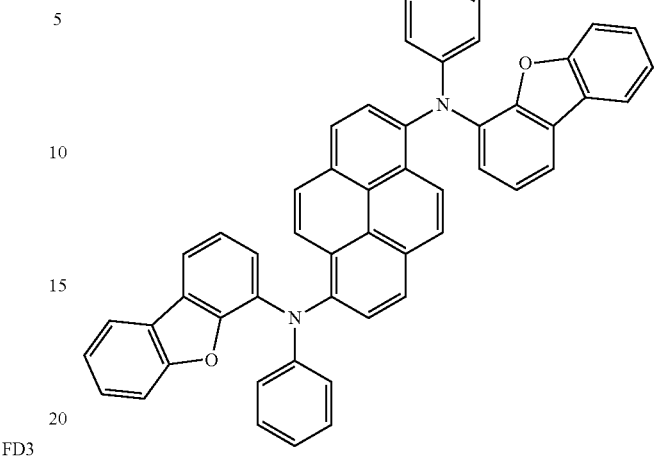
FD3 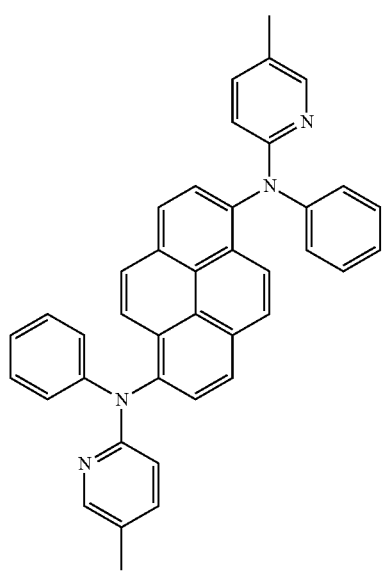
FD6 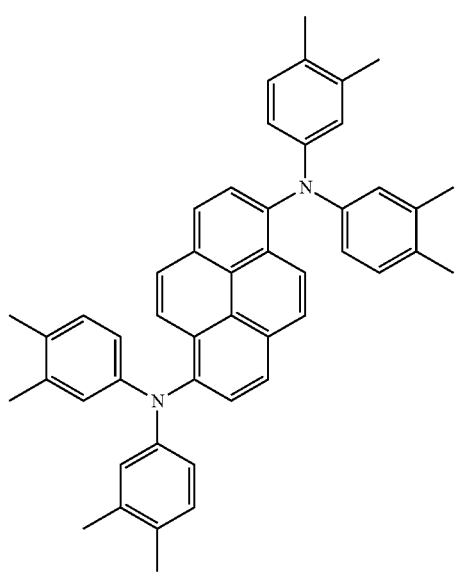
FD4 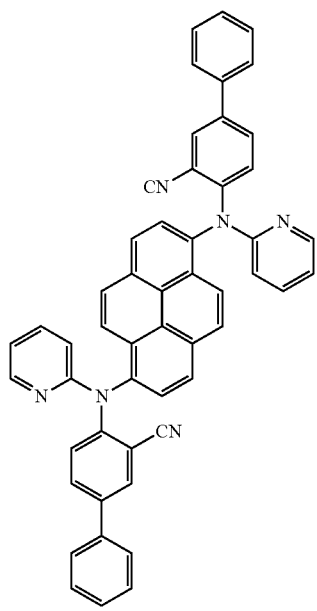
FD7

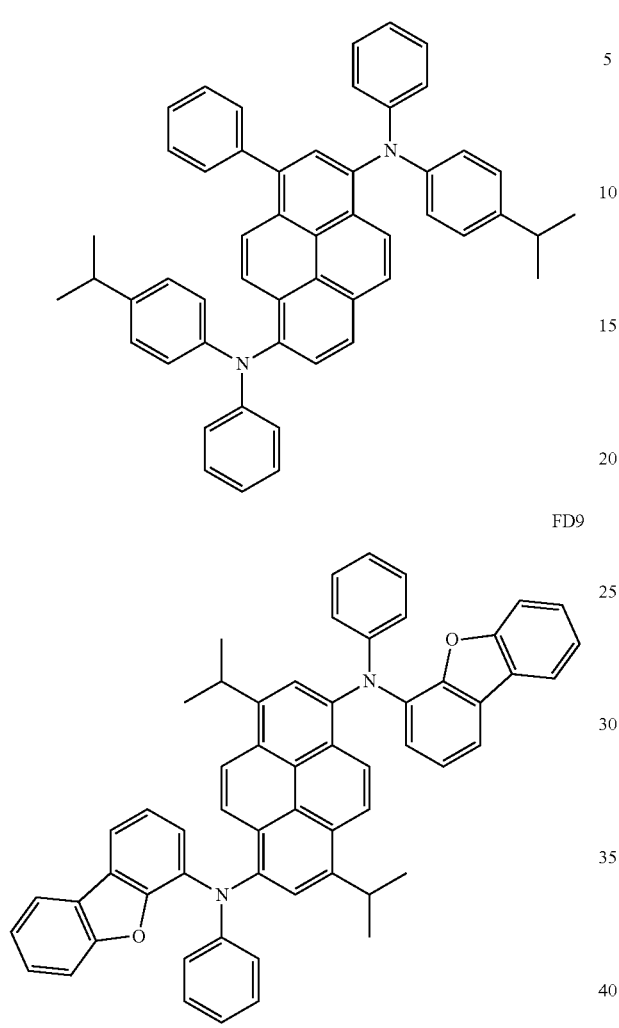
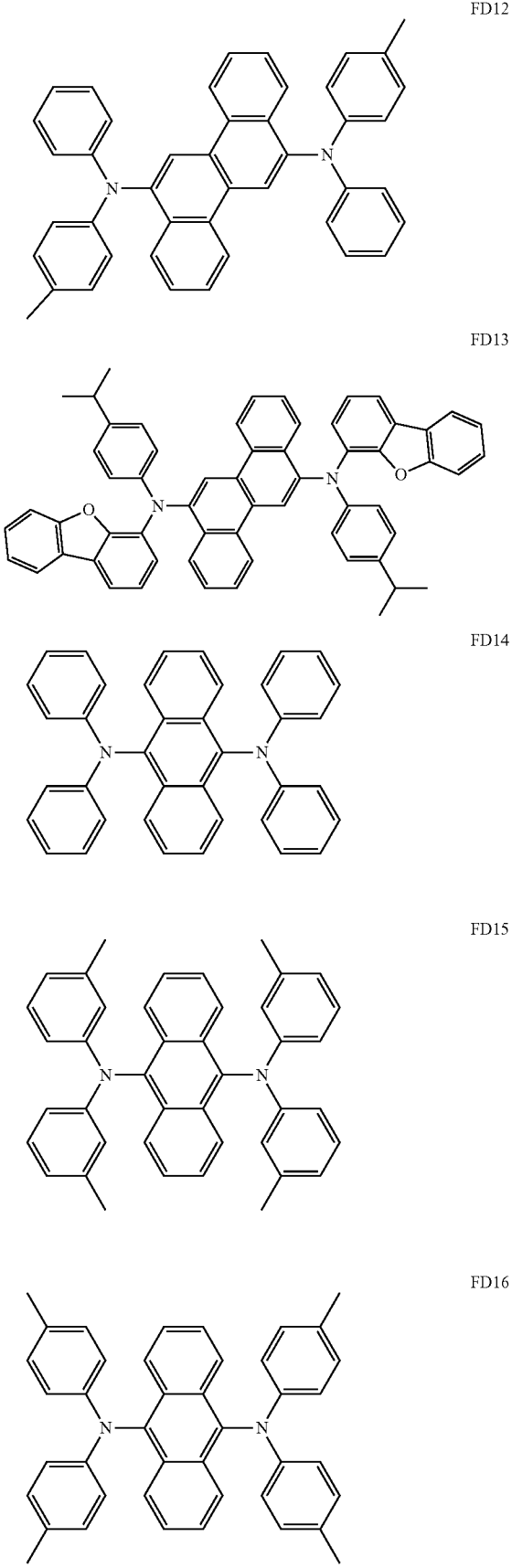

-continued
FD17
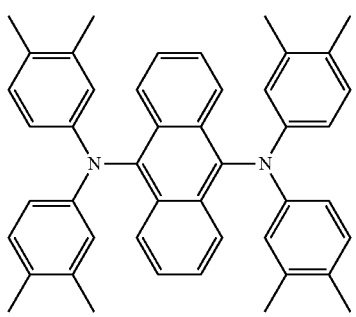
FD18
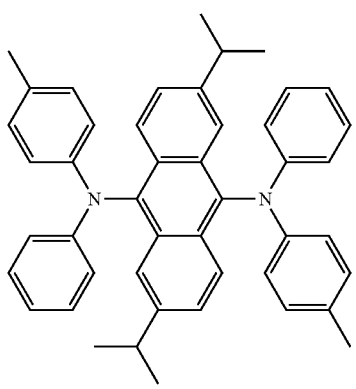
FD19
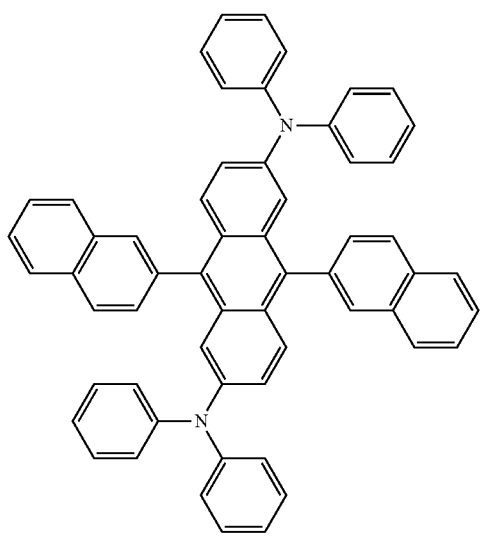
-continued
FD20
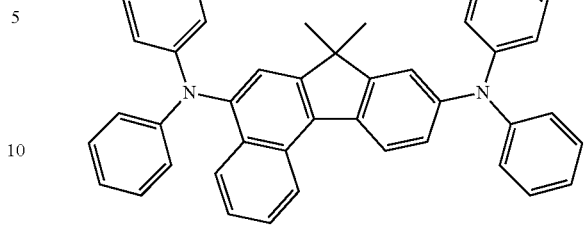
FD21
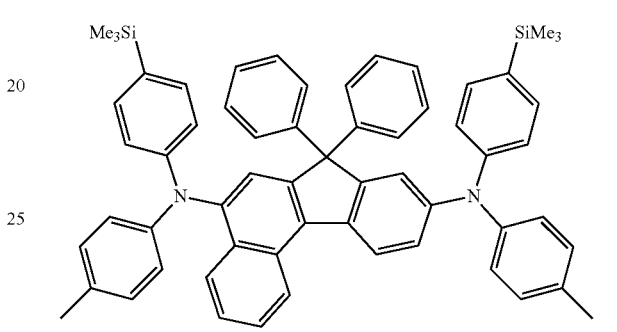
FD22
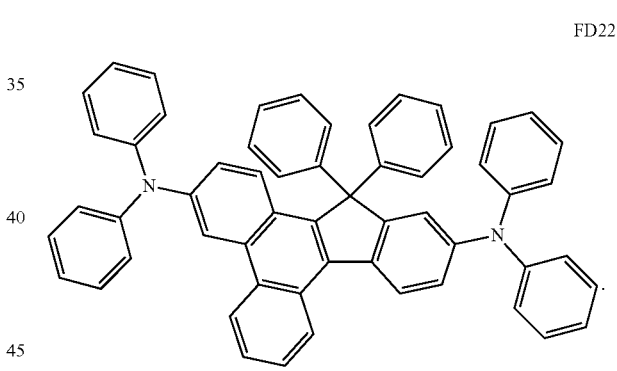
In one or more embodiments, the fluorescence dopant may be selected from the following compounds, but embodiments of the present disclosure are not limited thereto:
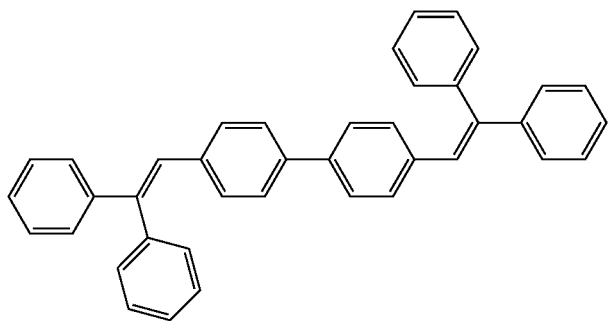
DPVBi -continued

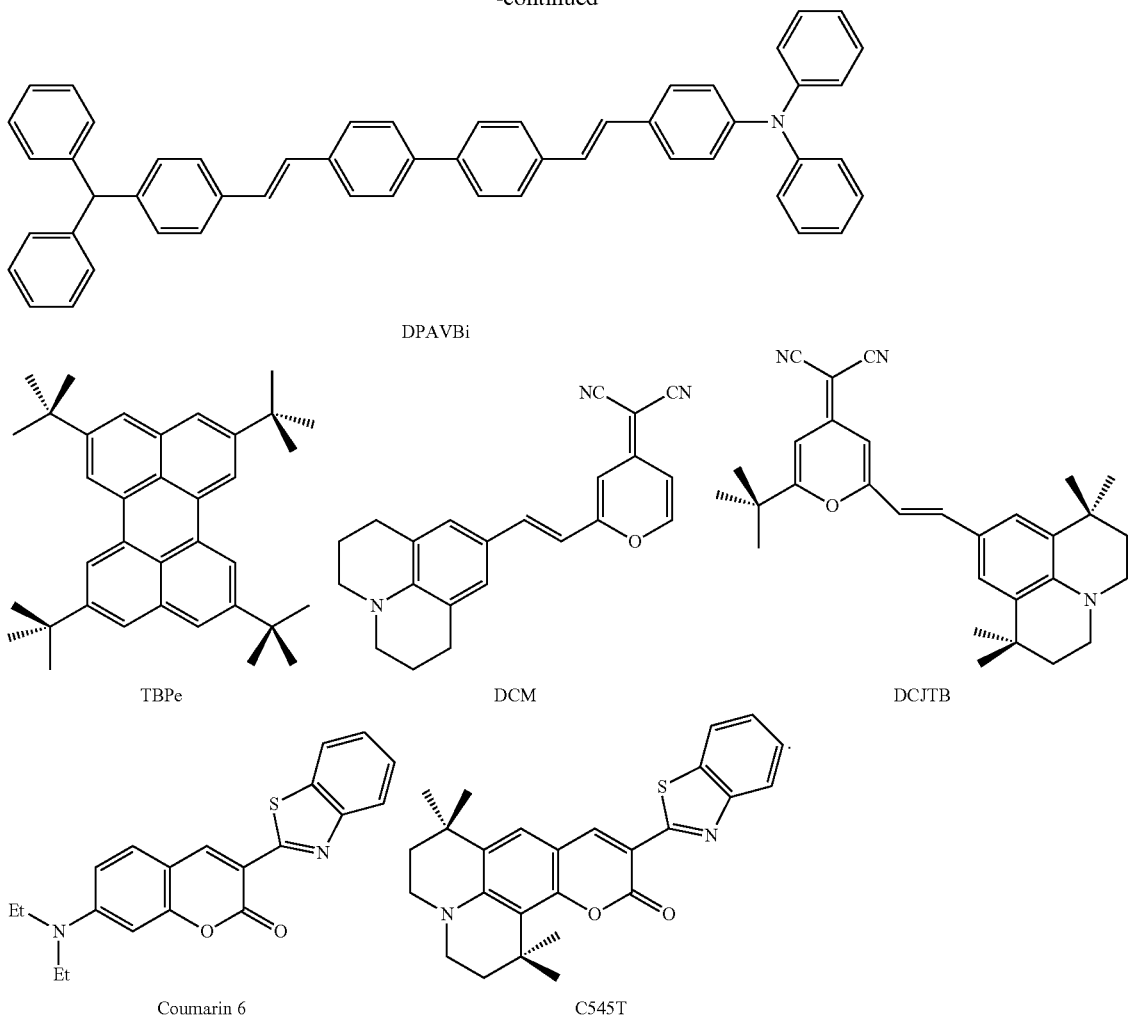

Quantum Dot in Emission Layer

A quantum dot in an emission layer may include a IV-VI Group compound, a IV Group element, and/or a IV Group compound. The IV-VI Group compound may be selected from: a binary compound (selected from SnS, SnSe, SnTe, PbS, PbSe, PbTe, and any mixture thereof); a ternary compound (selected from SnSeS, SnSeTe, SnSTe, PbSeS, PbSeTe, PbSTe, SnPbS, SnPbSe, SnPbTe, and any mixture thereof); and a quaternary compound (selected from SnPbSSe, SnPbSeTe, SnPbSTe, and any mixture thereof). The IV Group element may be selected from Si, Ge, and any mixture thereof. The IV Group compound may be a binary compound selected from SiC, SiGe, and any mixture thereof.

The binary compound, the ternary compound, and/or the quaternary compound may exist in particles at uniform concentration, or may exist in the same particle in a state in which a concentration distribution is partially different. In some embodiments, the binary compound, the ternary compound, and/or the quaternary compound may have a core-shell structure in which one quantum dot surrounds another quantum dot. An interface between the core and the shell may have a concentration gradient in which the concentration of atoms existing in the shell decreases toward the center.

In one or more embodiments, the quantum dot may have a core-shell structure including a core with the above-described nanoparticles and a shell surrounding the core. The shell of the quantum dot may serve as a protective layer for maintaining semiconductor characteristics by preventing or reducing chemical degeneration of the core and/or may serve as a charging layer for imparting electrophoretic characteristics to the quantum dot. The shell may be a single layer or a multilayer. An interface between the core and the shell may have a concentration gradient in which the concentration of atoms existing in the shell decreases toward the center. Examples of the shell of the quantum dot may include a metal oxide, a non-metal oxide, a semiconductor compound, and any combinations thereof.

For example, examples of the metal oxide and the non-metal oxide may include a binary compound (such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, and/or NiO), and a ternary compound (such as $MgAl_2O_4$, $CoFe_2O_4$, $NiFe_2O_4$, and/or $CoMn_2O_4$), but embodiments of the present disclosure are not limited thereto.

Examples of the semiconductor compound may include CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, and the like, but embodiments of the present disclosure are not limited thereto.

A full width of half maximum (FWHM) of an emission wavelength spectrum of the quantum dot may be about 45 nm or less, for example, about 40 nm or less, for example, about 30 nm or less. When the FWHM of the emission wavelength spectrum of the quantum dot is within this range, color purity and/or color reproduction may be improved. In addition, light emitted through such quantum dot is irradiated in omnidirection, thereby improving a wide viewing angle.

In some embodiments, a spherical, pyramidal, multi-arm, and/or cubic nanoparticle, nanotube, nanowire, nanofiber, and/or nanoplate particle may be used.

The quantum dot may adjust the color of emitted light according to the particle size. Therefore, the quantum dot may generate various emission colors such as blue, red, and/or green.

Electron Transport Region in Organic Layer 150

The electron transport region may have i) a single-layered structure including a single layer including a single material, ii) a single-layered structure including a single layer including a plurality of different materials, or iii) a multi-layered structure having a plurality of layers including a plurality of different materials.

The electron transport region may include at least one selected from a hole blocking layer, an electron control layer, an electron transport layer, and an electron injection layer, but embodiments of the present disclosure are not limited thereto.

For example, the electron transport region may have an electron transport layer/electron injection layer structure, a hole blocking layer/electron transport layer/electron injection layer structure, an electron control layer/electron transport layer/electron injection layer structure, or an electron transport layer/electron injection layer structure, wherein for each structure, constituting layers are sequentially stacked from an emission layer. However, embodiments of the structure of the electron transport region are not limited thereto.

The electron transport region (for example, a buffer layer, a hole blocking layer, an electron control layer, and/or an electron transport layer in the electron transport region) may include a metal-free compound containing at least one π electron-depleted nitrogen-containing ring.

The "π electron-depleted nitrogen-containing ring" may refer to a $C_1$-$C_{60}$ heterocyclic group having at least one *—N=*' moiety as a ring-forming moiety.

For example, the "π electron-depleted nitrogen-containing ring" may be i) a 5-membered to 7-membered heteromonocyclic group having at least one *—N=*' moiety, ii) a heteropolycyclic group in which two or more 5-membered to 7-membered heteromonocyclic groups, each having at least one *—N=*' moiety, are condensed with each other, or iii) a heteropolycyclic group in which at least one of 5-membered to 7-membered heteromonocyclic groups, each having at least one *—N=*' moiety, is condensed with at least one $C_5$-$C_{60}$ carbocyclic group.

Examples of the π electron-depleted nitrogen-containing ring include an imidazole, a pyrazole, a thiazole, an isothiazole, an oxazole, an isoxazole, a pyridine, a pyrazine, a pyrimidine, a pyridazine, an indazole, a purine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzimidazole, an isobenzothiazole, a benzoxazole, an isobenzoxazole, a triazole, a tetrazole, an oxadiazole, a triazine, a thiadiazole, an imidazopyridine, an imidazopyrimidine, and an azacarbazole, but are not limited thereto.

For example, the electron transport region may include a compound represented by Formula 601 below:

$$[Ar_{601}]_{xe11}\text{-}[(L_{601})_{xe1}\text{-}R_{601}]_{xe21}. \quad \text{Formula 601}$$

In Formula 601, $Ar_{601}$ may be a substituted or unsubstituted $C_4$-$C_{60}$ carbocyclic group and/or a substituted or unsubstituted $C_1$-$C_{60}$ heterocyclic group, xe11 may be 1, 2, and/or 3, $L_{601}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xe1 may be an integer from 0 to 5, $R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{601}$)($Q_{602}$)($Q_{603}$), —C(=O)($Q_{601}$), —S(=O)$_2$($Q_{601}$), and —P(=O)($Q_{601}$)($Q_{602}$), $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, and/or a naphthyl group, and xe21 may be an integer from 1 to 5.

In one embodiment, at least one of $Ar_{601}$(s) in the number of xe11 and $R_{601}$(s) in the number of xe21 may include the π electron-depleted nitrogen-containing ring.

In one embodiment, $Ar_{601}$ in Formula 601 may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(=O)$_2$($Q_{31}$), and —P(=O)($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is 2 or more, two or more $Ar_{601}$(s) may be linked via a single bond.

In one or more embodiments, $Ar_{601}$ in Formula 601 may be an anthracene group.

In one or more embodiments, a compound represented by Formula 601 may be represented by Formula 601-1 below:

Formula 601-1

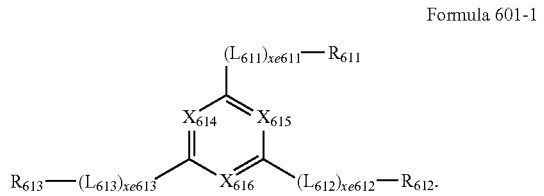

In Formula 601-1, $X_{614}$ may be N or C($R_{614}$), $X_{615}$ may be N or C($R_{615}$), $X_{616}$ may be N or C($R_{616}$), and at least one selected from $X_{614}$ to $X_{616}$ may be N, $L_{611}$ to $L_{613}$ may each independently be the same as described in connection with $L_{601}$, xe611 to xe613 may each independently be defined the same as xe1, $R_{611}$ to $R_{613}$ may each independently be the same as described in connection with $R_{601}$, and $R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one embodiment, $L_{601}$ and $L_{611}$ to $L_{613}$ in Formulae 601 and 601-1 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, but embodiments of the present disclosure are not limited thereto.

In one or more embodiments, xe1 and xe611 to xe613 in Formulae 601 and 601-1 may each independently be 0, 1, and/or 2.

In one or more embodiments, $R_{601}$ and $R_{611}$ to $R_{613}$ in Formula 601 and 601-1 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S(=O)$_2$(Q$_{601}$) and —P(=O)(Q$_{601}$)(Q$_{602}$), and Q$_{601}$ and Q$_{602}$ are the same as described above.

The electron transport region may include at least one compound selected from Compounds ET1 to ET36, but embodiments of the present disclosure are not limited thereto:

ET1

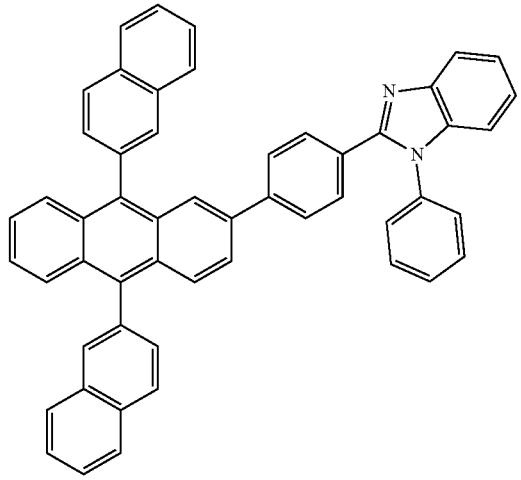

ET2
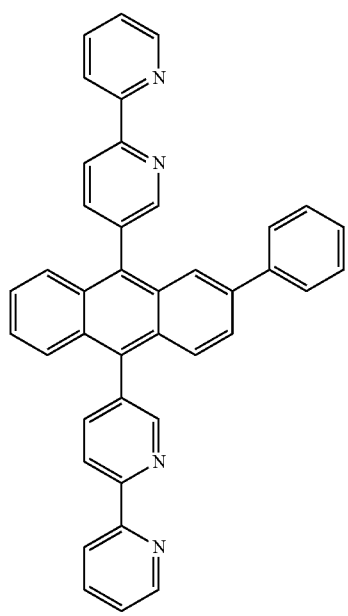
ET3
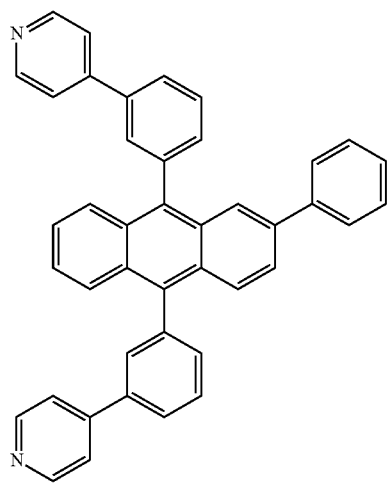
ET4
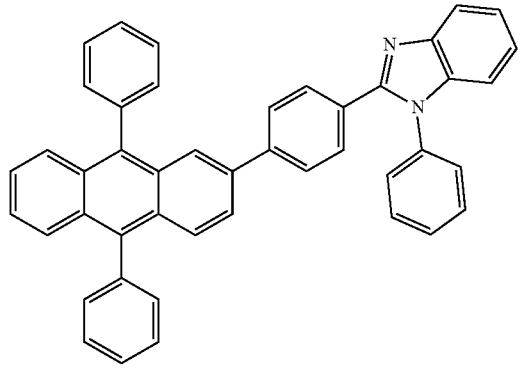
ET5
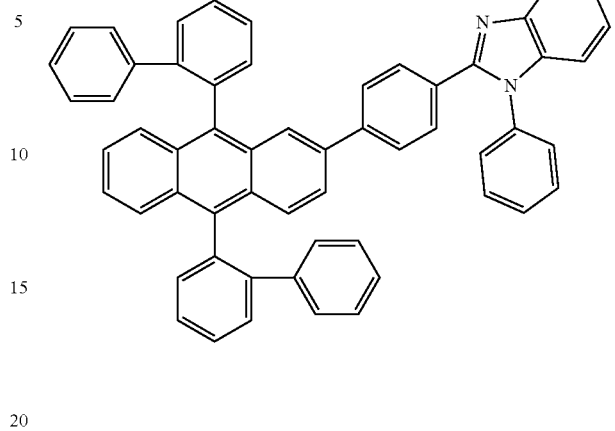
ET6
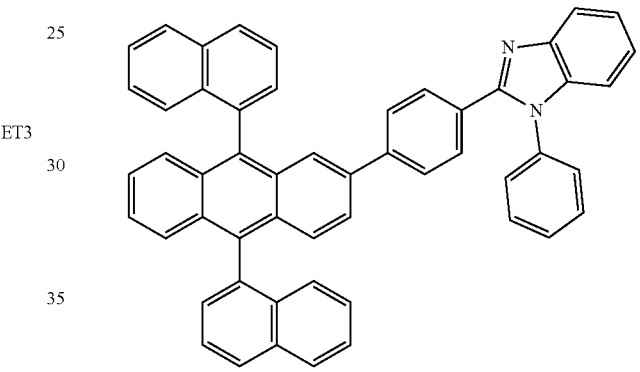
ET7
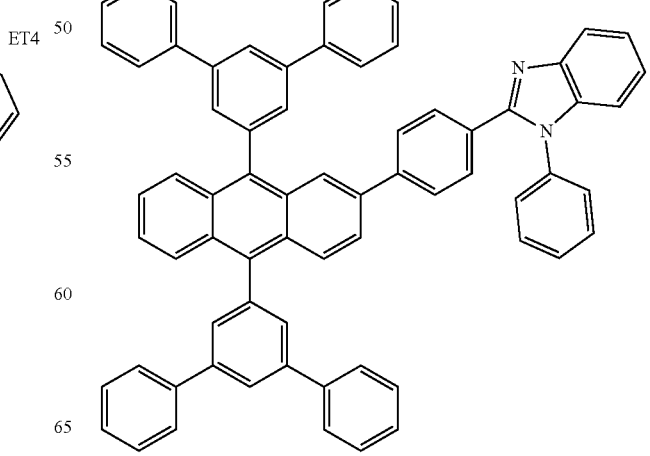

ET8
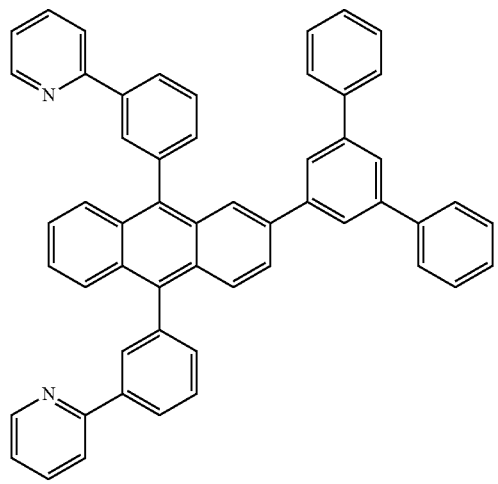
ET10
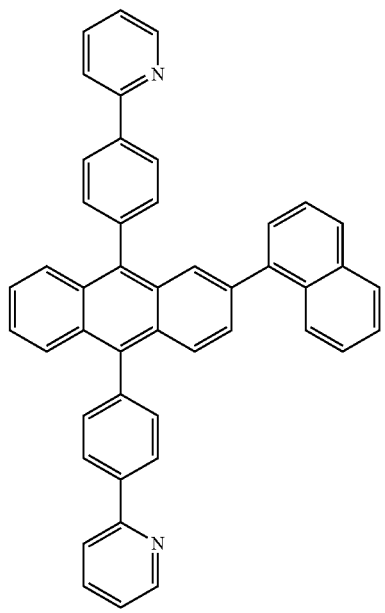
ET11
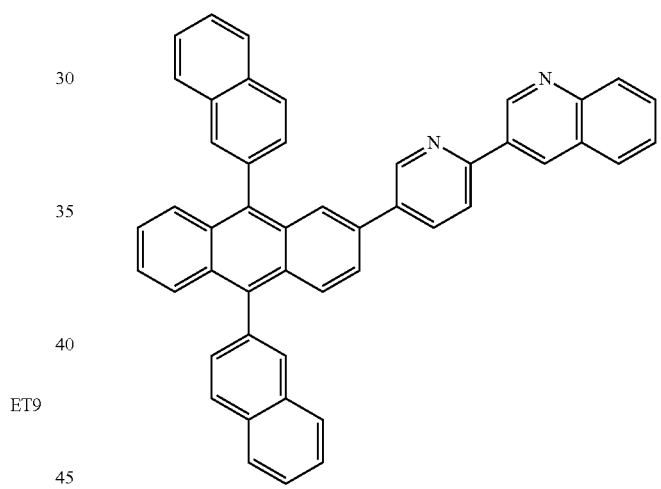
ET9
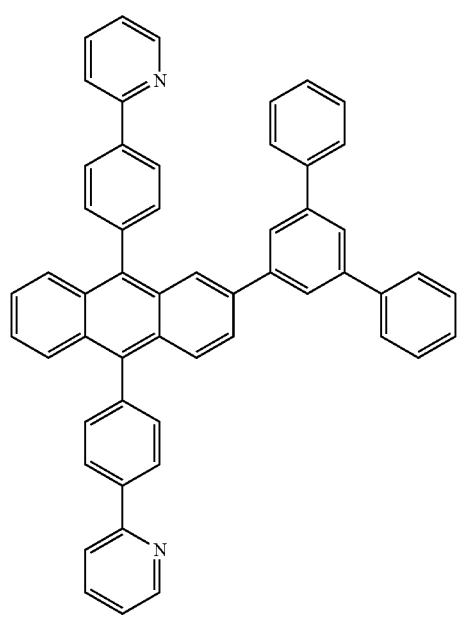
ET12
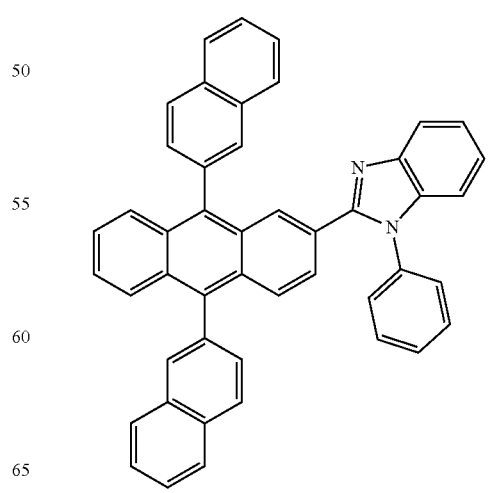

ET13
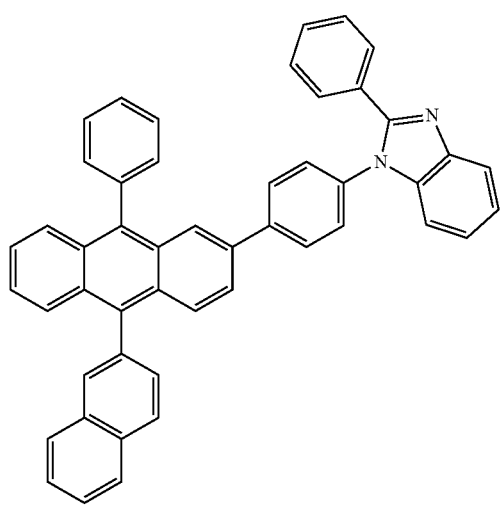
ET14
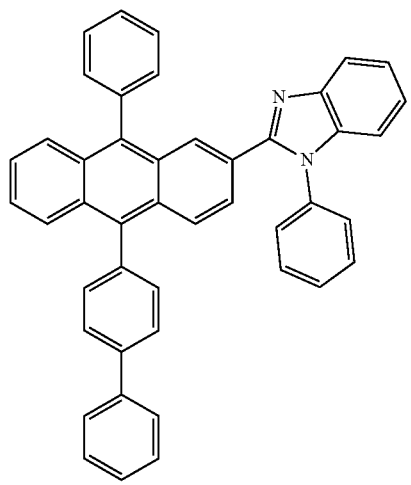
ET15
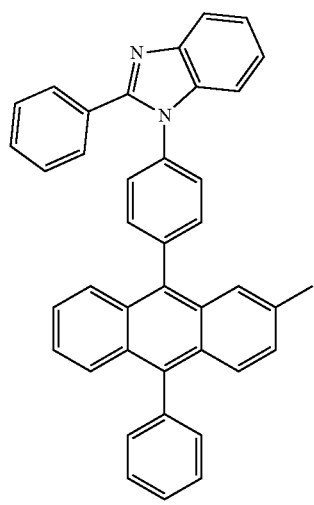
ET16
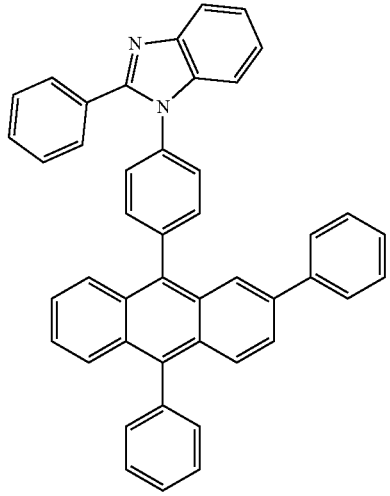
ET17
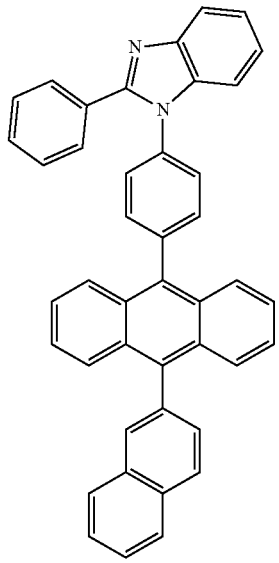
ET18
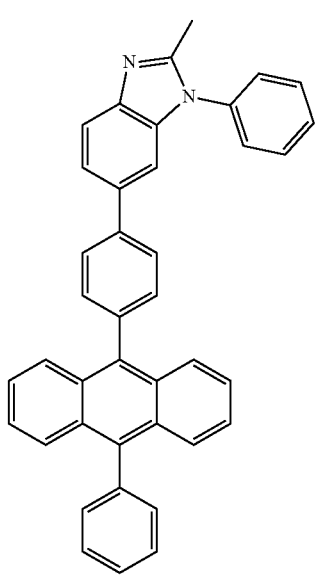

ET19
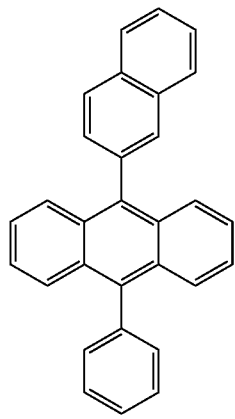
ET20
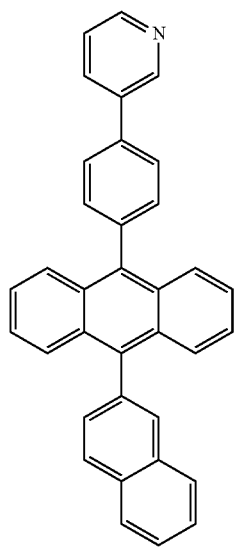
ET21
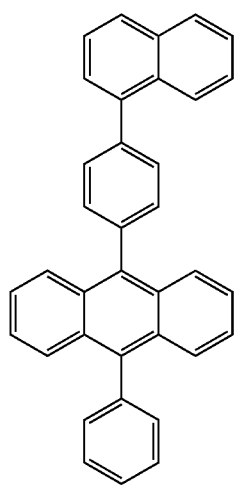
ET22
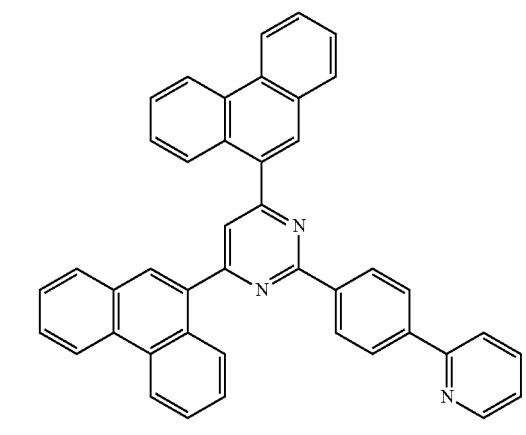
ET23
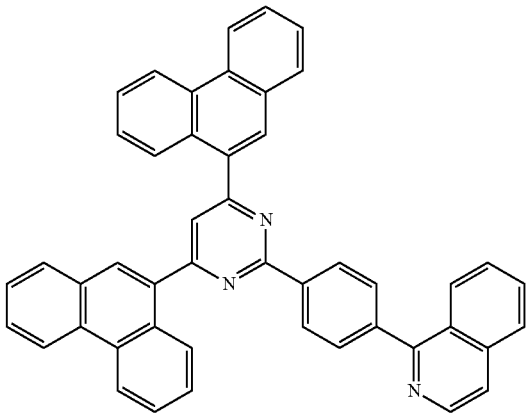
ET24

ET25
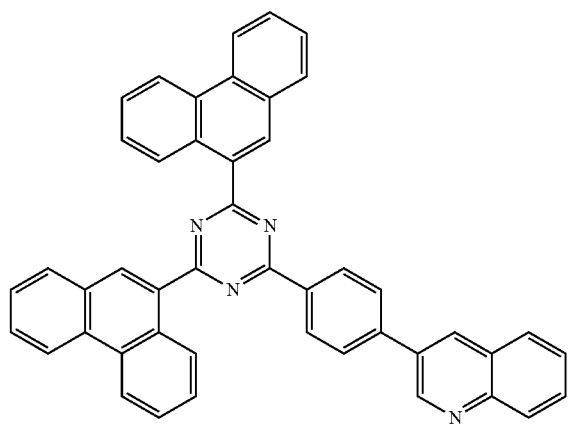
ET26
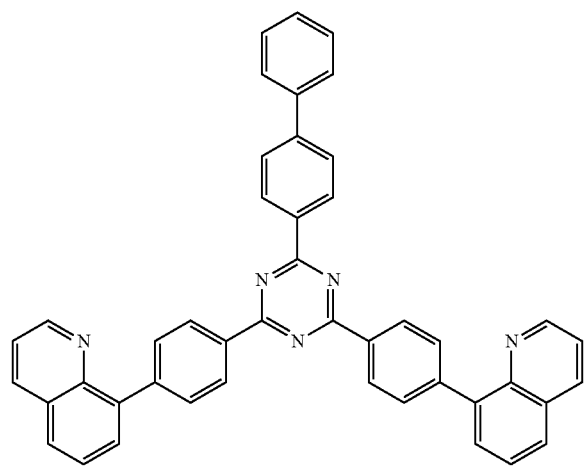
ET28
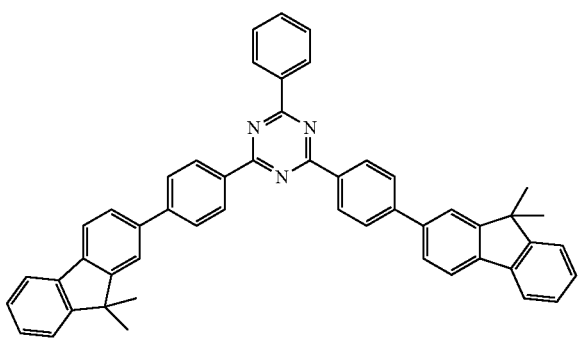
ET29
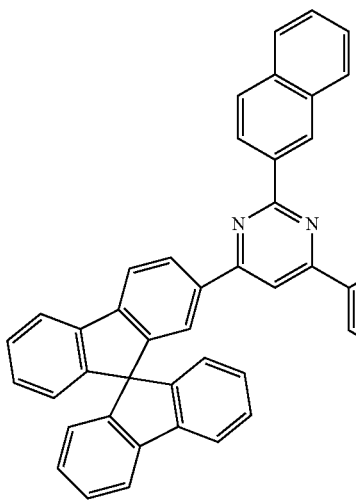
ET27
ET30
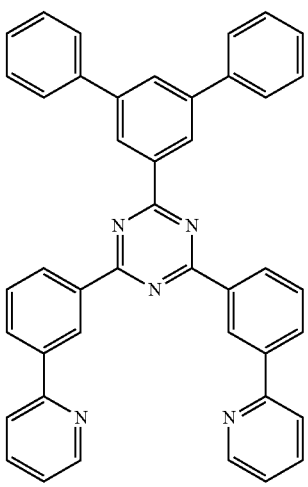

-continued
ET31
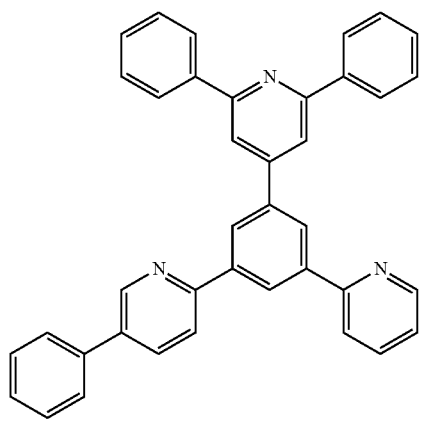
ET32
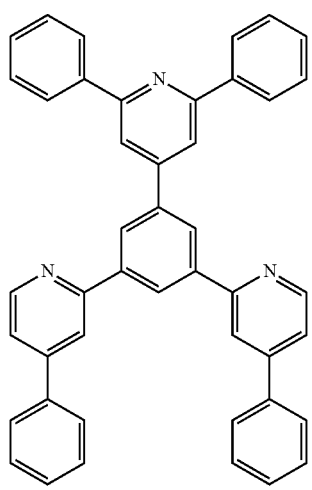
ET33
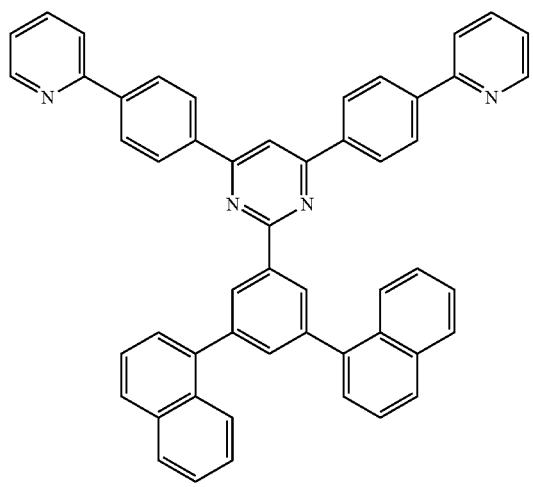
-continued
ET34
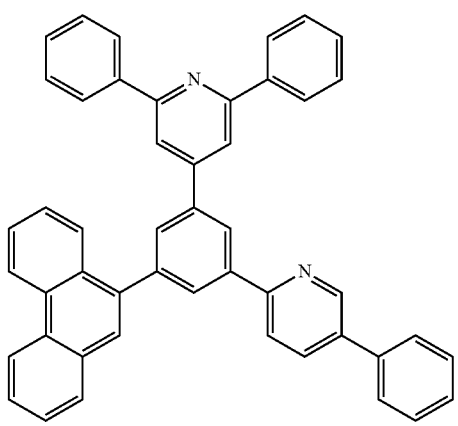
ET35
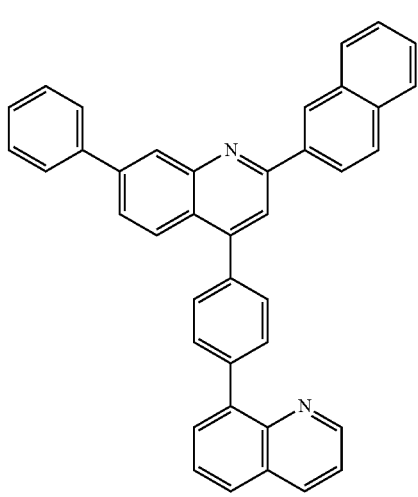
ET36
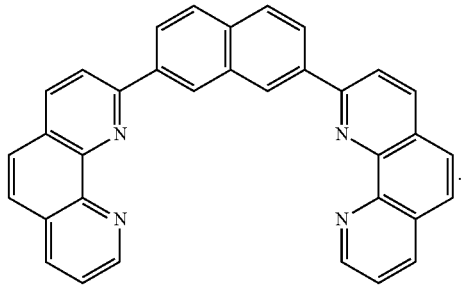
In one or more embodiments, the electron transport region may include at least one selected from 2,9-dimethyl-4,7-diphenyl-1,10-phenanthroline (BCP), 4,7-dphenyl-1,10-phenanthroline (Bphen), Alq$_3$, BAlq, 3-(biphenyl-4-yl)-5-(4-tert-butylphenyl)-4-phenyl-4H-1,2,4-triazole (TAZ), and NTAZ:

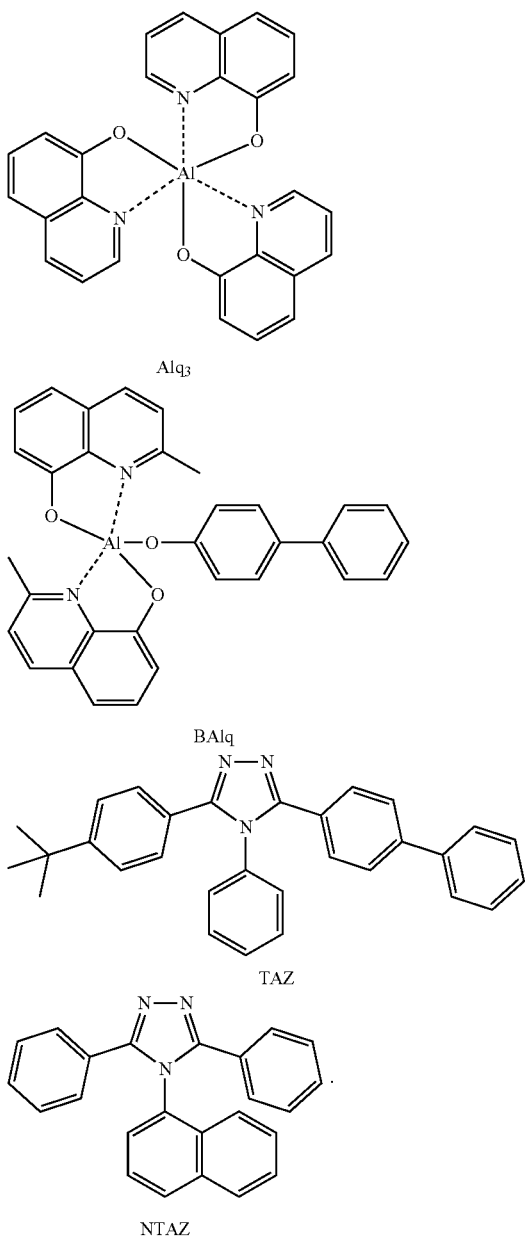

Alq₃

BAlq

TAZ

NTAZ

In one embodiment, the electron transport region may include a phosphine oxide-containing compound (for example, TSPO1 used in the following examples and/or the like), but embodiments of the present disclosure are not limited thereto. In one embodiment, the phosphine oxide-containing compound may be used in a hole blocking layer in the electron transport region, but embodiments of the present disclosure are not limited thereto.

Thicknesses of the buffer layer, the hole blocking layer, and the electron control layer may each independently be in a range of about 20 Å to about 1,000 Å, for example, about 30 Å to about 300 Å. When the thicknesses of the buffer layer, the hole blocking layer, and the electron control layer are within any of these ranges, the electron transport region may have excellent (or suitable) hole blocking characteristics and/or electron control characteristics without a substantial increase in driving voltage.

A thickness of the electron transport layer may be in a range of about 100 Å to about 1,000 Å, for example, about 150 Å to about 500 Å. When the thickness of the electron transport layer is within the range described above, the electron transport layer may have satisfactory (suitable) electron transport characteristics without a substantial increase in driving voltage.

The electron transport region (for example, the electron transport layer in the electron transport region) may further include, in addition to the materials described above, a metal-containing material.

The metal-containing material may include at least one selected from alkali metal complex and alkaline earth-metal complex. The alkali metal complex may include a metal ion selected from a Li ion, a Na ion, a K ion, a Rb ion, and a Cs ion, and the alkaline earth-metal complex may include a metal ion selected from a Be ion, a Mg ion, a Ca ion, a Sr ion, and a Ba ion. A ligand coordinated with the metal ion of the alkali metal complex or the alkaline earth-metal complex may be selected from a hydroxy quinoline, a hydroxy isoquinoline, a hydroxy benzoquinoline, a hydroxy acridine, a hydroxy phenanthridine, a hydroxy phenyloxazole, a hydroxy phenylthiazole, a hydroxy diphenyloxadiazole, a hydroxy diphenylthiadiazole, a hydroxy phenylpyridine, a hydroxy phenylbenzimidazole, a hydroxy phenylbenzothiazole, a bipyridine, a phenanthroline, and a cyclopentadiene, but embodiments of the present disclosure are not limited thereto.

For example, the metal-containing material may include a Li complex. The Li complex may include, for example, Compound ET-D1 (lithium quinolate, LiQ) and/or Compound ET-D2 below:

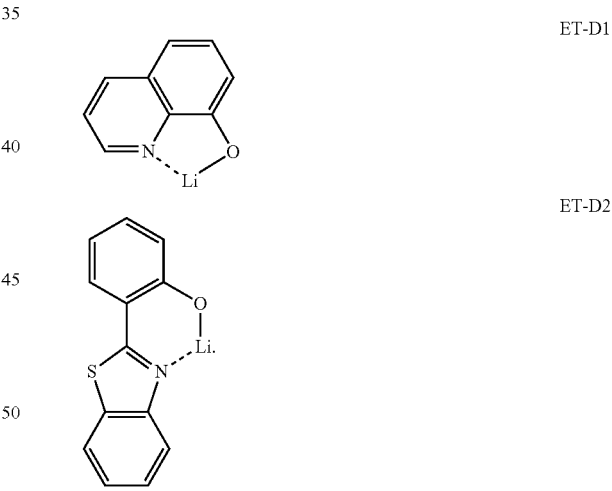

ET-D1

ET-D2

The electron transport region may include an electron injection layer that facilitates electron injection from the second electrode 190. The electron injection layer may be in direct contact with the second electrode 190.

The electron injection layer may have i) a single-layered structure including a single layer including a single material, ii) a single-layered structure including a single layer including a plurality of different materials, or iii) a multi-layered structure having a plurality of layers including a plurality of different materials.

The electron injection layer may include an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combination thereof.

The alkali metal may be selected from Li, Na, K, Rb, and Cs. In one embodiment, the alkali metal may be Li, Na, and/or Cs. In one or more embodiments, the alkali metal may be Li and/or Cs, but embodiments of the present disclosure are not limited thereto.

The alkaline earth metal may be selected from Mg, Ca, Sr, and Ba.

The rare earth metal may be selected from Sc, Y, Ce, Tb, Yb, and Gd.

The alkali metal compound, the alkaline earth-metal compound, and the rare earth metal compound may be selected from oxides and halides (for example, fluorides, chlorides, bromides, and/or iodides) of the alkali metal, the alkaline earth-metal, and the rare earth metal, respectively.

The alkali metal compound may be selected from alkali metal oxides (such as $Li_2O$, $Cs_2O$, and/or $K_2O$), and alkali metal halides (such as LiF, NaF, CsF, KF, LiI, NaI, CsI, and/or KI). In one embodiment, the alkali metal compound may be selected from LiF, $Li_2O$, NaF, LiI, NaI, CsI, and KI, but embodiments of the present disclosure are not limited thereto.

The alkaline earth-metal compound may be selected from alkaline earth-metal oxides, such as BaO, SrO, CaO, $Ba_xSr_{1-x}O$ (0<x<1), and/or $Ba_xCa_{1-x}O$ (0<x<1). In one embodiment, the alkaline earth-metal compound may be selected from BaO, SrO, and CaO, but embodiments of the present disclosure are not limited thereto.

The rare earth metal compound may be selected from $YbF_3$, $ScF_3$, $ScO_3$, $Y_2O_3$, $Ce_2O_3$, $GdF_3$ and $TbF_3$. In one embodiment, the rare earth metal compound may be selected from $YbF_3$, $ScF_3$, $TbF_3$, $YbI_3$, $ScI_3$, and $TbI_3$, but embodiments of the present disclosure are not limited thereto.

The alkali metal complex, the alkaline earth-metal complex, and the rare earth metal complex may respectively include an ion of alkali metal, alkaline earth-metal, and rare earth metal as described above, and a ligand coordinated with a metal ion of the alkali metal complex, the alkaline earth-metal complex, or the rare earth metal complex may be selected from hydroxy quinoline, hydroxy isoquinoline, hydroxy benzoquinoline, hydroxy acridine, hydroxy phenanthridine, hydroxy phenyloxazole, hydroxy phenylthiazole, hydroxy diphenyloxadiazole, hydroxy diphenylthiadiazole, hydroxy phenylpyridine, hydroxy phenylbenzimidazole, hydroxy phenylbenzothiazole, bipyridine, phenanthroline, and cyclopentadiene, but embodiments of the present disclosure are not limited thereto.

The electron injection layer may include (e.g., may consist of) an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combination thereof, as described above. In one or more embodiments, the electron injection layer may further include an organic material. When the electron injection layer further includes an organic material, the alkali metal, the alkaline earth metal, the rare earth metal, the alkali metal compound, the alkaline earth-metal compound, the rare earth metal compound, the alkali metal complex, the alkaline earth-metal complex, the rare earth metal complex, or any combination thereof may be homogeneously or non-homogeneously dispersed in a matrix including the organic material.

A thickness of the electron injection layer may be in a range of about 1 Å to about 100 Å, for example, about 3 Å to about 90 Å. When the thickness of the electron injection layer is within the range described above, the electron injection layer may have satisfactory (suitable) electron injection characteristics without a substantial increase in driving voltage.

Second Electrode 190

The second electrode 190 may be disposed on the organic layer 150 having the structure according to embodiments of the present disclosure. The second electrode 190 may be a cathode, which is an electron injection electrode, and in this regard, a material to form the second electrode 190 may be selected from a metal, an alloy, an electrically conductive compound, and combinations thereof, which have a relatively low work function.

The second electrode 190 may include at least one selected from lithium ($L_i$), silver (Ag), magnesium (Mg), aluminum (Al), aluminum-lithium (Al—Li), calcium (Ca), magnesium-indium (Mg—In), magnesium-silver (Mg—Ag), ITO, and IZO, but embodiments of the present disclosure are not limited thereto. The second electrode 190 may be a transmissive electrode, a semi-transmissive electrode, or a reflective electrode.

The second electrode 190 may have a single-layered structure, or a multi-layered structure including two or more layers.

Figure 3:
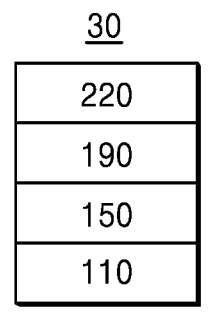
Figure 4:
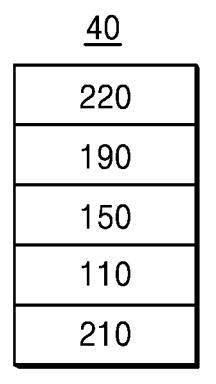

Description of FIGS. 2 to 4

Figure 2:
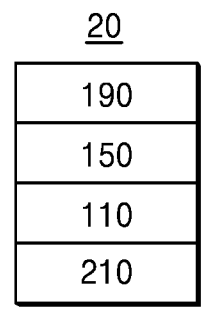

FIG. 2 is a schematic view of an organic light-emitting device 20 according to an embodiment. The organic light-emitting device 20 includes a first capping layer 210, the first electrode 110, the organic layer 150, and the second electrode 190, which are sequentially stacked in this stated order. FIG. 3 is a schematic view of an organic light-emitting device 30 according to an embodiment. The organic light-emitting device 30 includes the first electrode 110, the organic layer 150, the second electrode 190, and a second capping layer 220, which are sequentially stacked in this stated order. FIG. 4 is a schematic view of an organic light-emitting device 40 according to an embodiment. The organic light-emitting device 40 includes the first capping layer 210, the first electrode 110, the organic layer 150, the second electrode 190, and the second capping layer 220, which are sequentially stacked in this stated order.

Regarding FIGS. 2 to 4, the first electrode 110, the organic layer 150, and the second electrode 190 may each be understood by referring to the descriptions thereof presented in connection with FIG. 1.

In the organic layer 150 of each of the organic light-emitting devices 20 and 40, light generated in an emission layer may pass through the first electrode 110 and the first capping layer 210 toward the outside, wherein the first electrode 110 may be a semi-transmissive electrode or a transmissive electrode.

The first capping layer 210 and the second capping layer 220 may increase external luminescent efficiency according to the principle of constructive interference.

The first capping layer 210 and the second capping layer 220 may each independently be an organic capping layer including an organic material, an inorganic capping layer including an inorganic material, or a composite capping layer including an organic material and an inorganic material. The organic capping layer may include polyethylene tetephthalate, polyethylene naphthalate, polycarbonate, polyimide, polyethylene sulfonate, polyoxymethylene, polyarylate, hexamethyldisiloxane, acryl-based resin (e.g., polymethylmethacrylate, polyacrylic acid, etc), or any combination thereof.

At least one selected from the first capping layer 210 and the second capping layer 220 may each independently include at least one material selected from carbocyclic compounds, heterocyclic compounds, amine-based compounds, porphyrine derivatives, phthalocyanine derivatives, naphthalocyanine derivatives, alkali metal complexes, and alkaline earth-based complexes. The carbocyclic compound, the heterocyclic compound, and/or the amine-based compound may be optionally substituted with a substituent containing at least one element selected from O, N, S, Se, Si, F, Cl, Br, and I. In one embodiment, at least one selected from the first capping layer 210 and the second capping layer 220 may each independently include an amine-based compound.

In one embodiment, at least one selected from the first capping layer 210 and the second capping layer 220 may each independently include a compound represented by Formula 201 or a compound represented by Formula 202.

In one or more embodiments, at least one selected from the first capping layer 210 and the second capping layer 220 may each independently include a compound selected from Compounds HT28 to HT33 and Compounds CP1 to CP5, but embodiments of the present disclosure are not limited thereto:

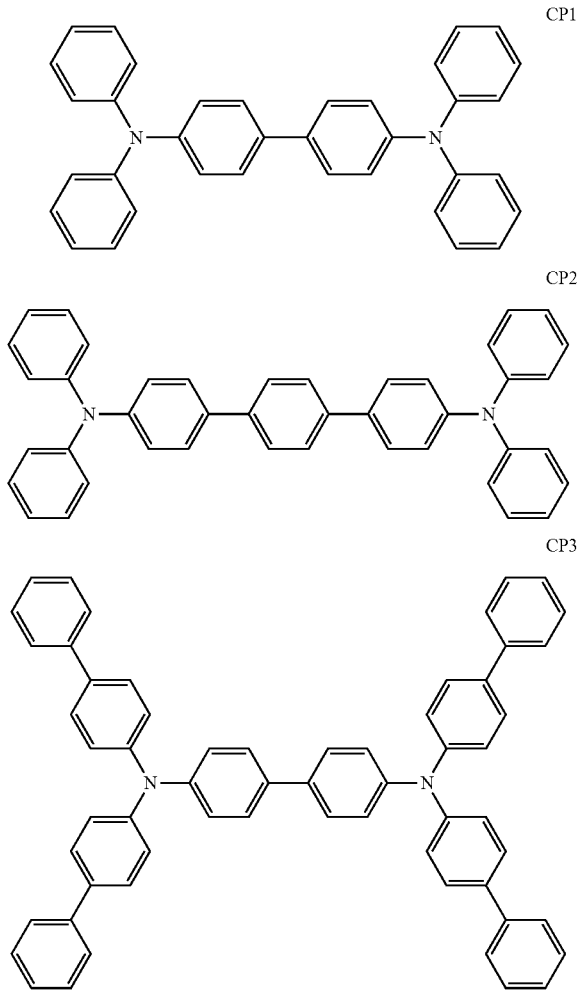

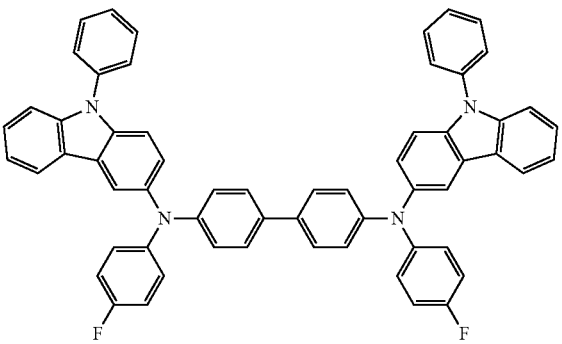

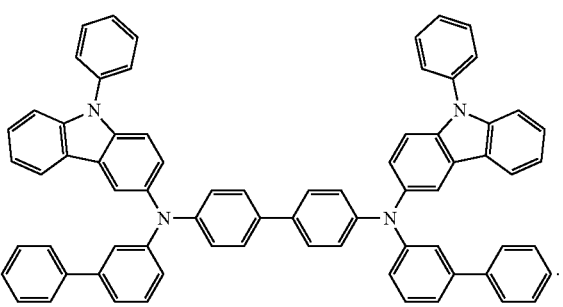

Hereinbefore, the organic light-emitting device according to an embodiment has been described in connection with FIGS. 1 to 4, but embodiments of the present disclosure are not limited thereto.

Layers constituting the hole transport region, the emission layer, and layers constituting the electron transport region may be formed in a certain region by using one or more suitable methods selected from vacuum deposition, spin coating, casting, Langmuir-Blodgett (LB) deposition, ink-jet printing, laser-printing, and laser-induced thermal imaging.

When layers constituting the hole transport region, the emission layer, and layers constituting the electron transport region are formed by vacuum deposition, the deposition may be performed at a deposition temperature of about 100° C. to about 500° C., a vacuum degree of about $10^{-8}$ torr to about $10^{-3}$ torr, and a deposition speed of about 0.01 Å/sec to about 100 Å/sec by taking into account a material to be included in a layer to be formed, and the structure of a layer to be formed.

When layers constituting the hole transport region, the emission layer, and layers constituting the electron transport region are formed by spin coating, the spin coating may be performed at a coating speed of about 2,000 rpm to about 5,000 rpm and at a heat treatment temperature of about 80° C. to 200° C. by taking into account a material to be included in a layer to be formed, and the structure of a layer to be formed.

Apparatus

The organic light-emitting device may be included in various suitable apparatuses. For example, a light-emitting apparatus, an authentication apparatus, and/or an electronic apparatus, which includes the organic light-emitting device, may be provided.

The light-emitting apparatus may further include, in addition to the organic light-emitting device, a thin film transistor including a source electrode and a drain electrode. One of the source electrode and the drain electrode of the thin film transistor may be electrically connected to one of the first electrode and the second electrode of the organic light-emitting device. The light-emitting apparatus may be used as various suitable displays, light sources, and/or the like.

The authentication apparatus may be, for example, a biometric authentication apparatus for authenticating an individual by using biometric information of a biometric body (for example, a finger tip, a pupil, and/or the like).

The authentication apparatus may further include, in addition to the organic light-emitting device, a biometric information collector.

The electronic apparatus may be applied to personal computers (for example, a mobile personal computer), mobile phones, digital cameras, electronic organizers, electronic dictionaries, electronic game machines, medical instruments (for example, electronic thermometers, sphygmomanometers, blood glucose meters, pulse measurement devices, pulse wave measurement devices, electrocardiogram (ECG) displays, ultrasonic diagnostic devices, and/or endoscope displays), fish finders, various measuring instruments, meters (for example, meters for a vehicle, an aircraft, and/or a vessel), projectors, and/or the like, but embodiments of the present disclosure are not limited thereto.

General Definition of Substituents

The term "$C_1$-$C_{60}$ alkyl group" as used herein may refer to a linear or branched aliphatic saturated hydrocarbon monovalent group having 1 to 60 carbon atoms, and non-limiting examples thereof include a methyl group, an ethyl group, a propyl group, an isobutyl group, a sec-butyl group, a tert-butyl group, a pentyl group, an isoamyl group, and a hexyl group. The term "$C_1$-$C_{60}$ alkylene group" as used herein may refer to a divalent group having the same structure as the $C_1$-$C_{60}$ alkyl group.

The term "$C_2$-$C_{60}$ alkenyl group" as used herein may refer to a hydrocarbon group having at least one carbon-carbon double bond at one or more positions along the hydrocarbon chain of the $C_2$-$C_{60}$ alkyl group (e.g., in the middle and/or at the terminus of the $C_2$-$C_{60}$ alkyl group), and non-limiting examples thereof include an ethenyl group, a propenyl group, and a butenyl group. The term "$C_2$-$C_{60}$ alkenylene group" as used herein may refer to a divalent group having the same structure as the $C_2$-$C_{60}$ alkenyl group.

The term "$C_2$-$C_{60}$ alkynyl group" as used herein may refer to a hydrocarbon group having at least one carbon-carbon triple bond at one or more positions along the hydrocarbon chain of the $C_2$-$C_{60}$ alkyl group (e.g., in the middle and/or at the terminus of the $C_2$-$C_{60}$ alkyl group), and non-limiting examples thereof include an ethynyl group, and a propynyl group. The term "$C_2$-$C_{60}$ alkynylene group" as used herein may refer to a divalent group having the same structure as the $C_2$-$C_{60}$ alkynyl group.

The term "$C_1$-$C_{60}$ alkoxy group" as used herein may refer to a monovalent group represented by —$OA_{101}$ (wherein $A_{101}$ is the $C_1$-$C_{60}$ alkyl group), and non-limiting examples thereof include a methoxy group, an ethoxy group, and an isopropyloxy group.

The term "$C_3$-$C_{10}$ cycloalkyl group" as used herein may refer to a monovalent saturated hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. The term "$C_3$-$C_{10}$ cycloalkylene group" as used herein may refer to a divalent group having the same structure as the $C_3$-$C_{10}$ cycloalkyl group.

The term "$C_1$-$C_{10}$ heterocycloalkyl group" as used herein may refer to a monovalent monocyclic group having at least one heteroatom selected from N, O, Si, P, and S as a ring-forming atom and 1 to 10 carbon atoms as the remaining ring-forming atoms, and non-limiting examples thereof include a 1,2,3,4-oxatriazolidinyl group, a tetrahydrofuranyl group, and a tetrahydrothiophenyl group. The term "$C_1$-$C_{10}$ heterocycloalkylene group" as used herein may refer to a divalent group having the same structure as the $C_1$-$C_{10}$ heterocycloalkyl group.

The term $C_3$-$C_{10}$ cycloalkenyl group used herein may refer to a monovalent monocyclic group that has 3 to 10 carbon atoms and at least one carbon-carbon double bond in the ring thereof and no aromaticity, and non-limiting examples thereof include a cyclopentenyl group, a cyclohexenyl group, and a cycloheptenyl group. The term "$C_3$-$C_{10}$ cycloalkenylene group" as used herein may refer to a divalent group having the same structure as the $C_3$-$C_{10}$ cycloalkenyl group.

The term "$C_1$-$C_{10}$ heterocycloalkenyl group" as used herein may refer to a monovalent monocyclic group that has at least one heteroatom selected from N, O, Si, P, and S as a ring-forming atom, 1 to 10 carbon atoms as the remaining ring-forming atoms, and at least one carbon-carbon double bond in its ring. Non-limiting examples of the $C_1$-$C_{10}$ heterocycloalkenyl group include a 4,5-dihydro-1,2,3,4-oxatriazolylgroup, a 2,3-dihydrofuranyl group, and a 2,3-dihydrothiophenyl group. The term "$C_1$-$C_{10}$ heterocycloalkenylene group" as used herein may refer to a divalent group having the same structure as the $C_1$-$C_{10}$ heterocycloalkenyl group.

The term "$C_6$-$C_{60}$ aryl group" as used herein may refer to a monovalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. The term "$C_6$-$C_{60}$ arylene group" used herein may refer to a divalent group having the same structure as the $C_6$-$C_{60}$ aryl group. When the $C_6$-$C_{60}$ aryl group and the $C_6$-$C_{60}$ arylene group each independently include two or more rings, the respective rings may be fused to each other.

The term "$C_1$-$C_{60}$ heteroaryl group" as used herein may refer to a monovalent group having a carbocyclic aromatic system that has at least one heteroatom selected from N, O, Si, P, and S as a ring-forming atom, in addition to 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. The term "$C_1$-$C_{60}$ heteroarylene group" as used herein may refer to a divalent group having the same structure as the $C_1$-$C_{60}$ heteroaryl group. When the $C_1$-$C_{60}$ heteroaryl group and the $C_1$-$C_{60}$ heteroarylene group each independently include two or more rings, the respective rings may be condensed with each other.

The term "$C_6$-$C_{60}$ aryloxy group" as used herein may refer to a group represented by —$OA_{102}$ (wherein $A_{102}$ is the $C_6$-$C_{60}$ aryl group), and a $C_6$-$C_{60}$ arylthio group used herein may refer to a group represented by —$SA_{103}$ (wherein $A_{103}$ is the $C_6$-$C_{60}$ aryl group).

The term "monovalent non-aromatic condensed polycyclic group" as used herein may refer to a monovalent group having two or more rings condensed with each other, only carbon atoms as ring-forming atoms (for example, having 8 to 60 carbon atoms), and no aromaticity in its entire molecular structure. A non-limiting example of the monovalent non-aromatic condensed polycyclic group is a fluorenyl group. The term "divalent non-aromatic condensed polycyclic group" as used herein may refer to a divalent group having the same structure as the monovalent non-aromatic condensed polycyclic group.

The term "monovalent non-aromatic condensed heteropolycyclic group" as used herein may refer to a monovalent group having two or more rings condensed to each other, at least one heteroatom selected from N, O, Si, P, and S, other than carbon atoms (for example, 1 to 60 carbon atoms), as a ring-forming atom, and no aromaticity in its entire molecular structure. A non-limiting example of the monovalent non-aromatic condensed heteropolycyclic group is a carbazolyl group. The term "divalent non-aromatic condensed heteropolycyclic group" as used herein may refer to a divalent group having the same structure as the monovalent non-aromatic condensed heteropolycyclic group.

The term "$C_4$-$C_{60}$ carbocyclic group" as used herein may refer to a monocyclic or polycyclic group having 4 to 60 carbon atoms in which a ring-forming atom is a carbon atom only. The term "$C_4$-$C_{60}$ carbocyclic group" as used herein may refer to an aromatic carbocyclic group or a non-aromatic carbocyclic group. The $C_4$-$C_{60}$ carbocyclic group may be a ring (such as benzene), a monovalent group (such as a phenyl group), or a divalent group (such as a phenylene group). In one or more embodiments, depending on the number of substituents connected to the $C_4$-$C_{60}$ carbocyclic group, the $C_4$-$C_{60}$ carbocyclic group may be a trivalent group or a quadrivalent group.

The term "$C_1$-$C_{60}$ heterocyclic group" as used herein may refer to a group having the same structure as the $C_4$-$C_{60}$ carbocyclic group, except that as a ring-forming atom, at least one heteroatom selected from N, O, Si, P, and S is used in addition to carbon atoms (the number of carbon atoms may be in a range of 1 to 60).

In the present specification, at least one substituent of the substituted $C_4$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($C_{211}$)($C_{212}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a $C_1$-$C_{60}$ alkyl group substituted with at least one selected from deuterium, —F, and a cyano group, a $C_6$-$C_{60}$ aryl group substituted with at least one selected from deuterium, —F, and a cyano group, a biphenyl group, and a terphenyl group.

The term "Ph" as used herein may refer to a phenyl group, the term "Me" as used herein may refer to a methyl group, the term "Et" as used herein may refer to an ethyl group, the term "ter-Bu" or "But" as used herein may refer to a tert-butyl group, the term "OMe" as used herein may refer to a methoxy group, and "D" may refer to deuterium.

The term "biphenyl group" as used herein may refer to "a phenyl group substituted with a phenyl group". In other words, the "biphenyl group" may be a substituted phenyl group having a $C_6$-$C_{60}$ aryl group as a substituent.

The term "terphenyl group" as used herein may refer to "a phenyl group substituted with a biphenyl group". In other words, the "terphenyl group" may be a phenyl group having, as a substituent, a $C_6$-$C_{60}$ aryl group substituted with a $C_6$-$C_{60}$ aryl group.

and *' as used herein, unless defined otherwise, each refer to a binding site to a neighboring atom in a corresponding formula.

Hereinafter, a compound according to embodiments and an organic light-emitting device according to embodiments will be described in more detail with reference to Synthesis Examples and Examples. The wording "B was used instead of A" used in describing Synthesis Examples may refer to an identical molar equivalent of B being used in place of A.

EXAMPLES

Synthesis Example: Synthesis of Compounds

Synthesis of Compound 1
Synthesis of Intermediate A

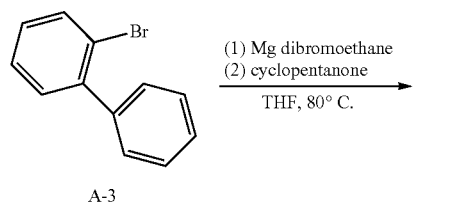

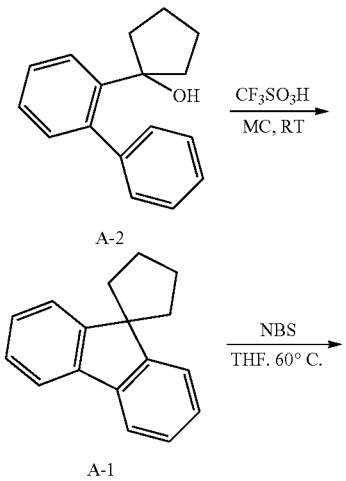

To a two-neck flask dried in an oven, magnesium (Mg) (3.49 g), dibromoethane (1.44 g), and tetrahydrofuran (THF) (100 ml) were added. The reaction solution was stirred, and then, Compound A-3 (35 g) was added thereto.

After the stirring, the reaction temperature was lowered to room temperature, and the reaction solution was slowly added to a cyclopentanone (12.75 g) solution dissolved in THF (300 ml), and then, was stirred again at a temperature of 80° C. for 12 hours. The reaction temperature was lowered to room temperature, and the reaction was terminated by using water. Then, an extraction process was performed thereon three times by using ethylether. An organic layer extracted therefrom was dried by using anhydrous magnesium sulfate, and a residue obtained by decompression was separated and purified by using column chromatography, thereby obtaining Intermediate A-2 (13.53 g, yield: 46%).

CF$_3$SO$_3$H (8.53 g) was slowly added to Intermediate A-2 (13.53 g) dissolved in methylenechloride (MC), and the reaction solution was stirred for 1 hour. The reaction was terminated by using water, and an extraction process was performed thereon three times by using MC. An organic layer extracted therefrom was dried by using anhydrous magnesium sulfate, and a residue obtained by decompression was separated and purified by using column chromatography, thereby obtaining Intermediate A-1 (4.38 g, yield: 35%).

NBS (4.22 g) was added to Intermediate A-1 (4.38 g) dissolved in THF, and the reaction solution was heated at a temperature of 60° C. and stirred for 3 hours. The reaction temperature was lowered to room temperature, and the reaction was terminated by using water. Then, an extraction process was performed thereon three times by using ethylether. An organic layer extracted therefrom was dried by using anhydrous magnesium sulfate, and a residue obtained by decompression was separated and purified by using column chromatography, thereby obtaining Intermediate A (4.51 g, yield: 76%).

(2) Synthesis of Compound 1

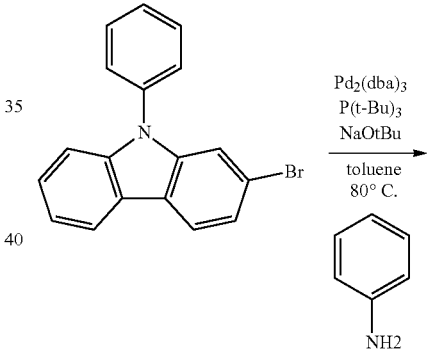

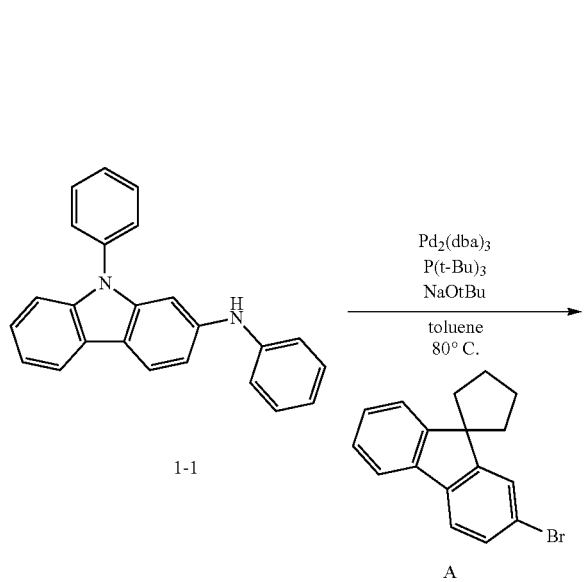

-continued

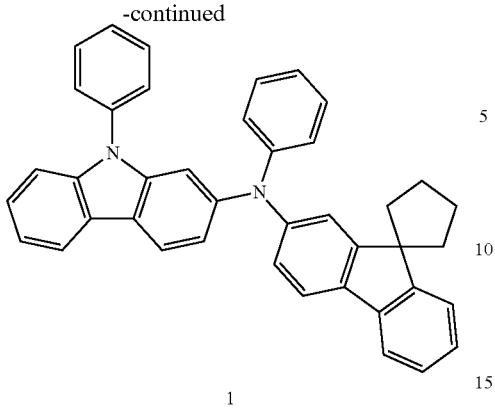

1

-continued

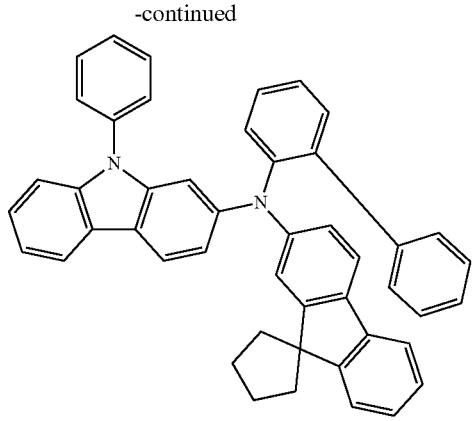

3

2-bromo-9-phenyl-9H-carbazole (4.74 g) and aniline (1.99 g), Pd$_2$(dba)$_3$ (1.35 g), P(t-Bu)$_3$ (0.30 g), and NaOtBu (4.26 g) were dissolved in toluene (80 ml), and the reaction solution was stirred at a temperature of 80° C. for 1 hour. The reaction temperature was lowered to room temperature, and the reaction was terminated by using water. Then, an extraction process was performed thereon three times by using ethylether. An organic layer extracted therefrom was dried by using anhydrous magnesium sulfate, and a residue obtained by decompression was separated and purified by using column chromatography, thereby obtaining Intermediate 1-1 (3.48 g, yield: 70%). Compound 1 (3.76 g, yield: 65%) was obtained in the same (or substantially the same) manner as in the synthesis of Intermediate 1-1, except that Intermediate 1-1 (3.48 g) was used instead of 2-bromo-9-phenyl-9H-carbazole, and Intermediate A (3.07 g) was used instead of aniline.

2. Synthesis of Compound 3

Compound 3 (2.81 g, yield: 57%) was obtained in the same (or substantially the same) manner as in the synthesis of Compound 1, except that 2-aminobiphenyl (3.28 g) was used instead of aniline.

3. Synthesis of Compound 4

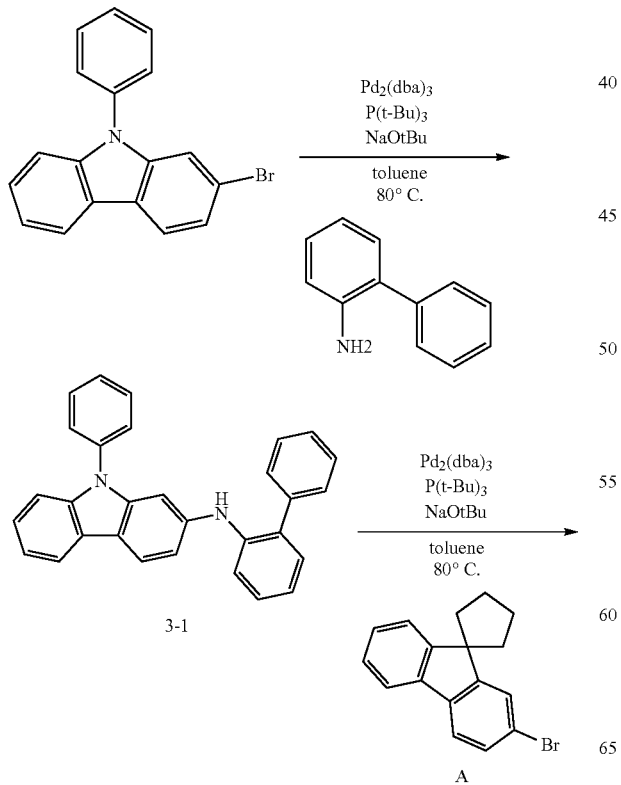

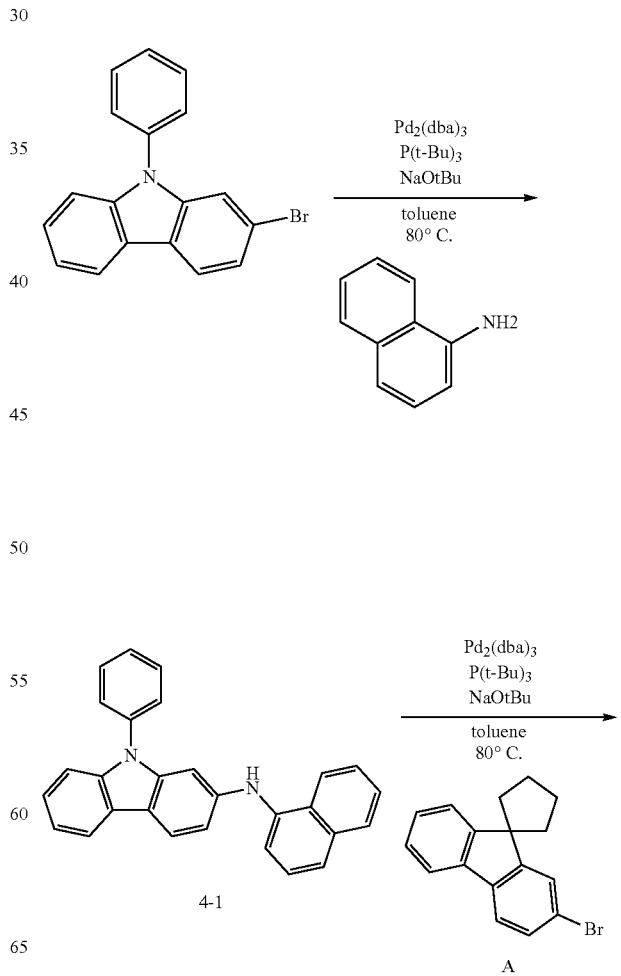

109

-continued

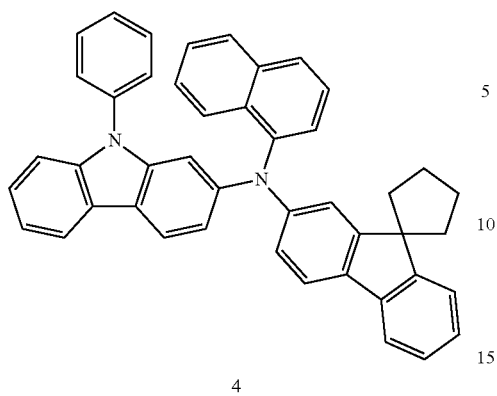

4

Compound 4 (3.05 g, yield: 63%) was obtained in the same (or substantially the same) manner as in the synthesis of Compound 3, except that 1-aminonaphthalene (2.30 g) was used instead of 2-aminobiphenyl.

4. Synthesis of Compound 11

110

-continued

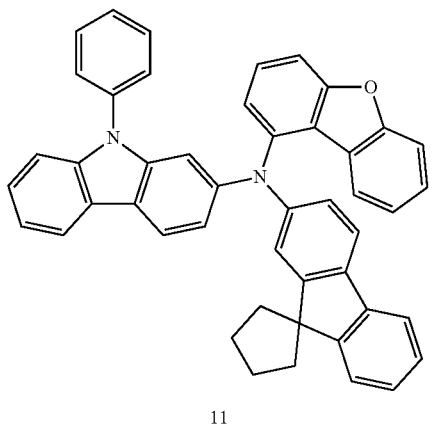

11

Compound 11 (2.11 g, yield: 54%) was obtained in the same (or substantially the same) manner as in the synthesis of Compound 4, except that 1-aminodibenzofuran (2.22 g) was used instead of 1-aminonaphthalene.

5. Synthesis of Compound 15

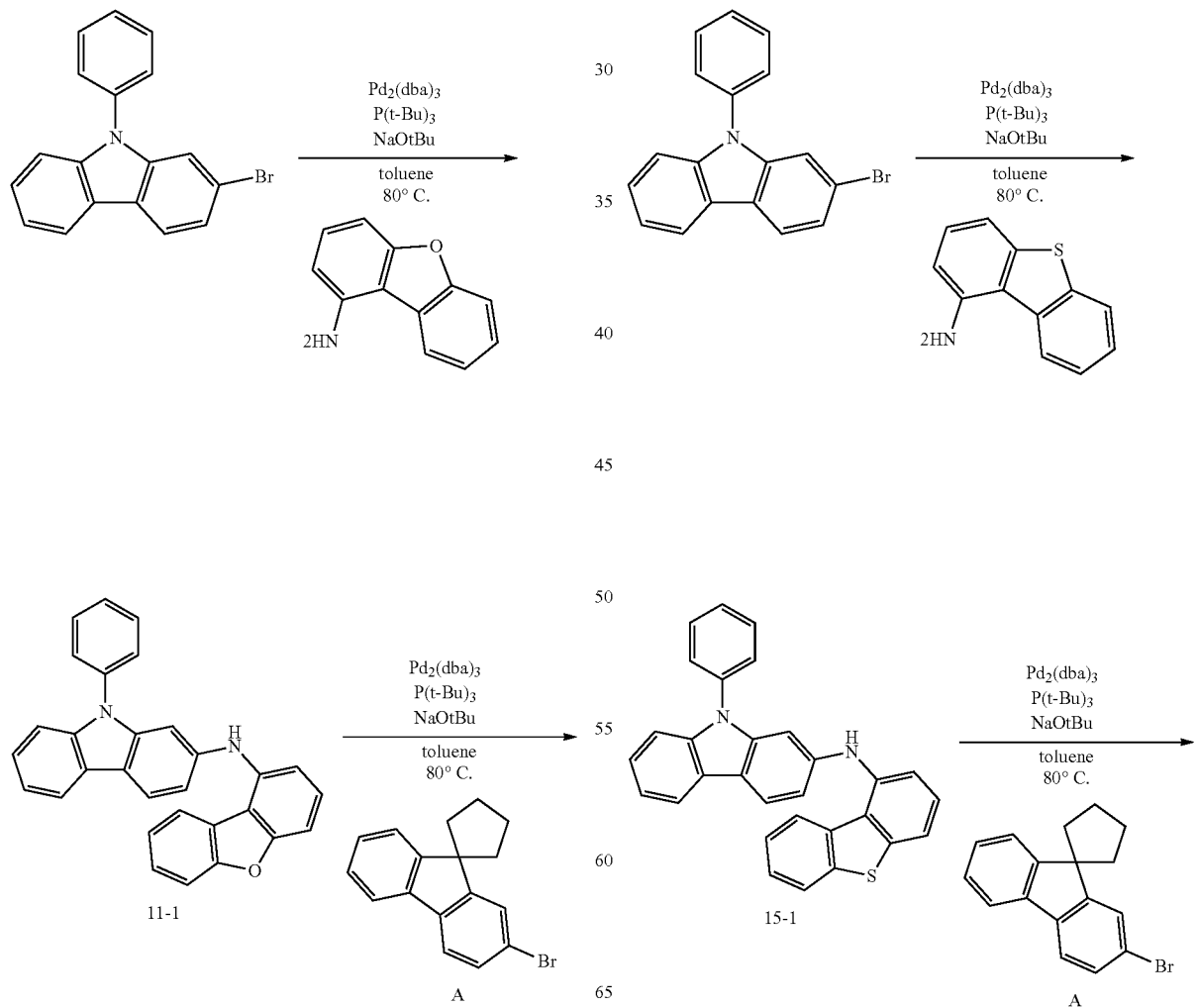

-continued

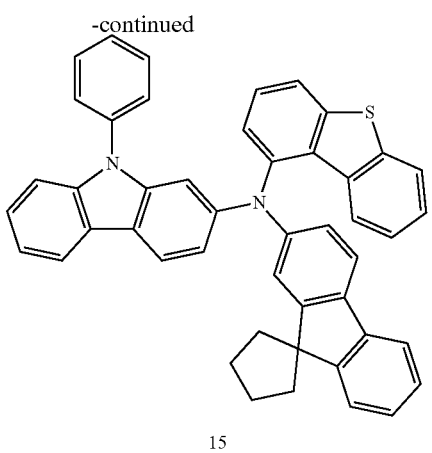

15

Compound 15 (2.74 g, yield: 63%) was obtained in the same (or substantially the same) manner as in the synthesis of Compound 11, except that 1-aminodibenzothiophene (2.63 g) was used instead of 1-aminodibenzofuran.

6. Synthesis of Compound 20
(1) Synthesis of Compound B

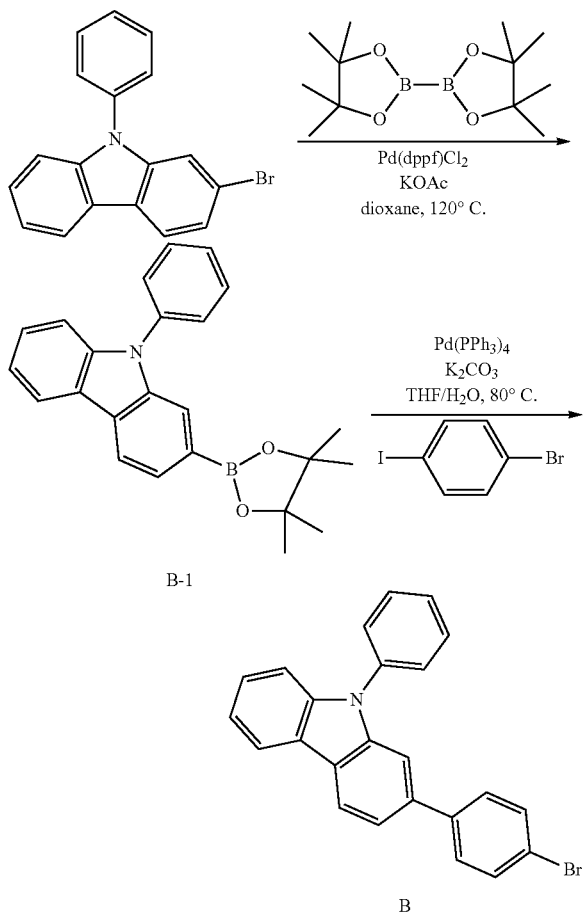

2-bromo-9-phenyl-9H-carbazole (6.97 g), Pd(dppf)Cl$_2$ (0.79 g), KOAc (5.27 g), and bispinacolatodiboron (5.48 g) were dissolved in dioxane (100 ml), and the reaction solution was stirred at a temperature of 120° C. for 12 hours. The reaction temperature was lowered to room temperature, and the reaction was terminated by using water. Then, an extraction process was performed thereon three times by using MC. An organic layer extracted therefrom was dried by using anhydrous magnesium sulfate, and a residue obtained by decompression was separated and purified by using column chromatography, thereby obtaining Intermediate B-1 (6.45 g, yield: 81%).

Intermediate B-1 (6.45 g), Pd(PPh$_3$)$_4$ (1.00 g), K$_2$CO$_3$ (6.72 g), and 1-bromo-4-iodobenzene (4.91 g) were dissolved in THF/H$_2$O (100 ml/25 ml), and the reaction solution was stirred at a temperature of 80° C. for 12 hours. The reaction temperature was lowered to room temperature, and the reaction was terminated by using water. Then, an extraction process was performed thereon three times by using ethylether. An organic layer extracted therefrom was dried by using anhydrous magnesium sulfate, and a residue obtained by decompression was separated and purified by using column chromatography, thereby obtaining Compound B (4.65 g, yield: 67%).

(2) Synthesis of Compound 20

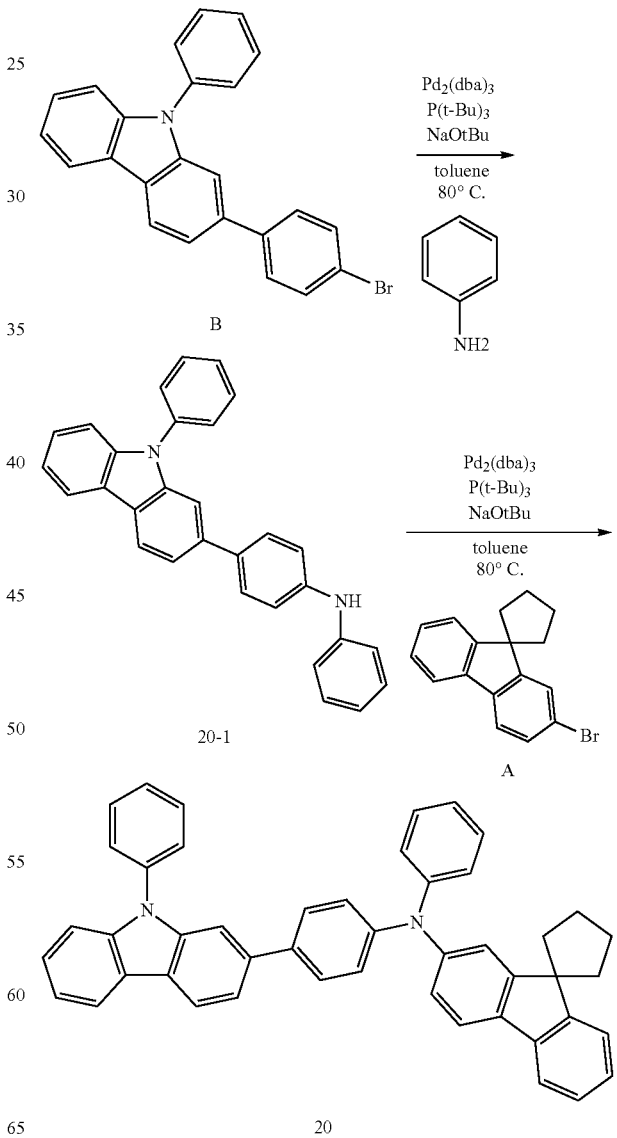

20

Compound B (4.25 g), aniline (1.39 g), Pd$_2$(dba)$_3$ (0.97 g), P(t-Bu)$_3$ (0.21 g), and NaOtBu (3.08 g) were dissolved in toluene (80 ml), and the reaction solution was stirred at a temperature of 80° C. for 1 hour. The reaction temperature was lowered to room temperature, and the reaction was terminated by using water. Then, an extraction process was performed thereon three times by using ethylether. An organic layer extracted therefrom was dried by using anhydrous magnesium sulfate, and a residue obtained by decompression was separated and purified by using column chromatography, thereby obtaining Intermediate 20-1 (3.34 g, yield: 76%). Compound 20 (4.1 g, yield: 81%) was obtained in the same (or substantially the same) manner as in the synthesis of Intermediate 1-1, except that Intermediate 20-1 (3.34 g) was used instead of 2-bromo-9-phenyl-9H-carbazole, and Intermediate A (6.15 g) was instead of aniline.

7. Synthesis of Compound 22

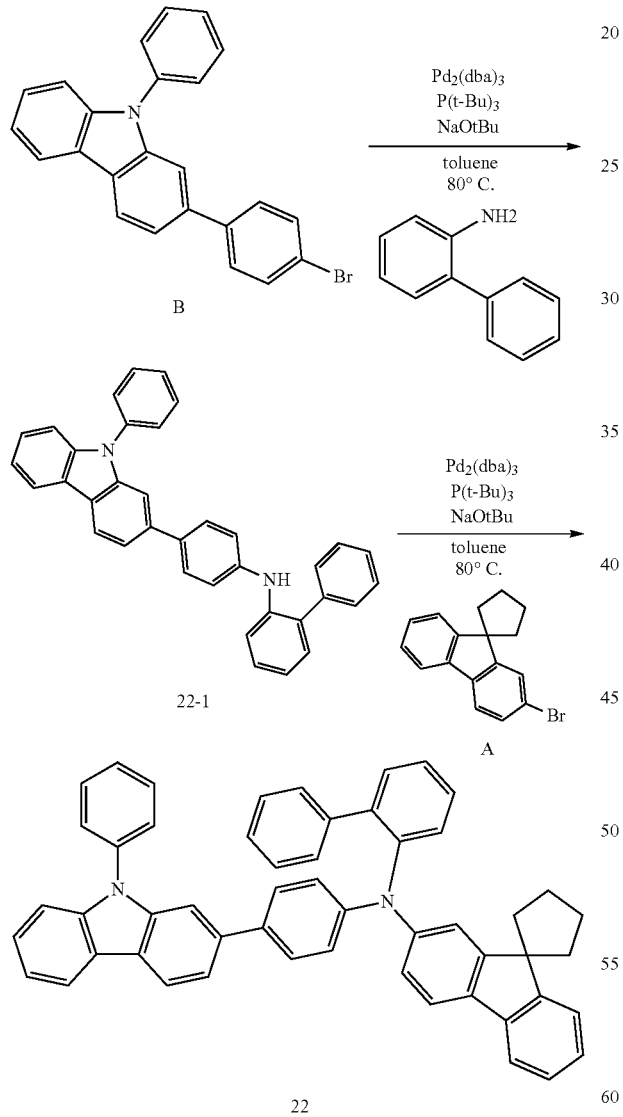

Compound 22 (2.41 g, yield: 64%) was obtained in the same (or substantially the same) manner as in the synthesis of Compound 20, except that 2-aminobiphenyl (1.8 g) was used instead of aniline to produce Intermediate 22-1, and Intermediate 22-1 was used instead of Intermediate 20-1.

8. Synthesis of Compound 23

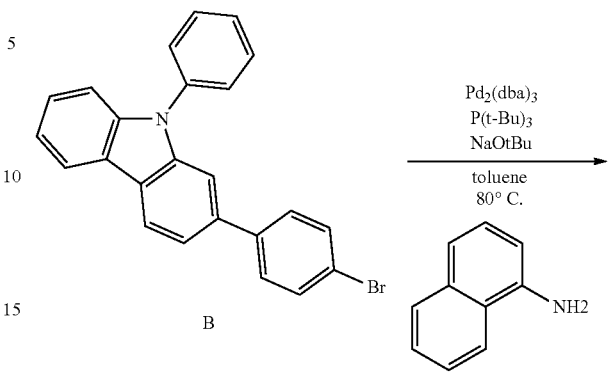

Compound 23 (2.52 g, yield: 71%) was obtained in the same (or substantially the same) manner as in the synthesis of Compound 22, except that 1-aminonaphthalene (2.12 g) was used instead of 2-aminobiphenyl to produce Intermediate 23-1, and Intermediate 23-1 was used instead of Intermediate 22-1.

9. Synthesis of Compound 30
10. Synthesis of Compound 34
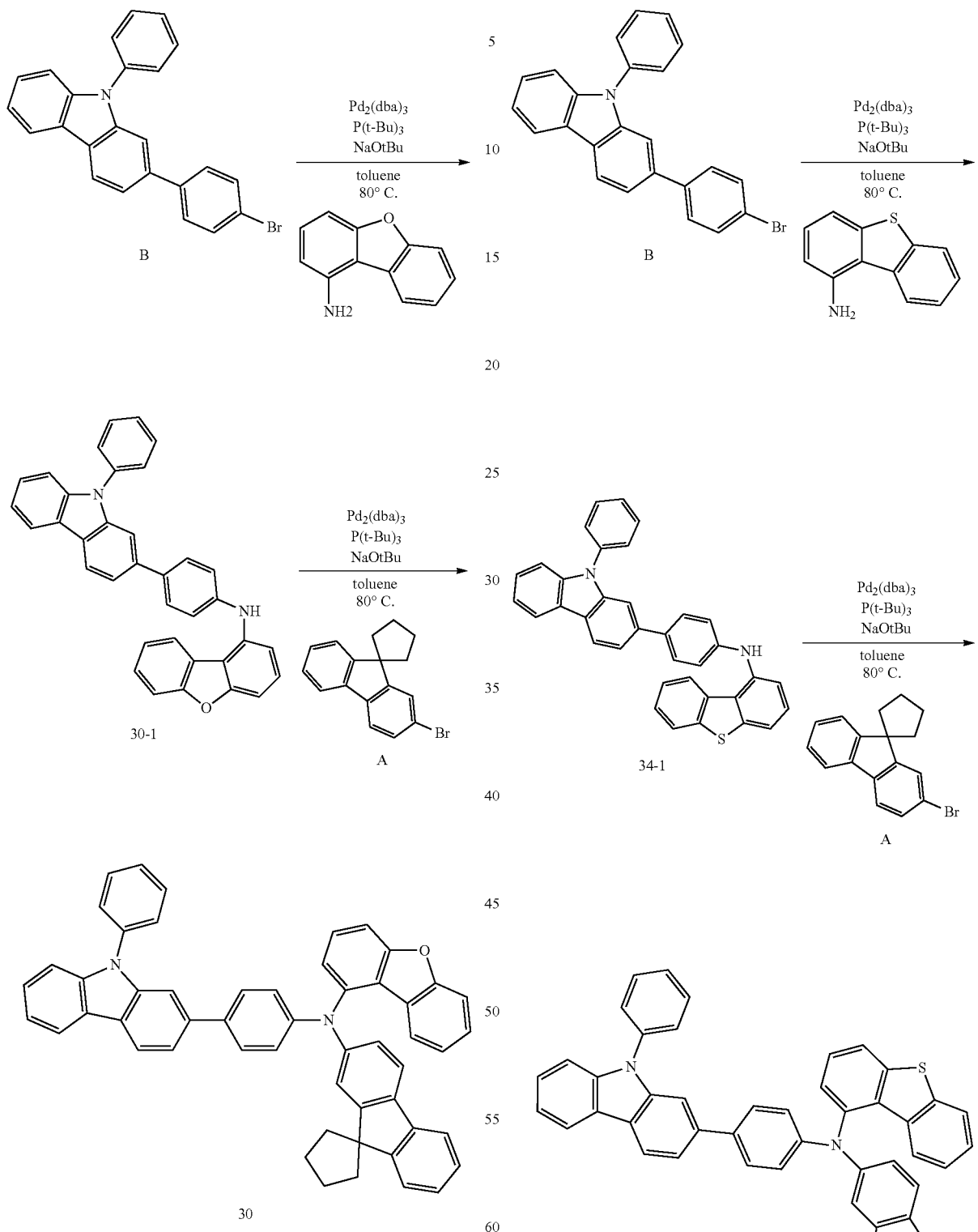
Compound 30 (2.34 g, yield: 64%) was obtained in the same (or substantially the same) manner as in the synthesis of Compound 23, except that 1-aminodibenzofuran (1.86 g) was used instead of 1-aminonaphthalene to produce Intermediate 30-1, and Intermediate 30-1 was used instead of Intermediate 23-1.

Compound 34 (2.71 g, yield: 81%) was obtained in the same (or substantially the same) manner as in the synthesis of Compound 30, except that 1-aminodibenzothiophene (1.84 g) was used instead of 1-aminodibenzofuran to produce Intermediate 34-1, and Intermediate 34-1 was used instead of Intermediate 30-1.

The compounds synthesized according to Synthesis Examples above were identified by $^1$H NMR and MS/FAB, and results are shown in Table 1 below.

Synthesis routes of compounds other than the compounds shown in Table 1 should be readily recognized by one of ordinary skill in the art by referring to the synthesis routes and the raw materials above.

On the glass substrate, first, 2-TNATA was vacuum-deposited to form a hole injection layer having a thickness of 600 Å, and 4,4'-bis[N-(1-naphthyl)-N-phenylamino]biphenyl (hereinafter, referred to as NPB), which is a hole transport material, was vacuum-deposited as a hole transport compound to form a hole transport layer having a thickness of 300 Å.

9,10-di(naphthalen-2-yl)anthracene (hereinafter, referred to as DNA), which is a blue fluorescence host, and 4,4'-bis[2-(4-(N,N-diphenylamino)phenyl)vinyl]biphenyl (hereinafter, referred to as DPAVBi), which is a blue phosphorescence dopant compound, were co-deposited on the hole transport layer at a weight ratio of 98:2 to form an emission layer having a thickness of 300 Å.

Next, Alq$_3$ was deposited on the emission layer to form an electron transport having a thickness of 300 Å, LiF (which is a halogenated alkali metal) was deposited on the electron transport layer to form an electron injection layer having a thickness of 10 Å, and Al was deposited as a cathode electrode on the electron injection layer to form a cathode having a thickness of 3,000 Å (to thereby form a LiF/Al electrode), thereby completing the manufacture of an organic light-emitting device.

TABLE 1

| Compound | $^1$H NMR (CDCl$_3$, 400 MHz) | MS/FAB found | MS/FAB calc. |
| --- | --- | --- | --- |
| 1 | 8.55 (d, 1H), 8.22 (d, 1H), 7.94-7.86 (m, 3H), 7.62-7.50 (m, 6H), 7.35-7.00 (m, 13H), 2.21-1.96 (m, 4H), 1.73-1.63 (m, 4H) | 553.26 | 552.26 |
| 3 | 8.55 (d, 1H), 8.24 (d, 1H), 8.10 (d, 1H), 7.94-7.86 (m, 3H), 7.62-7.08 (m, 22H), 2.21-1.96 (m, 4H), 1.73-1.63 (m, 4H) | 629.29 | 628.29 |
| 4 | 8.55 (d, 1H), 8.24-8.15 (m, 3H) 7.94-7.81 (m, 4H), 7.63-7.50 (m, 10H), 7.38-7.25 (m, 6H), 7.16 (dd, 2H) 2.21-1.96 (m, 4H), 1.73-1.63 (m, 4H) | 603.27 | 602.27 |
| 11 | 8.55 (d, 1H), 8.24 (d, 1H) 7.98-7.86 (m, 4H), 7.62-7.50 (m, 7H), 7.38-7.16 (m, 12H), 6.91 (d, 1H) 2.21-1.96 (m, 4H), 1.73-1.63 (m, 4H) | 643.27 | 642.27 |
| 15 | 8.55 (d, 1H), 8.45 (d, 1H) 7.94-7.86 (m, 4H), 7.62-7.25 (m, 17H), 7.16 (m, 2H), 2.21-1.96 (m, 4H), 1.73-1.63 (m, 4H) | 659.24 | 658.24 |
| 20 | 8.55 (d, 1H), 8.31 (d, 1H), 7.97-7.86 (m, 4H), 7.74 (s, 1H), 7.62-7.50 (m, 8H), 7.37-7.00 (m, 18H), 2.21-1.96 (m, 4H), 1.73-1.63 (m, 4H) | 629.29 | 628.29 |
| 22 | 8.55 (d, 1H), 8.31 (d, 1H), 8.10 (d, 1H), 7.94-7.86 (m, 4H), 7.74 (s, 1H), 7.62-7.28 (m, 19H), 7.16-7.08 (m, 5H), 2.21-1.96 (m, 4H), 1.73-1.63 (m, 4H) | 705.32 | 704.32 |
| 23 | 8.55 (d, 1H), 8.31 (d, 1H), 8.22 (d, 1H), 8.15 (d, 1H), 7.94-7.81 (m, H), 7.74 (s, 1H), 7.62-7.40 (m, 12H), 7.38-7.28 (m, 6H), 7.14 (m, 2H), 2.21-1.96 (m, 4H), 1.73-1.63 (m, 4H) | 679.30 | 678.30 |
| 30 | 8.55 (d, 1H), 8.31 (d, 1H), 7.98-7.86 (m, 5H), 7.74 (s, 1H), 7.62-7.50 (m, 9H), 7.39-7.25 (m, 10H), 7.16 (m, 2H), 7.16 (m, 1H), 2.21-1.96 (m, 4H), 1.73-1.63 (m, 4H) | 719.30 | 718.30 |
| 34 | 8.55 (d, 1H), 8.45 (d, 1H), 8.31 (d, 1H) 7.94-7.86 (m, 5H), 7.74 (s, 1H), 7.62-7.28 (m, 19H), 7.16 (m, 2H), 7.16 (m, 1H), 2.21-1.96 (m, 4H), 1.73-1.63 (m, 4H) | 735.28 | 734.28 |

Manufacture of Organic Light-Emitting Device

Comparative Example 1

As an anode, an ITO glass substrate (Corning) having a thickness of 15 Ω/cm$^2$ (1,200 Å) was cut to a size of 50 mm×50 mm×0.7 mm, sonicated with isopropyl alcohol and pure water each for 5 minutes, and then, cleaned by exposure to ultraviolet rays and ozone for 30 minutes. Then, the glass substrate was provided to a vacuum deposition apparatus.

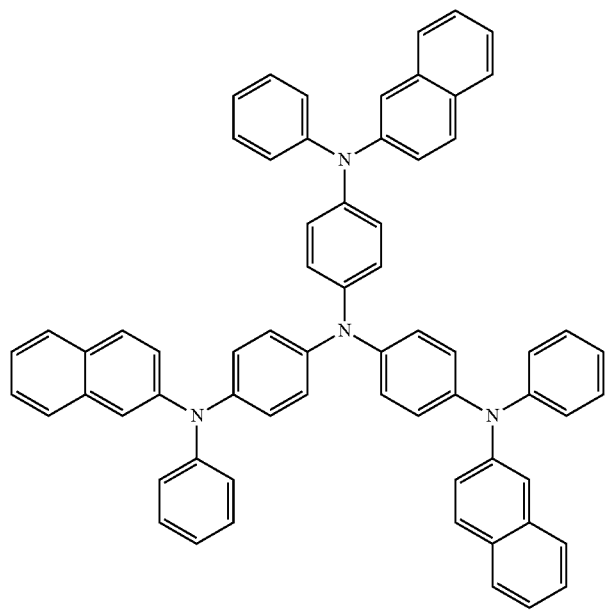
2-TNATA
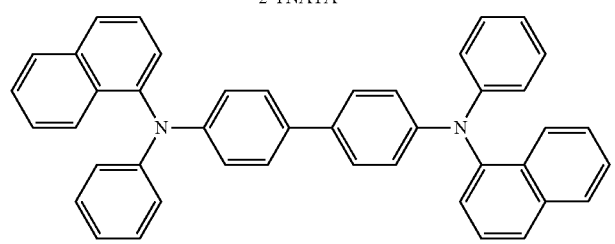
NPB
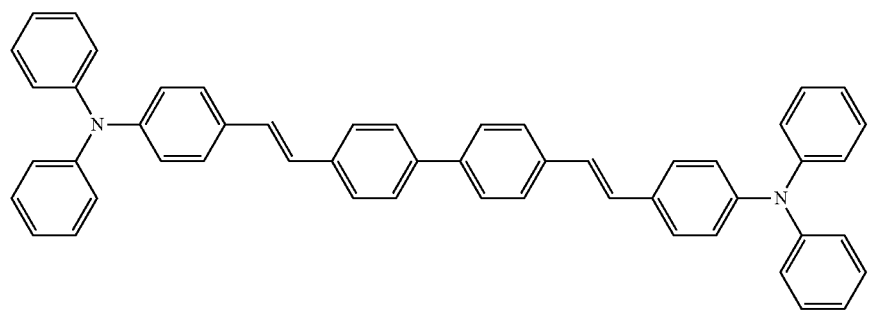
DPAVBi
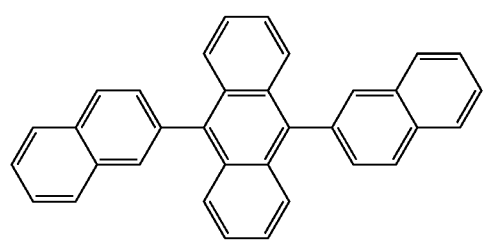
DNA

121

Comparative Example 2

An organic light-emitting device was manufactured in the same (or substantially the same) manner as in Comparative Example 1, except that Compound 100 was used instead of NPB in forming a hole transport layer.

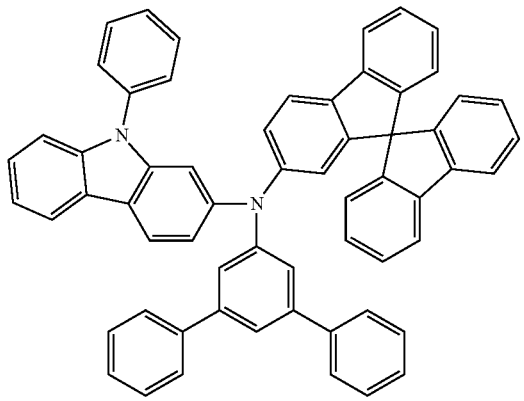

100

Comparative Example 3

An organic light-emitting device was manufactured in the same (or substantially the same) manner as in Comparative Example 1, except that Compound 101 was used instead of NPB in forming a hole transport layer.

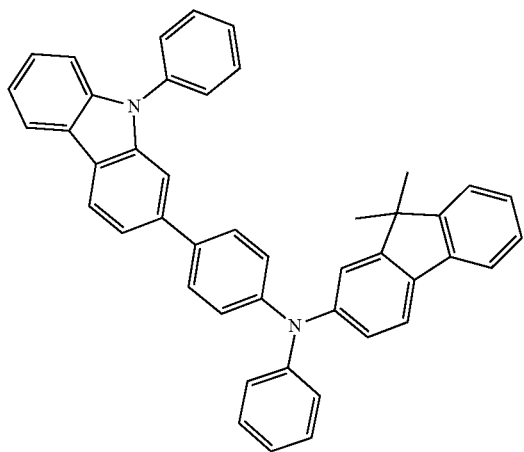

101

Comparative Example 4

An organic light-emitting device was manufactured in the same (or substantially the same) manner as in Comparative Example 1, except that Compound 102 was used instead of NPB in forming a hole transport layer.

122

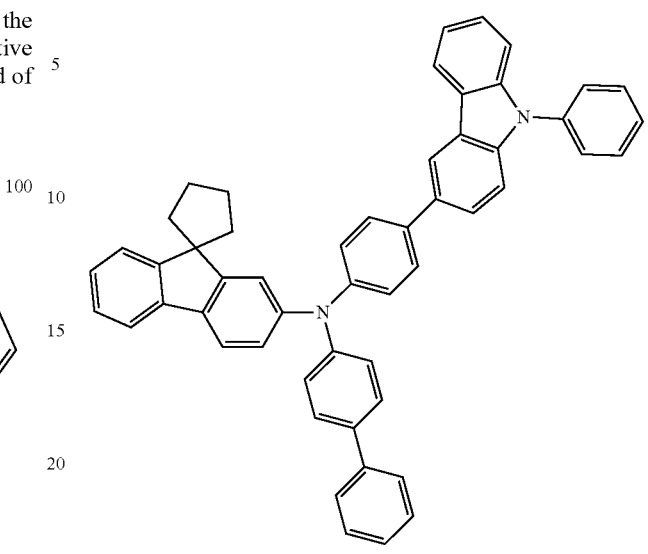

102

Example 1

An organic light-emitting device was manufactured in the same (or substantially the same) manner as in Comparative Example 1, except that Compound 1 was used instead of NPB in forming a hole transport layer.

Example 2

An organic light-emitting device was manufactured in the same (or substantially the same) manner as in Comparative Example 1, except that Compound 3 was used instead of NPB in forming a hole transport layer.

Example 3

An organic light-emitting device was manufactured in the same (or substantially the same) manner as in Comparative Example 1, except that Compound 4 was used instead of NPB in forming a hole transport layer.

Example 4

An organic light-emitting device was manufactured in the same (or substantially the same) manner as in Comparative Example 1, except that Compound 11 was used instead of NPB in forming a hole transport layer.

Example 5

An organic light-emitting device was manufactured in the same (or substantially the same) manner as in Comparative Example 1, except that Compound 15 was used instead of NPB in forming a hole transport layer.

Example 6

An organic light-emitting device was manufactured in the same (or substantially the same) manner as in Comparative Example 1, except that Compound 20 was used instead of NPB in forming a hole transport layer.

Example 7

An organic light-emitting device was manufactured in the same (or substantially the same) manner as in Comparative Example 1, except that Compound 22 was used instead of NPB in forming a hole transport layer.

Example 8

An organic light-emitting device was manufactured in the same (or substantially the same) manner as in Comparative Example 1, except that Compound 23 was used instead of NPB in forming a hole transport layer.

Example 9

An organic light-emitting device was manufactured in the same (or substantially the same) manner as in Comparative Example 1, except that Compound 30 was used instead of NPB in forming a hole transport layer.

Example 10

An organic light-emitting device was manufactured in the same (or substantially the same) manner as in Comparative Example 1, except that Compound 34 was used instead of NPB in forming a hole transport layer.

The driving voltage, current density, luminance, efficiency, and lifespan of the organic light-emitting devices manufactured according to Examples 1 to 9 and Comparative Examples 1 to 4 were measured, and results thereof are shown in Table 2 below.

TABLE 2

| | Hole transport material | Driving voltage (V) | Current density (mA/cm²) | Luminance (cd/m²) | Efficiency (cd/A) | Emission color | Half-lifespan (hr @ 100 mA/cm²) |
|---|---|---|---|---|---|---|---|
| Comparative Example 1 | NPB | 7.01 | 50 | 2645 | 5.29 | Blue | 258 |
| Comparative Example 2 | 100 | 4.73 | 50 | 2915 | 5.83 | Blue | 290 |
| Comparative Example 3 | 101 | 3.94 | 50 | 3360 | 6.72 | Blue | 301 |
| Comparative Example 4 | 102 | 3.68 | 50 | 3660 | 7.32 | Blue | 334 |
| Example 1 | Compound 1 | 3.42 | 50 | 3940 | 7.88 | Blue | 370 |
| Example 2 | Compound 3 | 3.44 | 50 | 3750 | 7.50 | Blue | 365 |
| Example 3 | Compound 4 | 3.32 | 50 | 3605 | 7.21 | Blue | 384 |
| Example 4 | Compound 11 | 3.56 | 50 | 3770 | 7.54 | Blue | 370 |
| Example 5 | Compound 15 | 3.45 | 50 | 3845 | 7.69 | Blue | 386 |
| Example 6 | Compound 20 | 3.56 | 50 | 3920 | 7.84 | Blue | 365 |
| Example 7 | Compound 22 | 3.74 | 50 | 3920 | 7.84 | Blue | 345 |
| Example 8 | Compound 23 | 3.95 | 50 | 3910 | 7.82 | Blue | 331 |
| Example 9 | Compound 30 | 3.63 | 50 | 3890 | 7.78 | Blue | 361 |
| Example 10 | Compound 34 | 3.43 | 50 | 3840 | 7.68 | Blue | 381 |

Referring to Table 2, it was confirmed that the organic light-emitting devices manufactured according to Examples 1 to 9 showed excellent results compared to those of the organic light-emitting devices manufactured according to Comparative Examples 1 to 4.

In the one or more embodiments of the present disclosure, an organic light-emitting device including a compound represented by Formula 1 shows excellent efficiency and improved lifespan.

As used herein, the singular forms "a," "an," and "the" are intended to include the plural forms as well, unless the context clearly indicates otherwise.

It will be further understood that the terms "includes," "including," "comprises," and/or "comprising," when used in this specification, specify the presence of stated features, steps, operations, elements, and/or components, but do not preclude the presence or addition of one or more other features, steps, operations, elements, components, and/or groups thereof.

As used herein, the terms "substantially", "about", and similar terms are used as terms of approximation and not as terms of degree, and are intended to account for the inherent deviations in measured or calculated values that would be recognized by those of ordinary skill in the art.

Any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the present disclosure as defined by the following claims and equivalents thereof.

What is claimed is:
1. A compound represented by Formula 1 below:

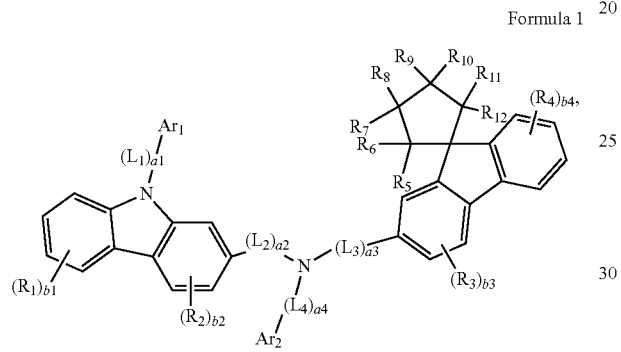

Formula 1 wherein, in Formula 1,
$L_1$, $L_2$, $L_3$, and $L_4$ are each independently selected from a substituted or unsubstituted $C_6$-$C_{60}$ arylene group and a substituted or unsubstituted $C_1$-$C_{60}$ heteroarylene group,
a1, a2, a3, and a4 are each independently an integer from 0 to 3,
$Ar_1$ and $R_1$ to $R_{12}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —B($Q_1$)($Q_2$), —C(=O)($Q_1$), —S(=O)$_2$($Q_1$), and —P(=O)($Q_1$)($Q_2$), wherein two adjacent substituents among $R_5$ to $R_{12}$ are not linked to each other to form a ring,
$Ar_2$ is Formula 4c,
b1 and b4 are each independently an integer from 1 to 4,
b2 and b3 are each independently an integer from 1 to 3,

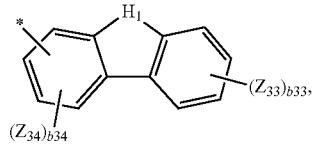

wherein, in Formula 4c,
$H_1$ is S,
$Z_{33}$ and $Z_{34}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a dibenzofuranyl group, a dibenzothiophenyl group, a triazinyl group, a benzimidazolyl group, and a phenanthrolinyl group,
b33 is an integer from 1 to 4,
b34 is an integer from 1 to 3, and
* indicates a binding site to a neighboring atom, and
at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted, a $C_6$-$C_{60}$ arylene group, the substituted $C_6$-$C_{60}$ aryloxy group, the substituted $C_6$-$C_{60}$ arylthio group, the substituted $C_1$-$C_{60}$ heteroaryl group, the substituted $C_1$-$C_{60}$ heteroarylene group, the substituted monovalent non-aromatic condensed polycyclic group, and the substituted monovalent non-aromatic condensed heteropolycyclic group is selected from:
deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;
a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —B($Q_{11}$)($Q_{12}$), —C(=O)($Q_{11}$), —S(=O)$_2$($Q_{11}$), and —P(=O)($Q_{11}$)($Q_{12}$);
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —B($Q_{31}$)($Q_{32}$), —C(=O)($Q_{31}$), —S(=O)$_2$($Q_{31}$), and —P(=O)($Q_{31}$)($Q_{32}$), and $Q_1$, $Q_2$, $Q_3$, $Q_{11}$, $Q_{12}$, $Q_{13}$, $Q_{21}$, $Q_{22}$, $Q_{23}$, $Q_{31}$, $Q_{32}$, and $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

2. The compound of claim 1, wherein $Ar_1$ is selected from a substituted or unsubstituted $C_6$-$C_{60}$ aryl group and a substituted or unsubstituted $C_1$-$C_{60}$ heteroaryl group.

3. The compound of claim 1, wherein $Ar_1$ is selected from Formula 2a:

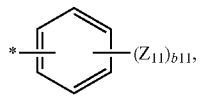

2a wherein, in Formula 2a, $Z_{11}$ is selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a dibenzofuranyl group, a dibenzothiophenyl group, a triazinyl group, a benzimidazolyl group, and a phenanthrolinyl group, b11 is an integer from 1 to 5, and

* indicates a binding site to a neighboring atom.

4. The compound of claim 1, wherein a1 is 0 or 1.

5. The compound of claim 1, wherein $L_1$, $L_2$, $L_3$, and $L_4$ in Formula 1 are each independently a substituted or unsubstituted $C_6$-$C_{60}$ arylene group.

6. The compound of claim 1, wherein, $L_1$, $L_2$, $L_3$, and $L_4$ in Formula 1 are each independently selected from:

a phenylene group, a pentalenylene group, an indenylene group, a naphthylene group, an azulenylene group, a heptalenylene group, an indacenylene group, an acenaphthylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, and an ovalenylene group; and a phenylene group, a pentalenylene group, an indenylene group, a naphthylene group, an azulenylene group, a heptalenylene group, an indacenylene group, an acenaphthylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, and an ovalenylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolylene group, a thiadiazolyl group, an imidazopyridinyl group, an imidazopyrimidinyl group, —Si($Q_{31}$)($Q_{32}$)($Q_{33}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ are each independently selected from hydrogen, deuterium, —F, —Cl , —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

7. The compound of claim 1, wherein $L_2$, $L_3$, and $L_4$ in Formula 1 are each independently selected from groups represented by Formula 3a:

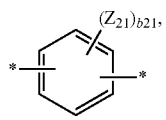

3a wherein, in Formula 3a, $Z_{21}$ is selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a dibenzofuranyl group, a dibenzothiophenyl group, a triazinyl group, a benzimidazolyl group, and a phenanthrolinyl group, b21 is an integer from 1 to 4, and

* indicates a binding site to a neighboring atom.

8. The compound of claim 1, wherein $R_1$ to $R_{12}$ are each independently hydrogen or deuterium.

9. The compound of claim 1, wherein Formula 1 is Formula 2 below:

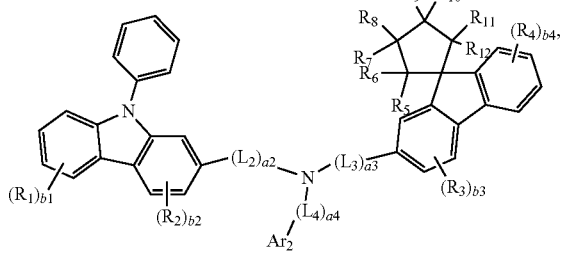

Formula 2 wherein, in Formula 2, $L_2$ to $L_4$, Are, $R_1$ to $R_{12}$, a2 to a4, and b1 to b4 are the same as defined in connection with Formula 1.

10. The compound of claim 1, wherein Formula 1 is Formula 3 below:

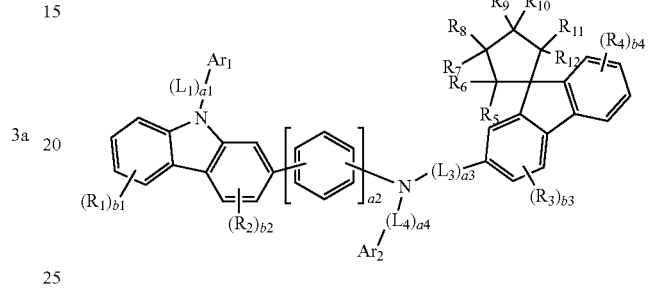

Formula 3 wherein, in Formula 3, $L_1$, $L_3$, $L_4$, $Ar_1$, $Ar_2$, $R_1$ to $R_{12}$, a1 to a4, and b1 to b4 are the same as defined in connection with Formula 1.

11. The compound of claim 1, wherein Formula 1 is Formula 4 below:

Formula 4 wherein, in Formula 4, $L_1$, $L_2$, $L_4$, $Ar_1$, $Ar_2$, $R_1$ to $R_{12}$, a1 to a4, and b1 to b4 are the same as defined in connection with Formula 1.

12. The compound of claim 1, wherein Formula 1 is Formula 5 below:

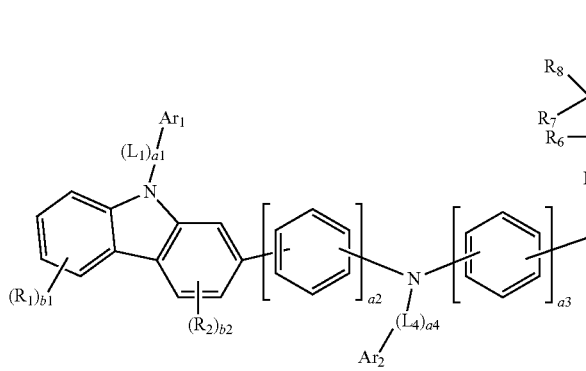

Formula 5 wherein, in Formula 5, $L_1$, $L_4$, $Ar_1$, $Ar_2$, $R_1$ to $R_{12}$, a1 to a4, and b1 to b4 are the same as defined in connection with Formula 1.

13. An organic light-emitting device comprising:

a first electrode;

a second electrode facing the first electrode; and an organic layer between the first electrode and the second electrode and comprising an emission layer, wherein the organic layer comprises the compound of claim 1.

14. The organic light-emitting device of claim 13, wherein the emission layer is a fluorescent emission layer.

15. The organic light-emitting device of claim 13, wherein the first electrode is an anode, the second electrode is a cathode, the organic layer between the first electrode and the second electrode comprises i) a hole transport region between the first electrode and the emission layer, the hole transport region comprising a hole injection layer, a hole transport layer, a buffer layer, an electron blocking layer, or any combination thereof, and ii) an electron transport region between the emission layer and the second electrode, electron transport region comprising a hole blocking layer, an electron transport layer, an electron injection layer, or any combination thereof.

16. The organic light-emitting device of claim 15, wherein the hole transport region comprises the compound.

17. The organic light-emitting device of claim 13, wherein the emission layer comprises a styrylamine compound.

18. An electronic apparatus comprising:

a thin-film transistor and the organic light-emitting device of claim 13, wherein the thin-film transistor includes a source electrode, a drain electrode, an activation layer, and a gate electrode, and the first electrode of the organic light-emitting device is in electrical contact with one of the source electrode and the drain electrode of the thin-film transistor.

19. A compound is selected from Compounds 1, to 10, 12 to 29, 31 to 48, 50 to 67, and 69 to 76 below:

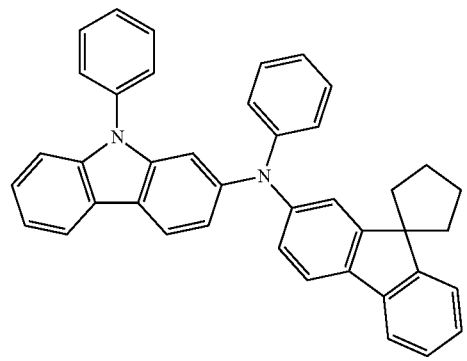

1

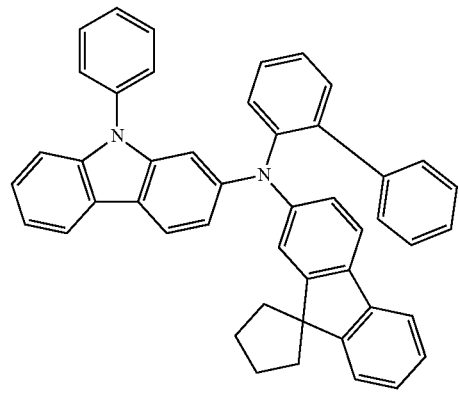

3

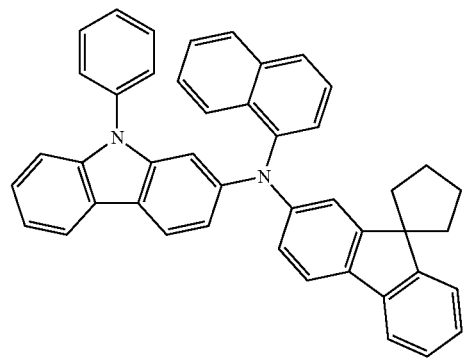

4

133
-continued
134
-continued
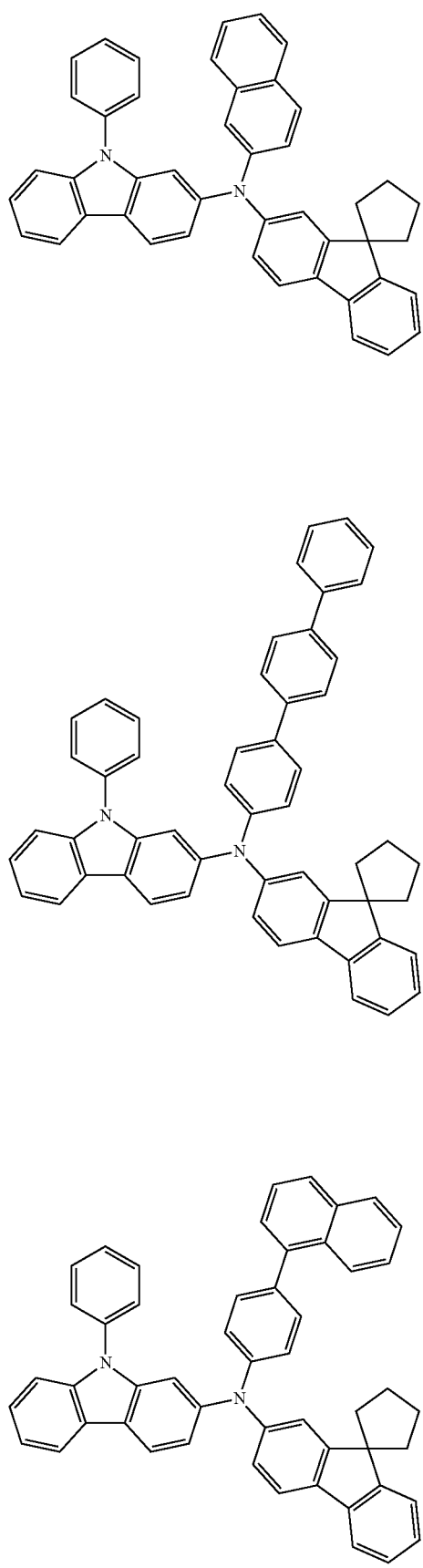
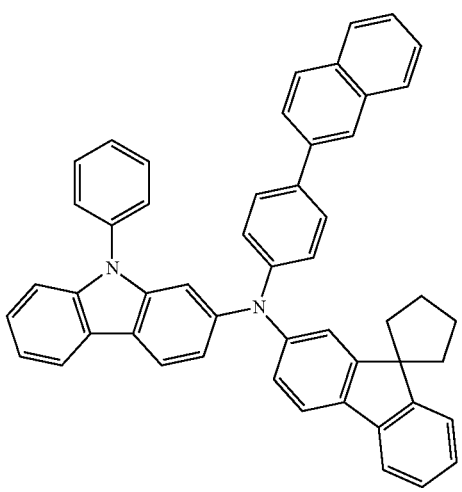
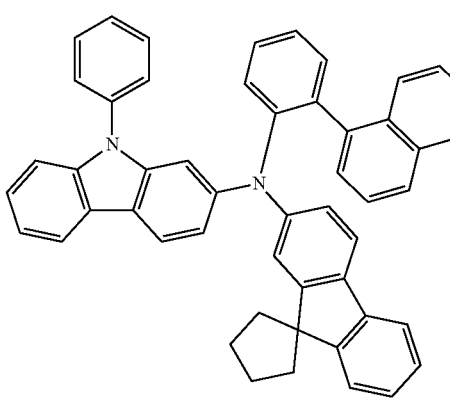
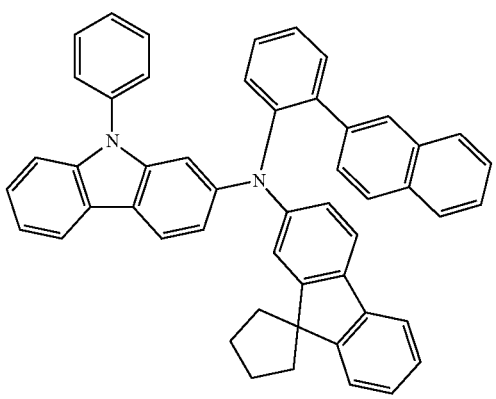
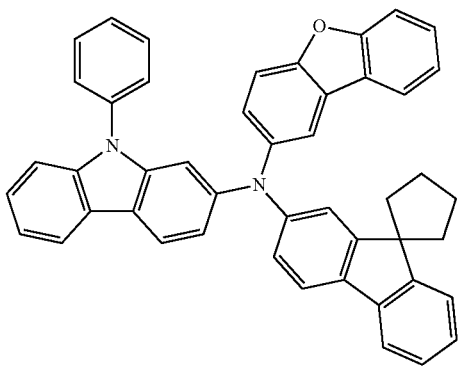

13
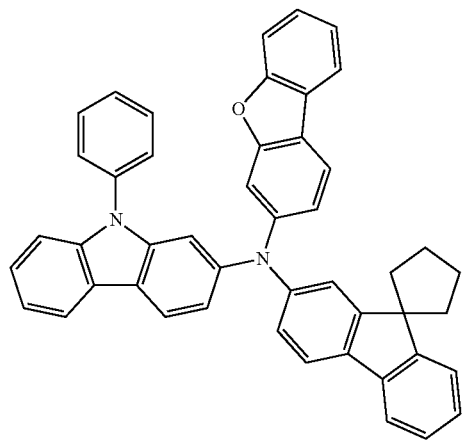
14
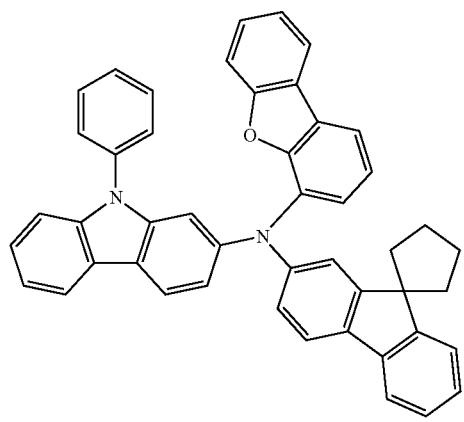
15
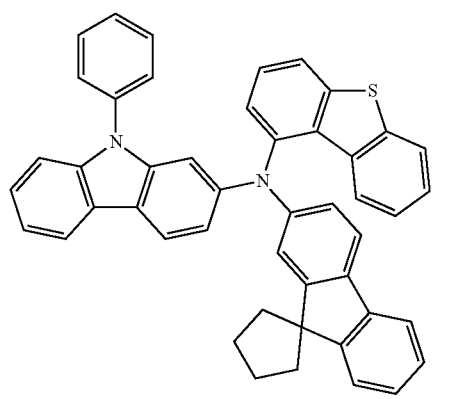
16
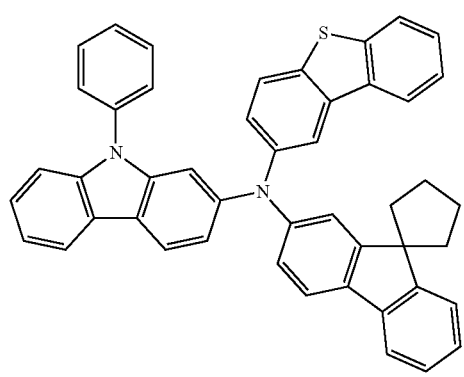
17
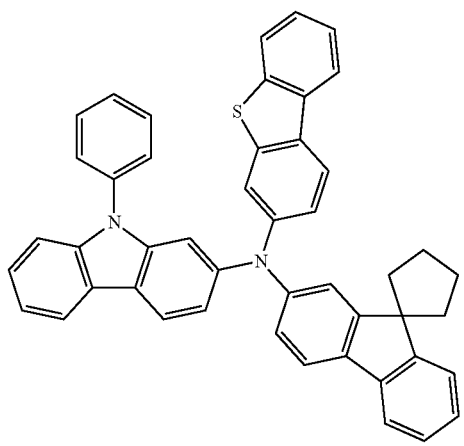
18
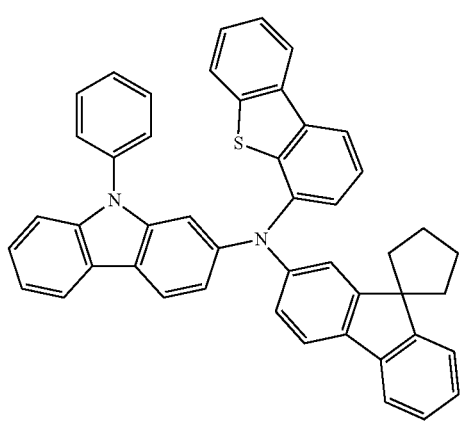
19
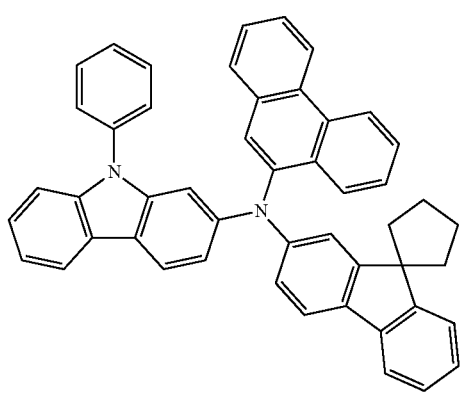
20
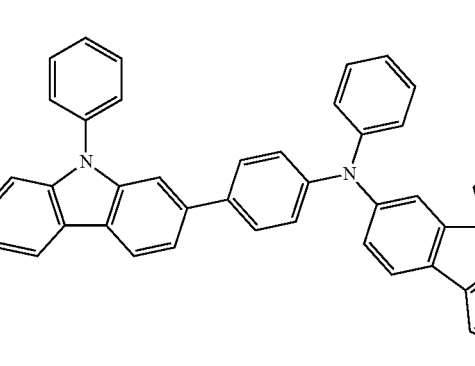

-continued
21
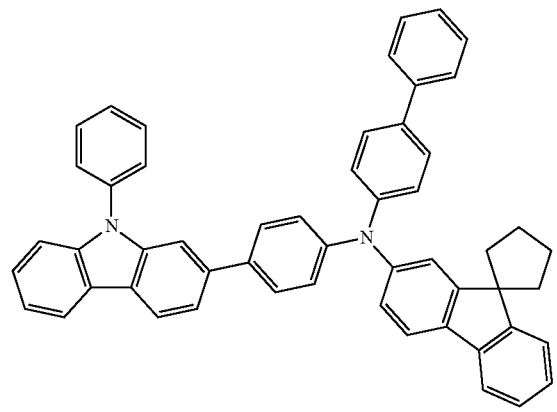
22
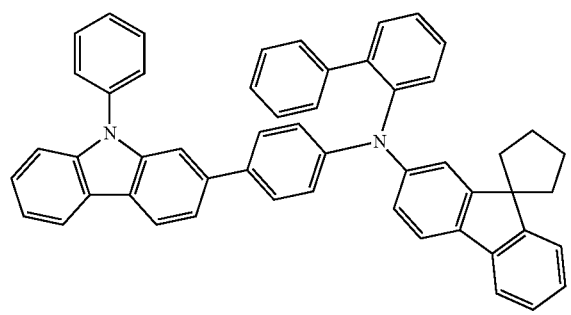
23
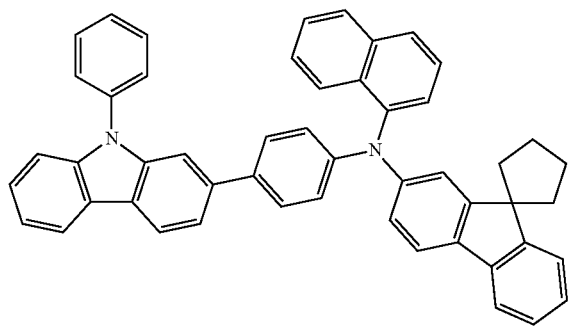
24
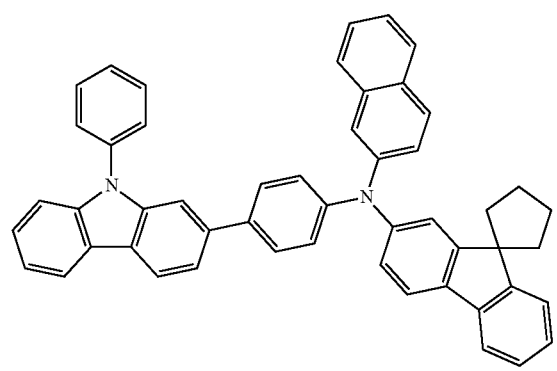
-continued
25
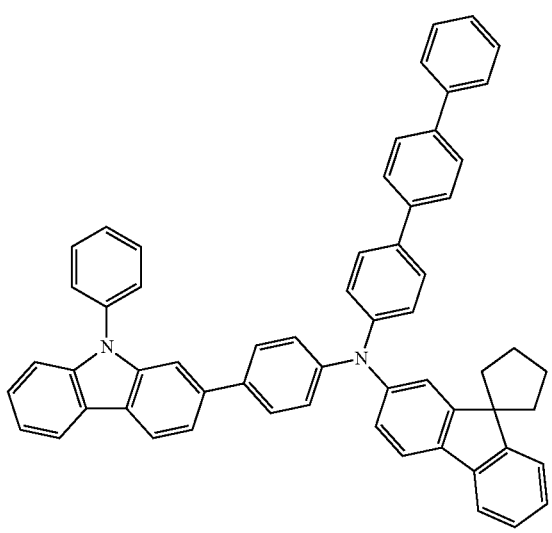
26
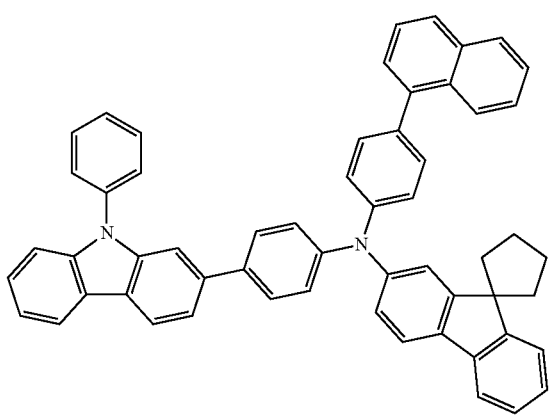
27
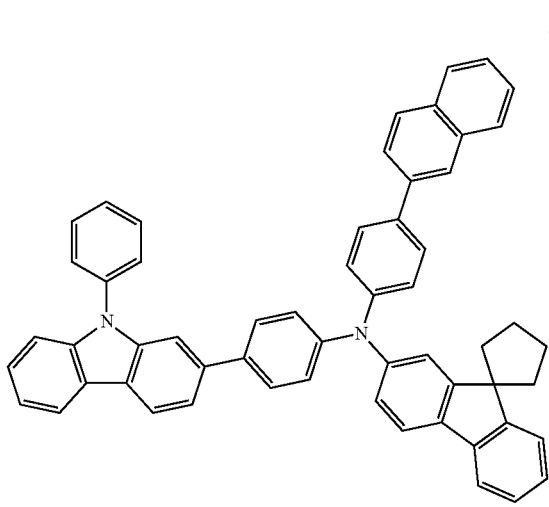

28
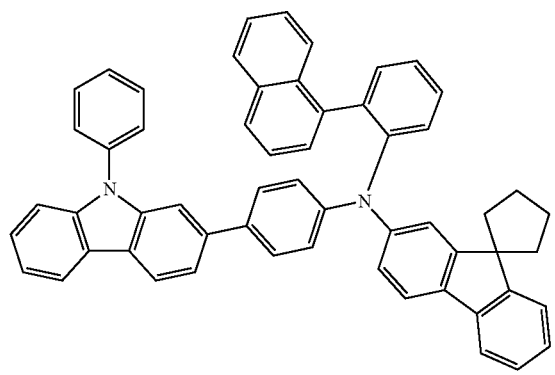
29
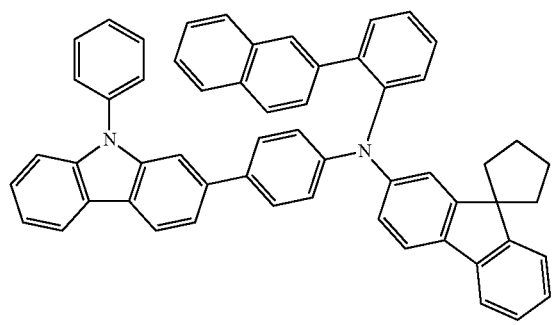
31
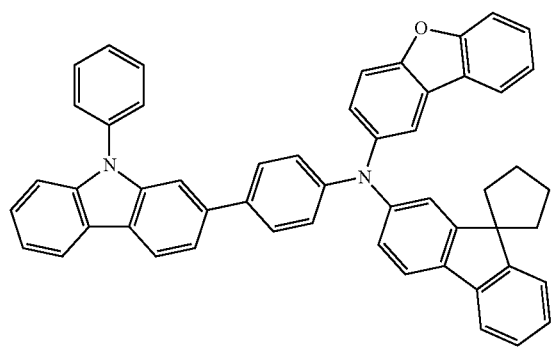
33
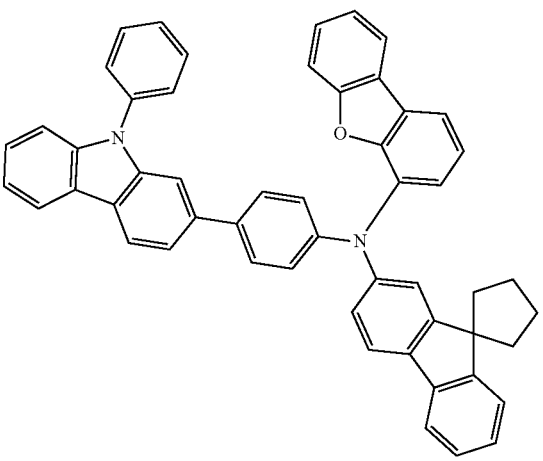
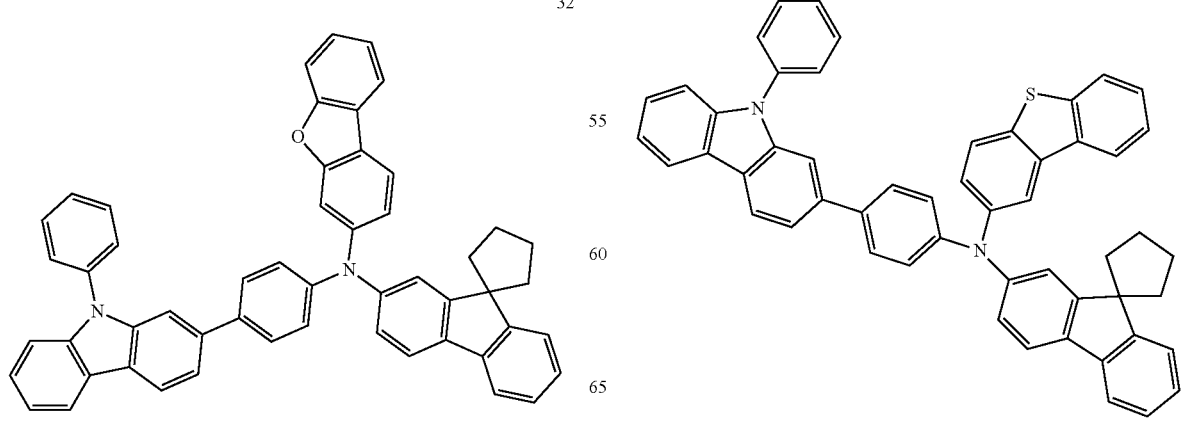

36
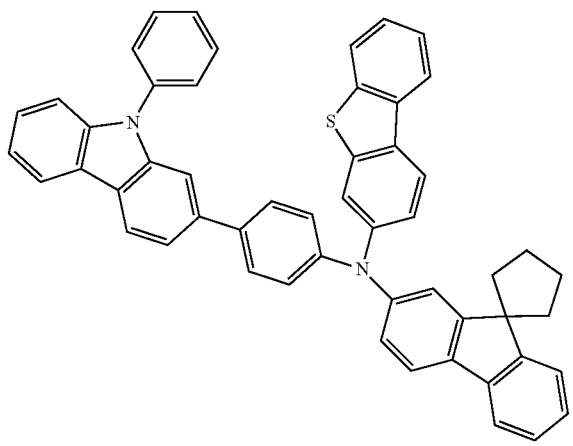
37
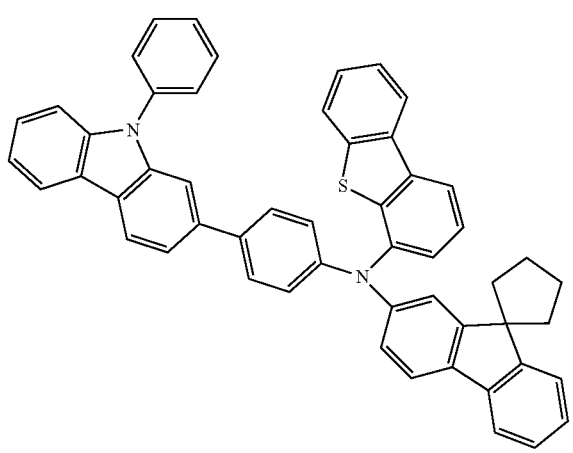
38
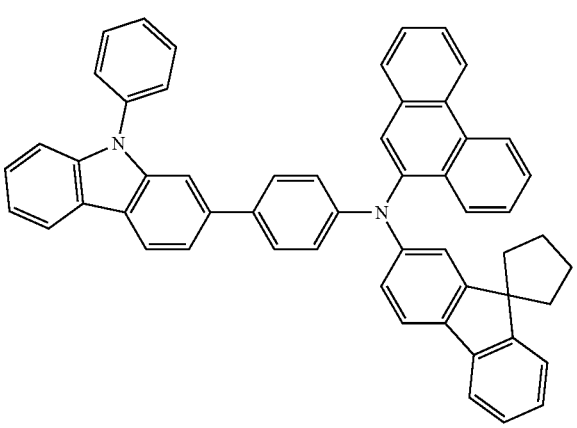
39
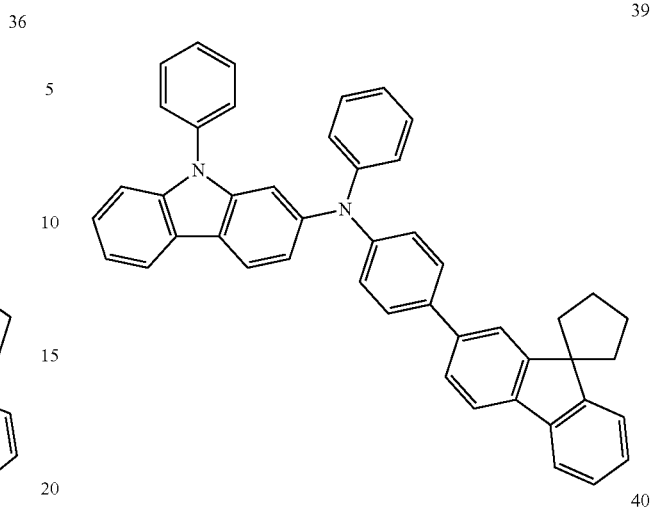
40
41
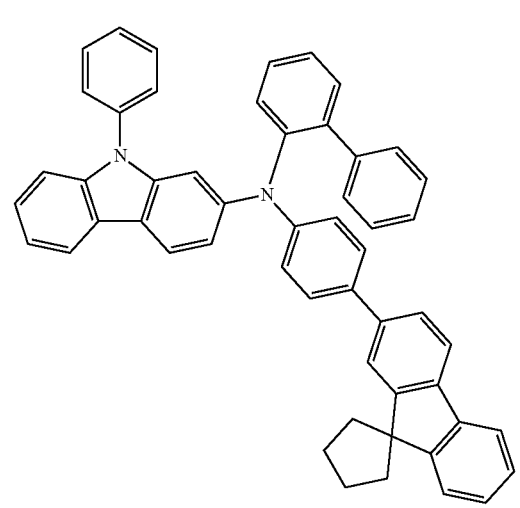

42
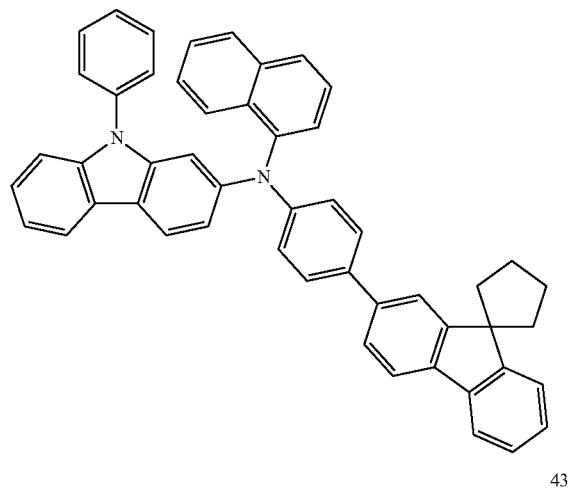
43
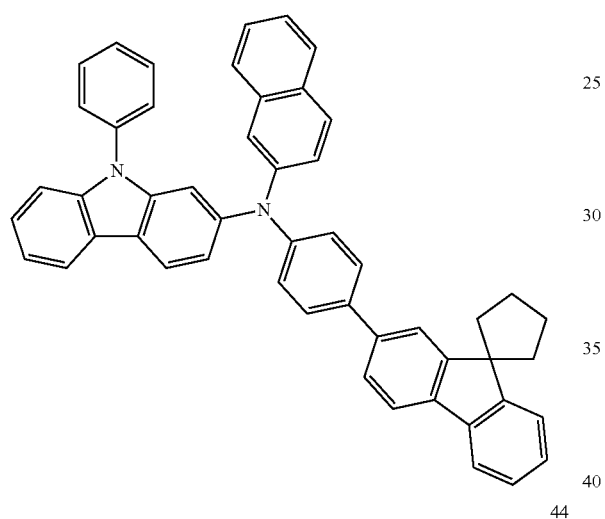
44
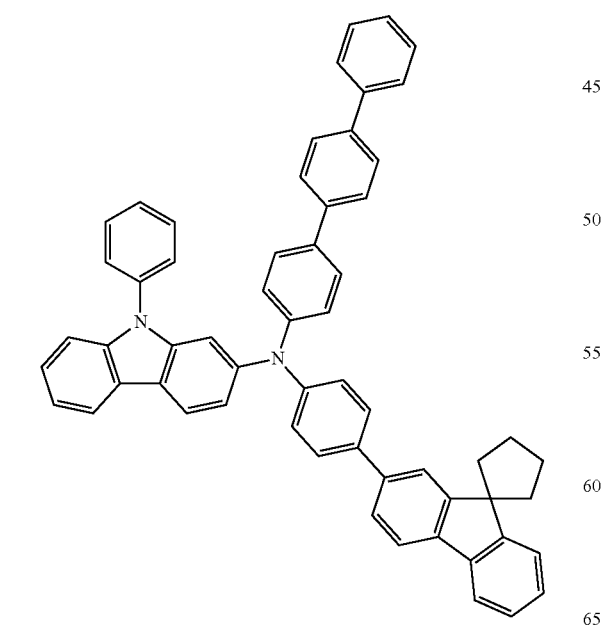
45
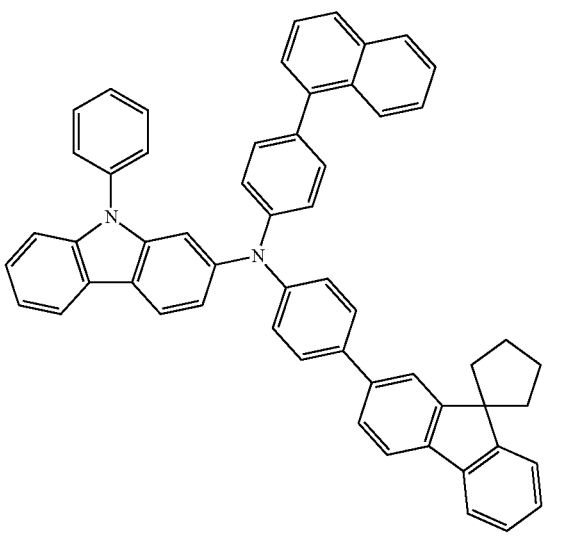
46
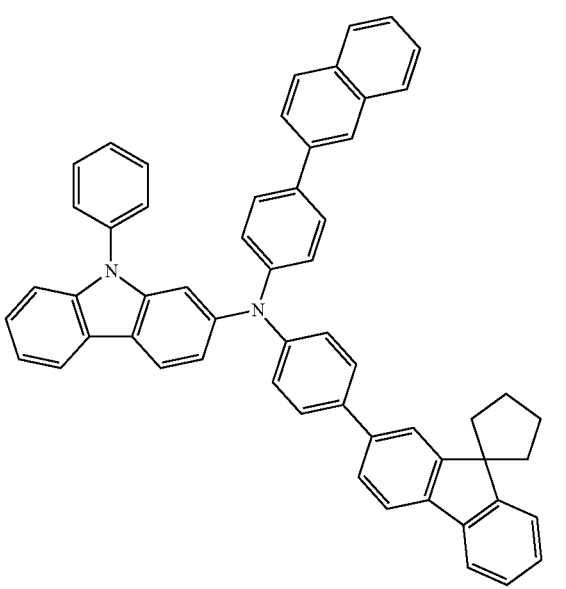
47
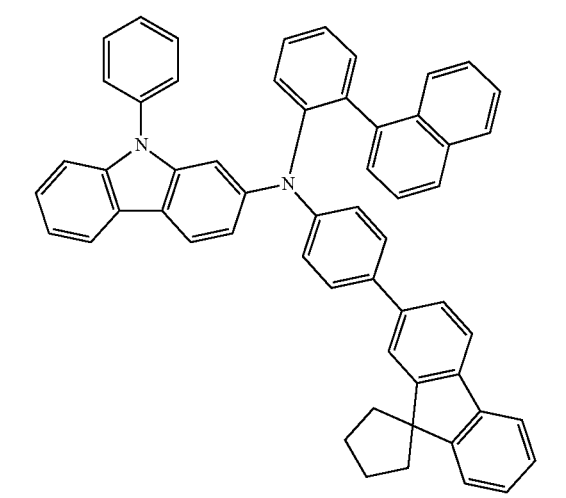

48
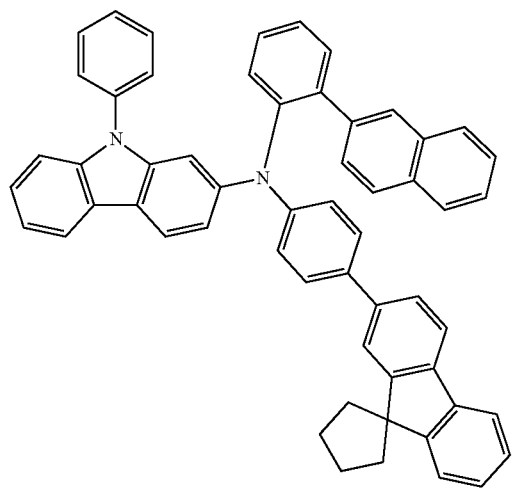
50
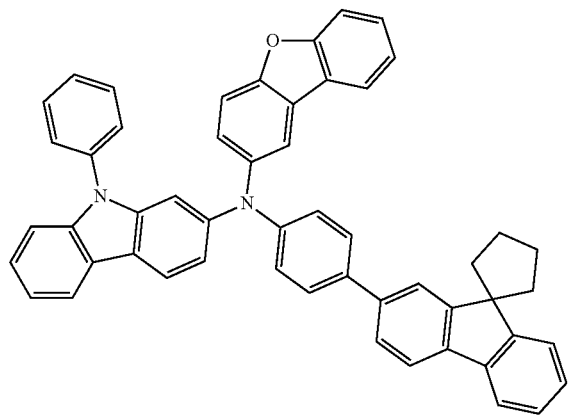
51
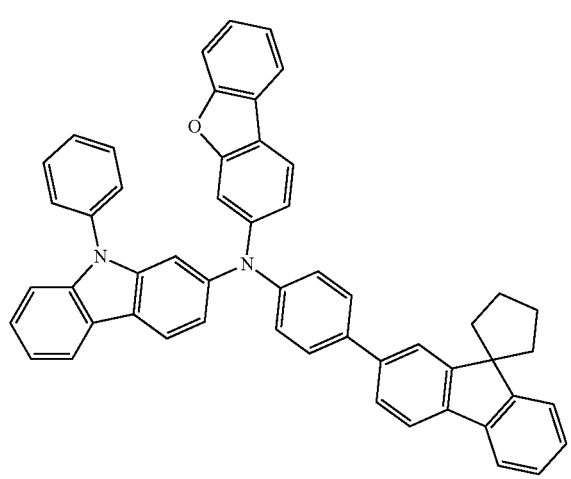
52
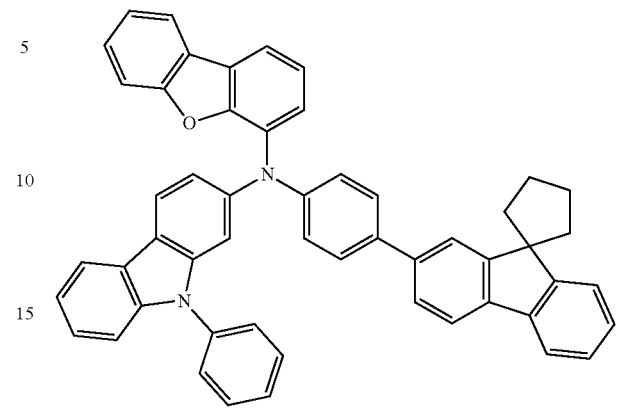
53
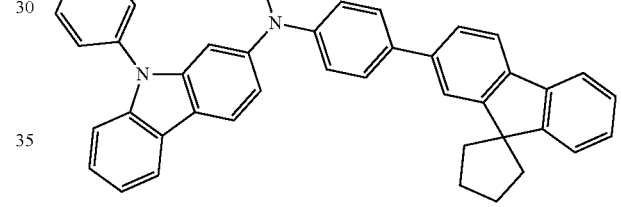
54
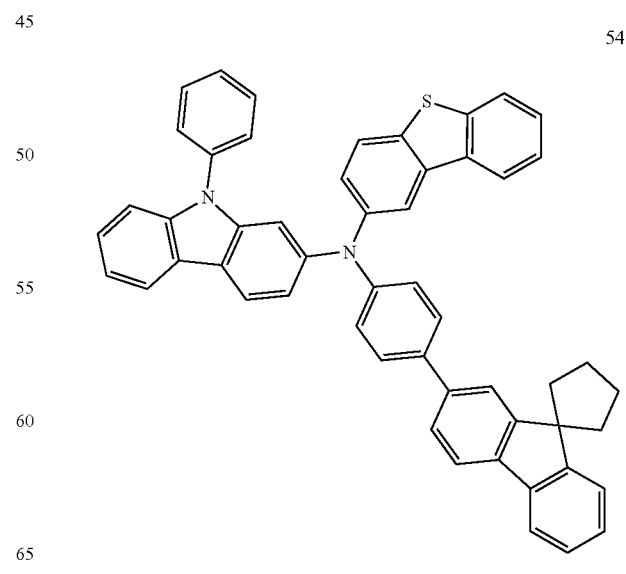

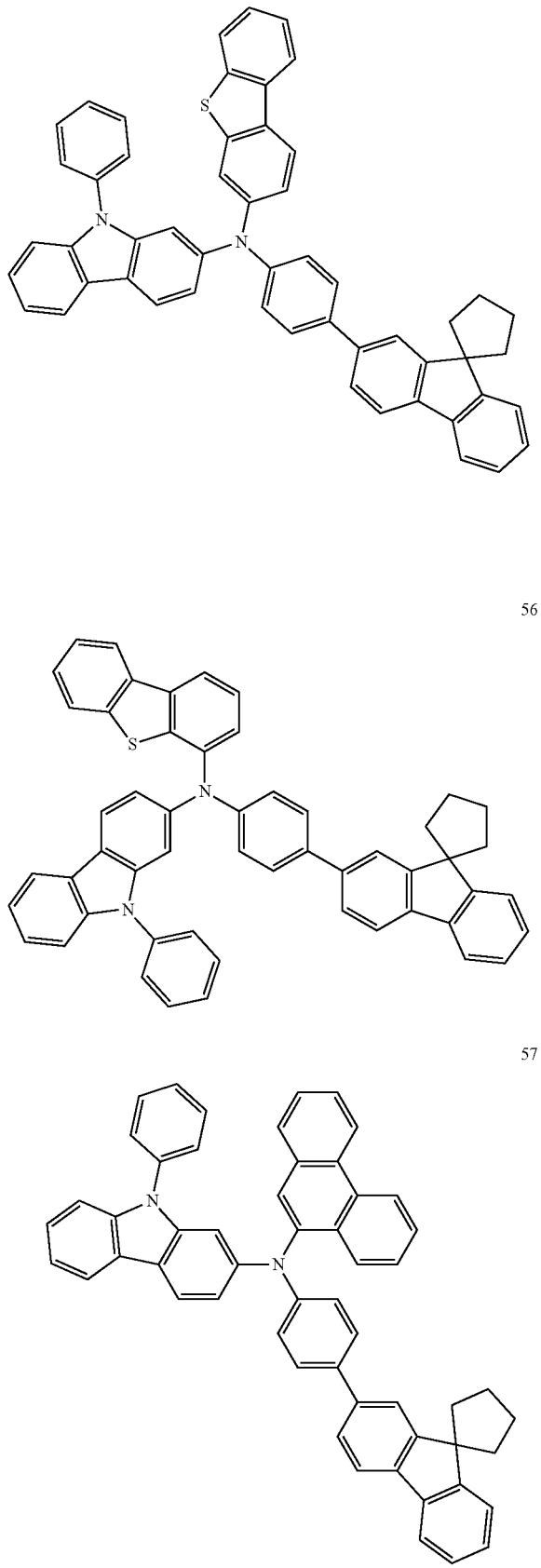
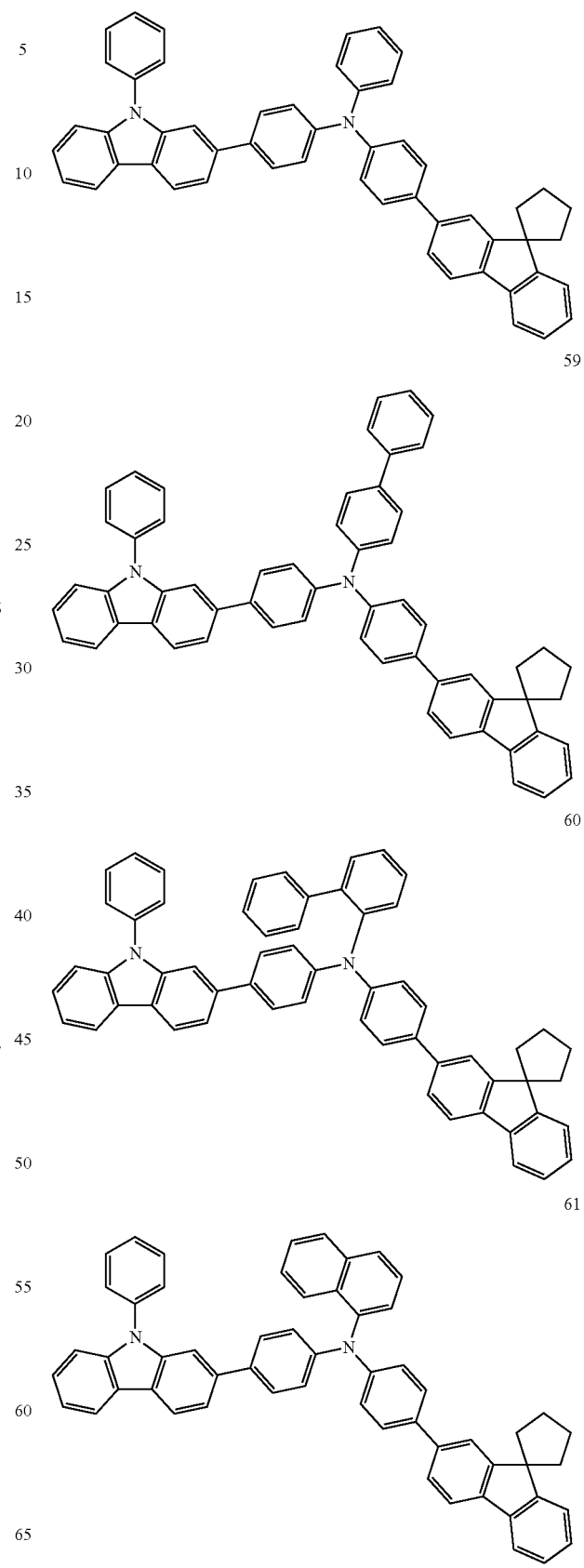

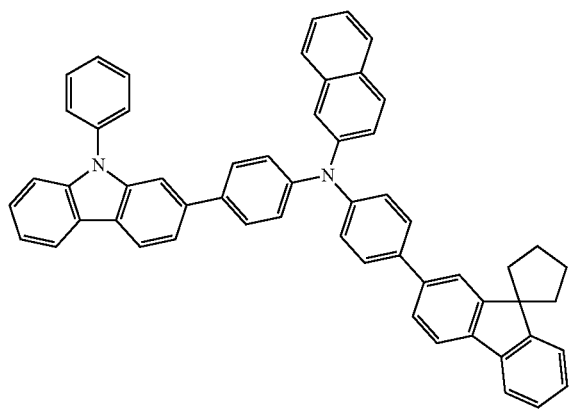
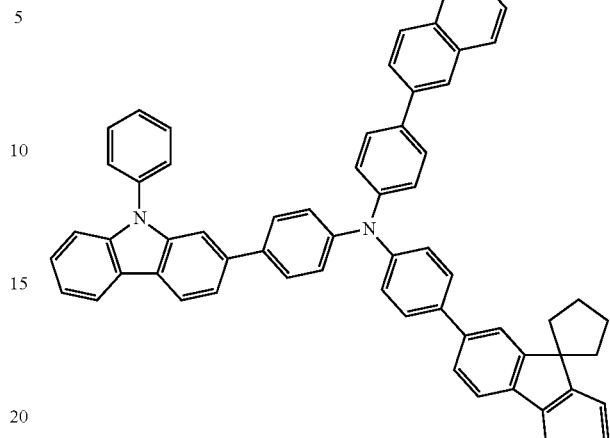
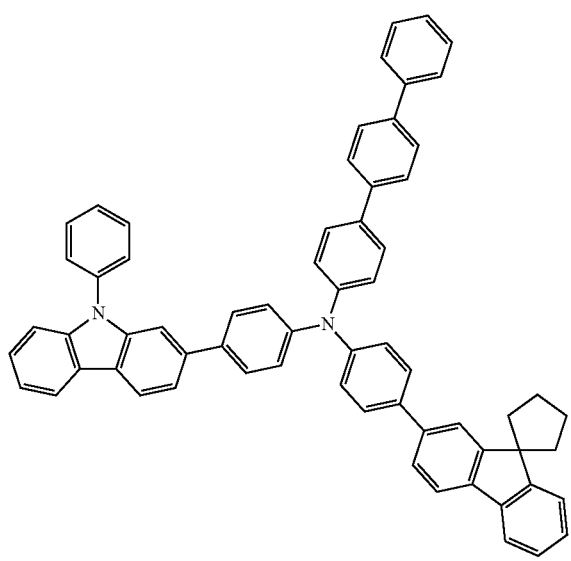
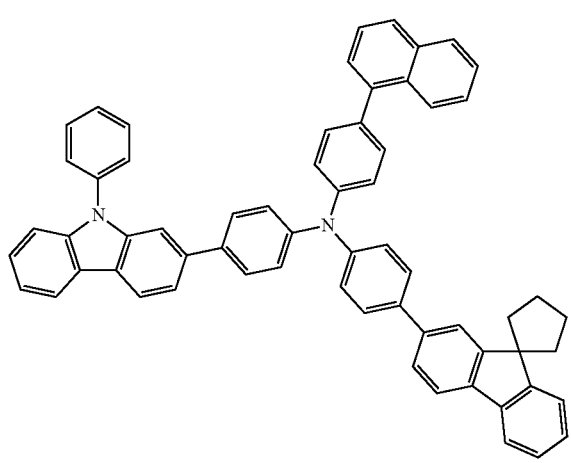
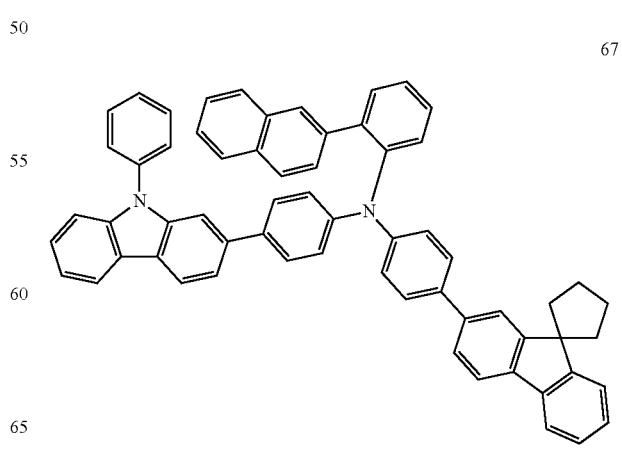

69
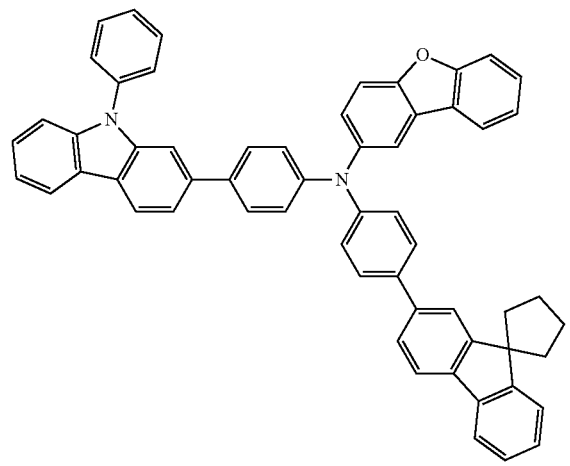
70
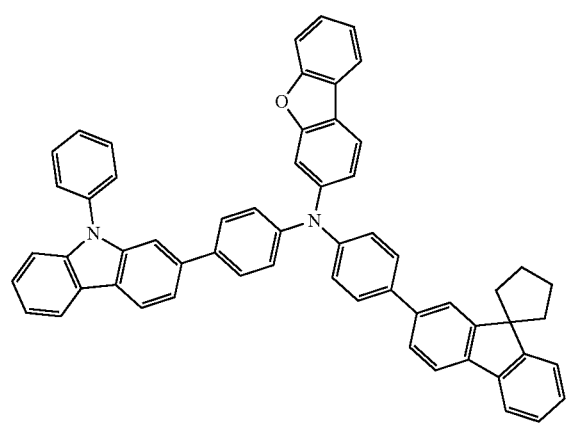
71
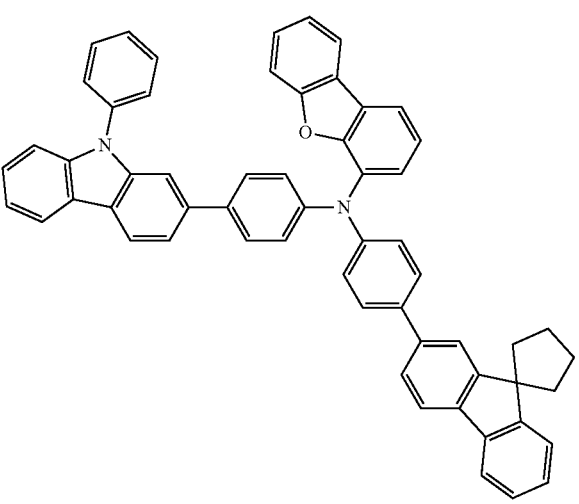
72
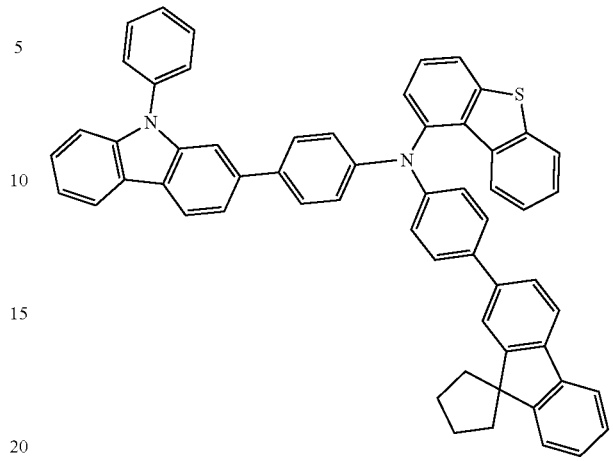
73
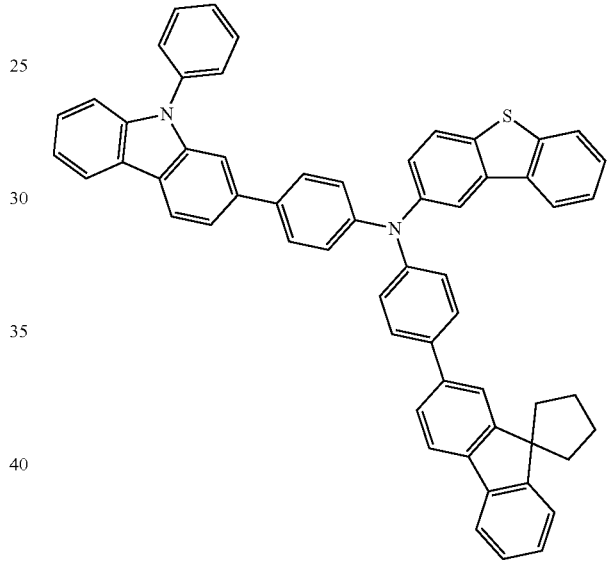
74
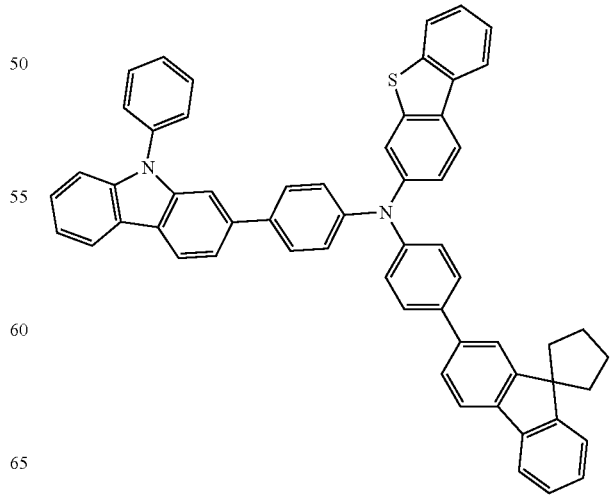

153
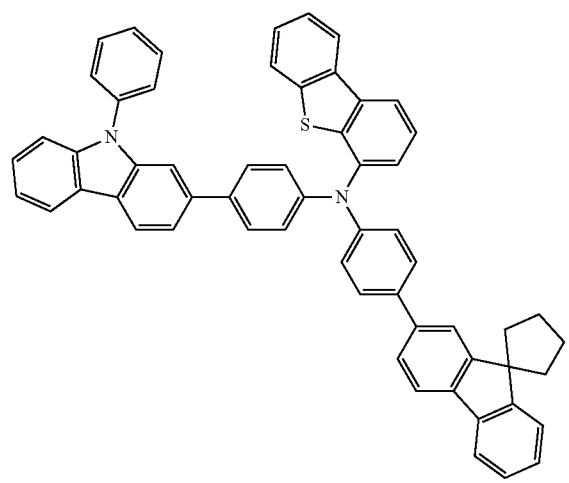
154
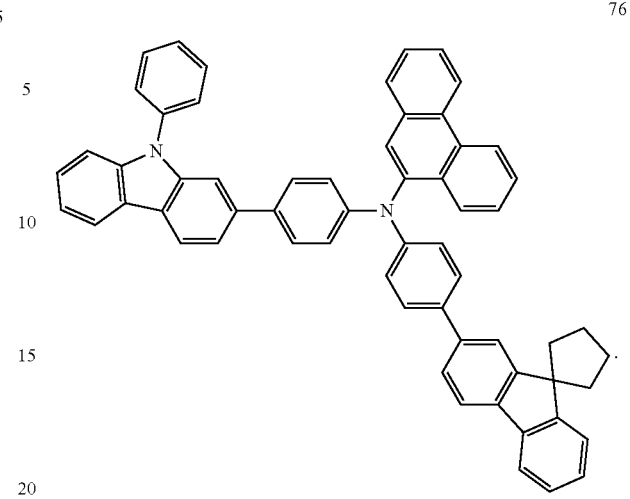
* * * * *